US011559582B2

(12) United States Patent
Satpayev et al.

(10) Patent No.: US 11,559,582 B2
(45) Date of Patent: *Jan. 24, 2023

(54) ANTIBODY DRUG CONJUGATES (ADC) THAT BIND TO 191P4D12 PROTEINS

(71) Applicants: AGENSYS, INC., Santa Monica, CA (US); SEAGEN INC., Bothell, WA (US)

(72) Inventors: Daulet Satpayev, Santa Monica, CA (US); Robert Kendall Morrison, Santa Monica, CA (US); Karen Jane Meyrick Morrison, Santa Monica, CA (US); Jean Gudas, Los Angeles, CA (US); Aya Jakobovits, South San Francisco, CA (US); Michael Torgov, Santa Monica, CA (US); Zili An, Santa Monica, CA (US)

(73) Assignees: AGENSYS, INC., Northbrook, IL (US); SEAGEN INC., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/122,786

(22) Filed: Dec. 15, 2020

(65) Prior Publication Data

US 2021/0283268 A1 Sep. 16, 2021

Related U.S. Application Data

(63) Continuation of application No. 15/943,527, filed on Apr. 2, 2018, now Pat. No. 10,894,090, which is a continuation of application No. 15/069,853, filed on Mar. 14, 2016, now Pat. No. 9,962,454, which is a continuation of application No. 14/798,302, filed on Jul. 13, 2015, now Pat. No. 9,314,538, which is a continuation of application No. 13/830,899, filed on Mar. 14, 2013, now Pat. No. 9,078,931, which is a continuation of application No. 13/249,111, filed on Sep. 29, 2011, now Pat. No. 8,637,642.

(60) Provisional application No. 61/387,933, filed on Sep. 29, 2010.

(51) Int. Cl.
| | |
|---|---|
| *A61K 39/395* | (2006.01) |
| *A61K 47/68* | (2017.01) |
| *C07K 16/30* | (2006.01) |
| *A61K 39/00* | (2006.01) |

(52) U.S. Cl.
CPC ...... *A61K 47/6851* (2017.08); *A61K 47/6801* (2017.08); *A61K 47/6803* (2017.08); *C07K 16/30* (2013.01); *A61K 2039/505* (2013.01); *C07K 2317/34* (2013.01); *C07K 2317/565* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,122,368 A | 6/1992 | Greenfield et al. |
| 6,264,949 B1 | 7/2001 | Friedman |
| 6,436,703 B1 | 8/2002 | Tanq et al. |
| 6,794,501 B2 | 9/2004 | Chen et al. |
| 7,098,316 B2 | 8/2006 | Ni et al. |
| 7,171,311 B2 | 1/2007 | Dai et al. |
| 7,175,849 B2 | 2/2007 | Baum et al. |
| 7,189,507 B2 | 3/2007 | Mack et al. |
| 7,659,241 B2 | 2/2010 | Senter et al. |
| 7,745,394 B2 | 6/2010 | Doronina et al. |
| 7,829,531 B2 | 11/2010 | Senter et al. |
| 7,851,437 B2 | 12/2010 | Senter et al. |
| 7,951,546 B2 | 5/2011 | Frantz et al. |
| 7,964,566 B2 | 6/2011 | Doronina et al. |
| 7,968,090 B2 | 6/2011 | Raitano et al. |
| 8,637,642 B2 | 1/2014 | Satpayev et al. |
| 9,078,931 B2 | 7/2015 | Satpayev et al. |
| 9,314,538 B2 | 4/2016 | Satpayev et al. |
| 9,962,454 B2 | 5/2018 | Satpayev et al. |
| RE48,389 E | 1/2021 | Satpayev et al. |
| 10,894,090 B2 | 1/2021 | Satpayev et al. |
| 2001/0051344 A1 | 12/2001 | Shalon et al. |
| 2002/0065220 A1 | 5/2002 | Young et al. |
| 2002/0090672 A1 | 7/2002 | Rosen et al. |
| 2002/0137160 A1 | 9/2002 | Byatt et al. |
| 2003/0065156 A1 | 4/2003 | Williams et al. |
| 2003/0073144 A1 | 4/2003 | Benson et al. |
| 2003/0077606 A1 | 4/2003 | Rosen et al. |
| 2003/0083263 A1 | 5/2003 | Doronina et al. |
| 2003/0099974 A1 | 5/2003 | Lillie et al. |

(Continued)

FOREIGN PATENT DOCUMENTS

| | | |
|---|---|---|
| AU | 2008202217 | 6/2008 |
| CA | 2496923 | 2/2004 |

(Continued)

OTHER PUBLICATIONS

Alberts et al., Molecular Bioloqy of the Cell, 3rd Ed. (1994) p. 465.

(Continued)

*Primary Examiner* — Christine J Saoud
(74) *Attorney, Agent, or Firm* — Jones Day

(57) ABSTRACT

Antibody drug conjugates (ADC's) that bind to 191P4D12 protein and variants thereof are described herein. 191P4D12 exhibits tissue specific expression in normal adult tissue, and is aberrantly expressed in the cancers listed in Table I. Consequently, the ADC's of the invention provide a therapeutic composition for the treatment of cancer.

32 Claims, 37 Drawing Sheets

Specification includes a Sequence Listing.

(56) References Cited

U.S. PATENT DOCUMENTS

| | | |
|---|---|---|
| 2003/0109690 A1 | 6/2003 | Ruben et al. |
| 2003/0148408 A1 | 8/2003 | Frantz et al. |
| 2003/0165831 A1 | 9/2003 | Lee et al. |
| 2003/0170621 A1 | 9/2003 | McCarthy et al. |
| 2003/0232350 A1 | 12/2003 | Afar et al. |
| 2004/0005563 A1 | 1/2004 | Mack et al. |
| 2004/0009491 A1 | 1/2004 | Birse et al. |
| 2004/0029114 A1 | 2/2004 | Mack et al. |
| 2004/0076955 A1 | 4/2004 | Mack et al. |
| 2004/0083497 A1 | 4/2004 | Raitano et al. |
| 2004/0259086 A1 | 12/2004 | Schlegel et al. |
| 2005/0112568 A1 | 5/2005 | Friedman et al. |
| 2006/0275211 A1 | 12/2006 | Jakobovits et al. |
| 2008/0268476 A1 | 10/2008 | Lopez |
| 2009/0203538 A1 | 8/2009 | Sugioka et al. |
| 2011/0064753 A1 | 3/2011 | Senter et al. |
| 2011/0201052 A1 | 8/2011 | Raitano et al. |
| 2018/0296693 A1 | 10/2018 | Satpayev et al. |

FOREIGN PATENT DOCUMENTS

| | | |
|---|---|---|
| CN | 1313297 A | 9/2001 |
| CN | 101500590 A | 8/2009 |
| EP | 1074617 A2 | 2/2001 |
| JP | 2006513724 A | 4/2006 |
| JP | 2010523469 A | 7/2010 |
| TW | I524901 B | 3/2016 |
| WO | WO 1999052942 A2 | 10/1999 |
| WO | WO 2001002568 A2 | 1/2001 |
| WO | WO 2001018016 A1 | 3/2001 |
| WO | WO 2001022920 A2 | 4/2001 |
| WO | WO 2001051628 A2 | 7/2001 |
| WO | WO 2001054474 A2 | 8/2001 |
| WO | WO 2001055315 A2 | 8/2001 |
| WO | WO 2001057188 A2 | 8/2001 |
| WO | WO 2001060860 A2 | 8/2001 |
| WO | WO 2001070979 A2 | 9/2001 |
| WO | WO 2001090304 A2 | 11/2001 |
| WO | WO 2001094629 A2 | 12/2001 |
| WO | WO 2002010449 A2 | 2/2002 |
| WO | WO 2002028902 A2 | 4/2002 |
| WO | WO 2002059377 A2 | 8/2002 |
| WO | WO 2002060317 A2 | 8/2002 |
| WO | WO 2002086084 A2 | 10/2002 |
| WO | WO 2002086443 A2 | 10/2002 |
| WO | WO 2002099040 A2 | 12/2002 |
| WO | WO 2002102235 A2 | 12/2002 |
| WO | WO 2003003906 A2 | 1/2003 |
| WO | WO 2003008444 A2 | 1/2003 |
| WO | WO 2003024392 A2 | 3/2003 |
| WO | WO 2003042661 A2 | 5/2003 |
| WO | WO 2004005458 A2 | 1/2004 |
| WO | WO 2004010957 A2 | 2/2004 |
| WO | WO 2004016799 A2 | 2/2004 |
| WO | WO 2004065545 A2 | 8/2004 |
| WO | WO 2005030124 A2 | 4/2005 |
| WO | WO 2005111076 A1 | 11/2005 |
| WO | WO 2008052187 A2 | 5/2008 |
| WO | WO 2008052187 A3 | 5/2008 |
| WO | WO 2006105488 A2 | 10/2016 |
| WO | WO 2006105488 A3 | 10/2016 |

OTHER PUBLICATIONS

Brancati et al., "Mutations in PVRL4, Encoding Cell Adhesion Molecule Nectin-4, Cause Ectodermal Dysplasia-Syndactyly Syndrome," The American Journal of Human Genetics (2010) 87:265-273.

Carter et al., 2008, "Antibody-drug conjugates for cancer therapy," Cancer J., 14(3):154-169.

Doronina et al., 2006, "Enhanced activity of monomethylauristatin F through monoclonal antibody delivery: effects of linker technology on efficacy and toxicity," Bioconjug Chem., 17(1):114-124.

Fabre et al., "Prominent role of the Ig-like V domain in trans-interactions of nectins. Nectin3 and nectin 4 bind to the predicted C—C'—C"—D beta-strands of the nectin1 V domain," The Journal of Biological Chemistry (2002) 277(30):27006-27013.

Fabre-Lafay et al., "Nectin-4 is a new histological and serological tumor associated marker for breast cancer," BMC Cancer (2007) 7:73.

Fabre-Lafay et al., "Nectin-4, a new serological breast cancer marker, is a substrate for tumor necrosis factor-alpha-converting enzyme (TACE)/ADAM-17," The Journal of Biological Chemistry (2005) 280(20):19543-19550.

Fu et al., "Translational regulation of human p53 gene expression," EMBO Journal (1996) 15:4392-4401.

Greenbaum et al., "Comparing protein abundance and mRNA expression levels on a genomic scale," Genome Biology (2003) 4(9):117.1-117.8.

Hacker, "Lack of association between an interleukin-1 receptor antagonist gene polymorphism and ulcerative colitis," Gut (1997) 40:623-627.

Kroese et al., "Genetic tests and their evaluation: Can we answer the key questions?" Genetics in Medicine (2004) 6:475-480.

Lucentini, "Gene Association Studies Typically Wrong," The Scientist (2004) 18:20.

Mallampalli et al., "Betamethasone modulation of sphingomyelin hydrolysis up-regulates CTP: cholinephosphate cytidylyltransferase activity in adult rat lung," Biochem. J. (1996) 38:333-341.

Martin, 2010, "Chapter 3: Protein Sequence and Structure Analysis of Antibody Variable Domains," R. Kontermann and S. Dubel (eds.), Antibody Engineering vol. 2, Springer-Verlag Berlin Heidelberg, pp. 33-51.

Pennisi, "A Closer Look at SNPs Suggests Difficulties," Science (1998) 281 (5384):1787-1789.

Reymond et al., "Nectin4/PRR4, a New Afadin-associated Member of the Nectin Family that Trans-interacts with Nectin1/PRR1 through V Domain Interaction," J. Biol. Chem. (2001) 276(46):43205-43215.

Saffran et al., "Anti-PSCA mAbs inhibit tumor growth and metastasis formation and prolong the survival of mice bearing human prostate cancer xenografts," PNAS (2001) 98(5):2658-2663.

Senter, 2009, "Potent antibody drug conjugates for cancer therapy," Curr Opin Chem Biol., 13(3):235-244.

Takano et al., "Identification of Nectin-4 Oncoprotein as a Diagnostic and Therapeutic Target for Luna Cancer," Cancer Res. (2009) 69(16):6694-6703.

Zhao and Lu, "A germline knowledge based computational approach for determining antibody complementarity determining regions," Molecular Immunology, (2010) 47:694-700.

Figure 1: The cDNA (SEQ ID NO:1) and amino acid sequence (SEQ ID NO:2) of 191P4D12. The start methionine is underlined. The open reading frame extends from nucleic acid 264-1796 including the stop codon.

```
  1 ggccgtcgttgttggccacagcgtgggaagcagctctgggggagctcggagctcccgatc
 61 acggcttcttgggggtagctacggctgggtgtgtagaacggggccggggctggggctggg
121 tccctagtggagacccaagtgcgagaggcaagaactctgcagcttcctgccttctggt
181 cagttccttattcaagtctgcagccggctcccagggagatctcggtggaacttcagaaac
  1                                    M  P  L  S  L  G  A  E  M  W  G  P  E
241 gctgggcagtctgcctttcaaccATGCCCCTGTCCCTGGGAGCCGAGATGTGGGGGCCTG
 14  A  W  L  L  L  L  L  A  S  F  T  G  R  C  P  A  G  E
301 AGGCCTGGCTGCTGCTGCTGCTACTGCTGGCATCATTTACAGGCCGGTGCCCCGCGGGTG
 34  L  E  T  S  D  V  V  T  V  V  L  G  Q  D  A  K  L  P  C  F
361 AGCTGGAGACCTCAGACGTGGTAACTGTGGTGCTGGGCCAGGACGCAAAACTGCCCTGCT
 54  Y  R  G  D  S  G  E  Q  V  G  Q  V  A  W  A  R  V  D  A  G
421 TCTACCGAGGGGACTCCGGCGAGCAAGTGGGGCAAGTGGCATGGGCTCGGGTGGACGCGG
 74  E  G  A  Q  E  L  A  L  L  H  S  K  Y  G  L  H  V  S  P  A
481 GCGAAGGCGCCCAGGAACTAGCGCTACTGCACTCCAAATACGGGCTTCATGTGAGCCCGG
 94  Y  E  G  R  V  E  Q  P  P  P  P  R  N  P  L  D  G  S  V  L
541 CTTACGAGGGCCGCGTGGAGCAGCCGCCGCCCCCACGCAACCCCCTGGACGGCTCAGTGC
114  L  R  N  A  V  Q  A  D  E  G  E  Y  E  C  R  V  S  T  F  P
601 TCCTGCGCAACGCAGTGCAGGCGGATGAGGGCGAGTACGAGTGCCGGGTCAGCACCTTCC
134  A  G  S  F  Q  A  R  L  R  L  R  V  L  V  P  P  L  P  S  L
661 CCGCCGGCAGCTTCCAGGCGCGGCTGCGGCTCCGAGTGCTGGTGCCTCCCCTGCCCTCAC
154  N  P  G  P  A  L  E  E  G  Q  G  L  T  L  A  A  S  C  T  A
721 TGAATCCTGGTCCAGCACTAGAAGAGGGCCAGGGCCTGACCCTGGCAGCCTCCTGCACAG
174  E  G  S  P  A  P  S  V  T  W  D  T  E  V  K  G  T  T  S  S
781 CTGAGGGCAGCCCAGCCCCCAGCGTGACCTGGGACACGGAGGTCAAAGGCACAACGTCCA
194  R  S  F  K  H  S  R  S  A  A  V  T  S  E  F  H  L  V  P  S
841 GCCGTTCCTTCAAGCACTCCCGCTCTGCTGCCGTCACCTCAGAGTTCCACTTGGTGCCTA
214  R  S  M  N  G  Q  P  L  T  C  V  V  S  H  P  G  L  L  Q  D
901 GCCGCAGCATGAATGGGCAGCCACTGACTTGTGTGGTGTCCCATCCTGGCCTGCTCCAGG
234  Q  R  I  T  H  I  L  H  V  S  F  L  A  E  A  S  V  R  G  L
961 ACCAAAGGATCACCCACATCCTCCACGTGTCCTTCCTTGCTGAGGCCTCTGTGAGGGGCC
254  E  D  Q  N  L  W  H  I  G  R  E  G  A  M  L  K  C  L  S  E
1021 TTGAAGACCAAAATCTGTGGCACATTGGCAGAGAAGGAGCTATGCTCAAGTGCCTGAGTG
274  G  Q  P  P  P  S  Y  N  W  T  R  L  D  G  P  L  P  S  G  V
1081 AAGGGCAGCCCCCTCCCTCATACAACTGGACACGGCTGGATGGGCCTCTGCCCAGTGGGG
294  R  V  D  G  D  T  L  G  F  P  P  L  T  T  E  H  S  G  I  Y
1141 TACGAGTGGATGGGGACACTTTGGGCTTTCCCCCACTGACCACTGAGCACAGCGGCATCT
314  V  C  H  V  S  N  E  F  S  S  R  D  S  Q  V  T  V  D  V  L
1201 ACGTCTGCCATGTCAGCAATGAGTTCTCCTCAAGGGATTCTCAGGTCACTGTGGATGTTC
334  D  P  Q  E  D  S  G  K  Q  V  D  L  V  S  A  S  V  V  V
```

```
1261 TTGACCCCCAGGAAGACTCTGGGAAGCAGGTGGACCTAGTGTCAGCCTCGGTGGTGGTGG
 354   G  V  I  A  A  L  L  F  C  L  L  V  V  V  V  L  M  S  R
1321 TGGGTGTGATCGCCGCACTCTTGTTCTGCCTTCTGGTGGTGGTGGTGGTGCTCATGTCCC
 374   Y  H  R  R  K  A  Q  Q  M  T  Q  K  Y  E  E  E  L  T  L  T
1381 GATACCATCGGCGCAAGGCCCAGCAGATGACCCAGAAATATGAGGAGGAGCTGACCCTGA
 394   R  E  N  S  I  R  R  L  H  S  H  H  T  D  P  R  S  Q  P  E
1441 CCAGGGAGAACTCCATCCGGAGGCTGCATTCCCATCACACGGACCCCAGGAGCCAGCCGG
 414   E  S  V  G  L  R  A  E  G  H  P  D  S  L  K  D  N  S  S  C
1501 AGGAGAGTGTAGGGCTGAGAGCCGAGGGCCACCCTGATAGTCTCAAGGACAACAGTAGCT
 434   S  V  M  S  E  E  P  E  G  R  S  Y  S  T  L  T  T  V  R  E
1561 GCTCTGTGATGAGTGAAGAGCCCGAGGGCCGCAGTTACTCCACGCTGACCACGGTGAGGG
 454   I  E  T  Q  T  E  L  L  S  P  G  S  G  R  A  E  E  E  E  D
1621 AGATAGAAACACAGACTGAACTGCTGTCTCCAGGCTCTGGGCGGGCCGAGGAGGAGGAAG
 474   Q  D  E  G  I  K  Q  A  M  N  H  F  V  Q  E  N  G  T  L  R
1681 ATCAGGATGAAGGCATCAAACAGGCCATGAACCATTTTGTTCAGGAGAATGGGACCCTAC
 494   A  K  P  T  G  N  G  I  Y  I  N  G  R  G  H  L  V  *
1741 GGGCCAAGCCCACGGGCAATGGCATCTACATCAATGGGCGGGGACACCTGGTCTGAccca
1801 ggcctgcctcccttccctaggcctggctccttctgttgacatgggagattttagctcatc
1861 ttggggcctccttaaacaccccatttcttgcggaagatgctccccatcccactgactg
1921 cttgacctttacctccaaccttctgttcatcgggagggctccaccaattgagtctctcc
1981 caccatgcatgcaggtcactgtgtgtgtgcatgtgtgcctgtgtgagtgttgactgactg
2041 tgtgtgtgtggaggggtgactgtccgtggagggggtgactgtgtccgtggtgtgtattatg
2101 ctgtcatatcagagtcaagtgaactgtggtgtatgtgccacgggatttgagtggttgcgt
2161 gggcaacactgtcagggtttggcgtgtgtgtcatgtggctgtgtgtgacctctgcctgaa
2221 aaagcaggtatttctcagacccagagcagtattaatgatgcagaggttggaggagaga
2281 ggtggagactgtggctcagacccaggtgtgcgggcatagctggagctggaatctgcctcc
2341 ggtgtgagggaacctgtctcctaccacttcggagccatgggggcaagtgtgaagcagcca
2401 gtccctgggtcagccagaggcttgaactgttacagaagccctctgccctctggtggcctc
2461 tgggcctgctgcatgtacatatttctgtaaatatacatgcgccgggagcttcttgcagg
2521 aatactgctccgaatcacttttaattttttttctttttttttttcttgccctttccattagt
2581 tgtattttttatttattttttattttttatttttttttagagatggagtctcactatgttgc
2641 tcaggctggccttgaactcctgggctcaagcaatcctcctgcctcagcctccctagtagc
2701 tgggactttaagtgtacaccactgtgcctgctttgaatcctttacgaagagaaaaaaaaa
2761 attaaagaaagcctttagatttatccaatgtttactactgggattgcttaaagtgaggcc
2821 cctccaacaccaggggttaattcctgtgattgtgaaaggggctacttccaaggcatctt
2881 catgcaggcagcccttgggagggcacctgagagctggtagagtctgaaattagggatgt
2941 gagcctcgtggttactgagtaaggtaaaattgcatccaccattgtttgtgataccttagg
3001 gaattgcttggacctggtgacaagggctcctgttcaatagtggtgttggggagagagaga
3061 gcagtgattatagaccgagagagtaggagttgaggtgaggtgaaggaggtgctgggggtg
3121 agaatgtcgcctttccccctgggttttggatcactaattcaaggctcttctggatgtttc
3181 tctgggttggggctggagttcaatgaggtttattttttagctggcccacccagatacactc
3241 agccagaatacctagatttagtacccaaactcttcttagtctgaaatctgctggatttct
3301 ggcctaagggagaggctcccatccttcgttccccagccagcctaggacttcgaatgtgga
3361 gcctgaagatctaagatcctaacatgtacatttttatgtaaatatgtgcatatttgtacat
3421 aaaatgatattctgttttttaaataaacagacaaaaacttgaaaaa
```

Figure 1 (Continued)

Figure 2A: The cDNA (SEQ ID NO:3) and amino acid sequence (SEQ ID NO:4) of Ha22-2(2,4)6.1 heavy chain. Double-underlined is the leader sequence, underlined is the heavy chain variable region, and underlined with a dashed line is the human IgG1 constant region.

```
                                         M  E  L  G  L  C  W  V  F  L  V  A  I  L  E
   1  GGTGATCAGCACTGAACACAGAGGACTCACCATGGAGTTGGGGCTGTGCTGGGTTTTCCTTGTTGCTATTTTAGA
       G  V  Q  C  E  V  Q  L  V  E  S  G  G  G  L  V  Q  P  G  G  S  L  R  L  S
  76  AGGTGTCCAGTGTGAGGTGCAGCTGGTGGAGTCTGGGGGAGGCTTGGTACAGCCTGGGGGGTCCCTGAGACTCTC
       C  A  A  S  G  F  T  F  S  S  Y  N  M  N  W  V  R  Q  A  P  G  K  G  L  E
 151  CTGTGCAGCCTCTGGATTCACCTTCAGTAGCTATAACATGAACTGGGTCCGCCAGGCTCCAGGGAAGGGGCTGGA
       W  V  S  Y  I  S  S  S  S  S  T  I  Y  Y  A  D  S  V  K  G  R  F  T  I  S
 226  GTGGGTTTCATACATTAGTAGTAGTAGTAGTACCATATACTACGCAGACTCTGTGAAGGGCCGATTCACCATCTC
       R  D  N  A  K  N  S  L  S  L  Q  M  N  S  L  R  D  E  D  T  A  V  Y  Y  C
 301  CAGAGACAATGCCAAGAACTCACTGTCTCTGCAAATGAACAGCCTGAGAGACGAGGACACGGCTGTGTATTACTG
       A  R  A  Y  Y  Y  G  M  D  V  W  G  Q  G  T  T  V  T  V  S  S  A  S  T  K
 376  TGCGAGAGCATACTACTACGGTATGGACGTCTGGGGCCAAGGGACCACGGTCACCGTCTCCTCAGCCTCCACCAA
       G  P  S  V  F  P  L  A  P  S  S  K  S  T  S  G  G  T  A  A  L  G  C  L  V
 451  GGGCCCATCGGTCTTCCCCCTGGCACCCTCCTCCAAGAGCACCTCTGGGGGCACAGCGGCCCTGGGCTGCCTGGT
       K  D  Y  F  P  E  P  V  T  V  S  W  N  S  G  A  L  T  S  G  V  H  T  F  P
 526  CAAGGACTACTTCCCCGAACCGGTGACGGTGTCGTGGAACTCAGGCGCCCTGACCAGCGGCGTGCACACCTTCCC
       A  V  L  Q  S  S  G  L  Y  S  L  S  S  V  V  T  V  P  S  S  L  G  T  Q
 601  GGCTGTCCTACAGTCCTCAGGACTCTACTCCCTCAGCAGCGTGGTGACCGTGCCCTCCAGCAGCTTGGGCACCCA
       T  Y  I  C  N  V  N  H  K  P  S  N  T  K  V  D  K  R  V  E  P  K  S  C  D
 676  GACCTACATCTGCAACGTGAATCACAAGCCCAGCAACACCAAGGTGGACAAGAGAGTTGAGCCCAAATCTTGTGA
       K  T  H  T  C  P  P  C  P  A  P  E  L  L  G  G  P  S  V  F  L  F  P  P  K
 751  CAAAACTCACACATGCCCACCGTGCCCAGCACCTGAACTCCTGGGGGGACCGTCAGTCTTCCTCTTCCCCCCAAA
       P  K  D  T  L  M  I  S  R  T  P  E  V  T  C  V  V  V  D  V  S  H  E  D  P
 826  ACCCAAGGACACCCTCATGATCTCCCGGACCCCTGAGGTCACATGCGTGGTGGTGGACGTGAGCCACGAAGACCC
       E  V  K  F  N  W  Y  V  D  G  V  E  V  H  N  A  K  T  K  P  R  E  E  Q  Y
 901  TGAGGTCAAGTTCAACTGGTACGTGGACGGCGTGGAGGTGCATAATGCCAAGACAAAGCCGCGGGAGGAGCAGTA
       N  S  T  Y  R  V  V  S  V  L  T  V  L  H  Q  D  W  L  N  G  K  E  Y  K  C
 976  CAACAGCACGTACCGTGTGGTCAGCGTCCTCACCGTCCTGCACCAGGACTGGCTGAATGGCAAGGAGTACAAGTG
       K  V  S  N  K  A  L  P  A  P  I  E  K  T  I  S  K  A  K  G  Q  P  R  E  P
1051  CAAGGTCTCCAACAAAGCCCTCCCAGCCCCCATCGAGAAAACCATCTCCAAAGCCAAAGGGCAGCCCCGAGAACC
       Q  V  Y  T  L  P  P  S  R  E  E  M  T  K  N  Q  V  S  L  T  C  L  V  K  G
1126  ACAGGTGTACACCCTGCCCCCATCCCGGGAGGAGATGACCAAGAACCAGGTCAGCCTGACCTGCCTGGTCAAAGG
       F  Y  P  S  D  I  A  V  E  W  E  S  N  G  Q  P  E  N  N  Y  K  T  T  P  P
1201  CTTCTATCCCAGCGACATCGCCGTGGAGTGGGAGAGCAATGGGCAGCCGGAGAACAACTACAAGACCACGCCTCC
       V  L  D  S  D  G  S  F  F  L  Y  S  K  L  T  V  D  K  S  R  W  Q  Q  G  N
1276  CGTGCTGGACTCCGACGGCTCCTTCTTCCTCTATAGCAAGCTCACCGTGGACAAGAGCAGGTGGCAGCAGGGGAA
       V  F  S  C  S  V  M  H  E  A  L  H  N  H  Y  T  Q  K  S  L  S  L  S  P  G
1351  CGTCTTCTCATGCTCCGTGATGCATGAGGCTCTGCACAACCACTACACGCAGAAGAGCCTCTCCCTGTCCCCGGG
       K  *
1426  TAAATGA
```

Figure 2B: The cDNA (SEQ ID NO:5) and amino acid sequence (SEQ ID NO:6) of Ha22-2(2,4)6.1 light chain. Double-underlined is the leader sequence, underlined is the light chain variable region, and underlined with a dashed line is the human kappa constant region.

```
                                       M  D  M  R  V  P  A  Q  L  L  G  L  L  L  L  W  F
   1  AGTCAGACCCAGTCAGGACACAGCATGGACATGAGGGTCCCCGCTCAGCTCCTGGGGCTCCTGCTGCTCTGGTTC
       P  G  S  R  C  D  I  Q  M  T  Q  S  P  S  S  V  S  A  S  V  G  D  R  V  T
  76  CCAGGTTCCAGATGCGACATCCAGATGACCCAGTCTCCATCTTCCGTGTCTGCATCTGTTGGAGACAGAGTCACC
       I  T  C  R  A  S  Q  G  I  S  G  W  L  A  W  Y  Q  Q  K  P  G  K  A  P  K
 151  ATCACTTGTCGGGCGAGTCAGGGTATTAGCGGCTGGTTAGCCTGGTATCAGCAGAAACCAGGGAAAGCCCCTAAG
       F  L  I  Y  A  A  S  T  L  Q  S  G  V  P  S  R  F  S  G  S  G  S  G  T  D
 226  TTCCTGATCTATGCTGCATCCACTTTGCAAAGTGGGGTCCCATCAAGGTTCAGCGGCAGTGGATCTGGGACAGAT
       F  T  L  T  I  S  S  L  Q  P  E  D  F  A  T  Y  Y  C  Q  Q  A  N  S  F  P
 301  TTCACTCTCACCATCAGCAGCCTGCAGCCTGAAGATTTTGCAACTTACTATTGTCAACAGGCTAACAGTTTCCCT
       P  T  F  G  G  G  T  K  V  E  I  K  R  T  V  A  A  P  S  V  F  I  F  P  P
 376  CCCACTTTCGGCGGAGGGACCAAGGTGGAGATCAAACGTACGGTGGCTGCACCATCTGTCTTCATCTTCCCGCCA
       S  D  E  Q  L  K  S  G  T  A  S  V  V  C  L  L  N  N  F  Y  P  R  E  A  K
 451  TCTGATGAGCAGTTGAAATCTGGAACTGCCTCTGTTGTGTGCCTGCTGAATAACTTCTATCCCAGAGAGGCCAAA
       V  Q  W  K  V  D  N  A  L  Q  S  G  N  S  Q  E  S  V  T  E  Q  D  S  K  D
 526  GTACAGTGGAAGGTGGATAACGCCCTCCAATCGGGTAACTCCCAGGAGAGTGTCACAGAGCAGGACAGCAAGGAC
       S  T  Y  S  L  S  S  T  L  T  L  S  K  A  D  Y  E  K  H  K  V  Y  A  C  E
 601  AGCACCTACAGCCTCAGCAGCACCCTGACGCTGAGCAAAGCAGACTACGAGAAACACAAAGTCTACGCCTGCGAA
       V  T  H  Q  G  L  S  S  P  V  T  K  S  F  N  R  G  E  C  *
 676  GTCACCCATCAGGGCCTGAGCTCGCCCGTCACAAAGAGCTTCAACAGGGGAGAGTGTTAG
```

Figure 3A: The amino acid sequence (SEQ ID NO:7) of Ha22-2(2,4)6.1 heavy chain. Double-underlined is the leader sequence, underlined is the heavy chain variable region, and underlined with a dashed line is the human IgG1 constant region.

```
  1  MELGLCWVFLVAILEGVQCEVQLVESGGGLVQPGGSLRLSCAASGFTFSS
 51  YNMNWVRQAPGKGLEWVSYISSSSSTIYYADSVKGRFTISRDNAKNSLSL
101  QMNSLRDEDTAVYYCARAYYYGMDVWGQGTTVTVSSASTKGPSVFPLAPS
151  SKSTSGGTAALGCLVKDYFPEPVTVSWNSGALTSGVHTFPAVLQSSGLYS
201  LSSVVTVPSSSLGTQTYICNVNHKPSNTKVDKRVEPKSCDKTHTCPPCPA
251  PELLGGPSVFLFPPKPKDTLMISRTPEVTCVVVDVSHEDPEVKFNWYVDG
301  VEVHNAKTKPREEQYNSTYRVVSVLTVLHQDWLNGKEYKCKVSNKALPAP
351  IEKTISKAKGQPREPQVYTLPPSREEMTKNQVSLTCLVKGFYPSDIAVEW
401  ESNGQPENNYKTTPPVLDSDGSFFLYSKLTVDKSRWQQGNVFSCSVMHEA
451  LHNHYTQKSLSLSPGK
```

Figure 3B: The amino acid sequence (SEQ ID NO:8) of Ha22-2(2,4)6.1 light chain. Double-underlined is the leader sequence, underlined is the light chain variable region, and underlined with a dashed line is the human kappa constant region.

```
  1  MDMRVPAQLLGLLLLWFPGSRCDIQMTQSPSSVSASVGDRVTITCRASQG
 51  ISGWLAWYQQKPGKAPKFLIYAASTLQSGVPSRFSGSGSGTDFTLTISSL
101  QPEDFATYYCQQANSFPPTFGGGTKVEIKRTVAAPSVFIFPPSDEQLKSG
151  TASVVCLLNNFYPREAKVQWKVDNALQSGNSQESVTEQDSKDSTYSLSST
201  LTLSKADYEKHKVYACEVTHQGLSSPVTKSFNRGEC
```

Figure 4A: Alignment of Ha22-2(2,4)6.1 heavy chain (a portion of SEQ ID NOS:3, 4) to human Ig germline VH3-48 (SEQ ID NO:9).

```
ID%                                         <----------------------FWR1------------------------
                 2(2,4)6.1          89       E  V  Q  L  V  E  S  G  G  G  L  V  Q  P  G  G  S  L  R  L  S  C  A
                                             GAGGTGCAGCTGGTGGAGTCTGGGGGAGGCTTGGTACAGCCTGGGGGGTCCCTGAGACTCTCCTGTGCAG  158
99.3(293/295)    VH3-48              1       E  V  Q  L  V  E  S  G  G  G  L  V  Q  P  G  G  S  L  R  L  S  C  A
100(6/6)         D2-21                       .................................................................... 70
98.2(54/55)      JH6

ID%                                          <---------------> <-------CDR1------->           <------FWR2-------
                 2(2,4)6.1         159       CCTCT  GGATTCACCTTCAGTAGCTATAAC ATGAACTGGGTCCGCCAGGCTCCAGGGAAGGGCTGGAGTG  228
99.3(293/295)    VH3-48             71       A  S   G  F  T  F  S  S  Y  S  M  N  W  V  R  Q  A  P  G  K  G  L  E  W
100(6/6)         D2-21                       .....                      S...                                    .
98.2(54/55)      JH6                                                    G.

ID%                                          -----> <-----------CDR2----------->
                 2(2,4)6.1         229       GGTTTCATAC ATTAGTAGTAGTAGTAGTACCATA TACTACGCAGACTCTGTGAAGGGCCGATTCACCATC  298
99.3(293/295)    VH3-48            141       V  S  Y  I  S  S  S  S  S  S  T  I  Y  Y  A  D  S  V  K  G  R  F  T  I
100(6/6)         D2-21                       V  S  Y  I  S  S  S  S  S  S  T  I  Y  Y  A  D  S  V  K  G  R  F  T  I
98.2(54/55)      JH6                         .................................. 210

ID%                                          <----------FWR3----------
                 2(2,4)6.1         299       S  R  D  N  A  K  N  S  L  S  L  Q  M  N  S  L  R  D  E  D  T  A  V
                                             TCCAGAGACAATGCCAAGAACTCACTGTCTCTGCAAATGAACAGCCTGAGAGACGAGGACACGGCCGTGTGT  368
99.3(293/295)    VH3-48            211       S  R  D  N  A  K  N  S  L  Y  L  Q  M  N  S  L  R  D  E  D  T  A  V
100(6/6)         D2-21                       .........................Y......A...................................  280
98.2(54/55)      JH6
```

```
                                                    ----->
                                          Y  Y  C   A  R  A  Y  Y  Y  G  M  D  V  W  G  Q  G  T  T  V  T  V  S  S
                        2(2,4)6.1    369  ATTACTGT  GCGAGAGCATACTACTACGGTATGGACGTCTGGGGCCAAGGGACCACGGTCACCGTCTCCTC  438
99.3(293/295)  VH3-48   281          Y  Y  C       A  R  .  .  .  .  .  .  .  .  .  .  .  .  .  .  .  .  .  .  .  .  .  .  .  295
100(6/6)       D2-21      1                             A  R                                                              6
98.2(54/55)    JH6        9          ..........    .........................................G..........................  61
ID%
                        2(2,4)6.1    439  AG  440   GCGAGAGCATACTACTACGGTATGGACGTCTGGGGCCAAGGGACCACGGTCACCGTCTCCTC
99.3(293/295)  VH3-48    62          .........
100(6/6)       D2-21                 ..   63
98.2(54/55)    JH6
```

Figure 4A (Continued)

Figure 4B: Alignment of Ha22-2(2,4)6.1 light chain (a portion of SEQ ID NOS:5, 6) to human Ig germline L5 (SEQ ID NO:10).

```
ID%                    <------------------------FWR1------------------------>
             2(2,4)6.1  91  GACATCCAGATGACCCAGTCTCCATCTTCCGTGTCTGCATCTGTTGGAGACAGAGTCACCATCACTTGTC  160
                                 D  I  Q  M  T  Q  S  P  S  S  V  S  A  S  V  G  D  R  V  T  I  T  C
98.6(283/287) L5         1  ...................................................A...............   70
100(35/35)    JK4            D  I  Q  M  T  Q  S  P  S  S  V  S  A  S  V  G  D  R  V  T  I  T  C

ID%                                       <----CDR1---->                        <--------FWR2
             2(2,4)6.1 161  GGGCGAGT CAGGGTATTAGCGGCTGG TTAGCCTGGTATCAGCAGAAACCAGGGAAAGCCCCTAAGTTCCT  230
                             R  A  S   Q  G  I  S  G  W   L  A  W  Y  Q  Q  K  P  G  K  A  P  K  F  L
98.6(283/287) L5        71  ..............S.............A...................................L..L  140
100(35/35)    JK4            R  A  S   Q  G  I  S  W   L  A  W  Y  Q  Q  K  P  G  K  A  P  K  L  L

ID%                         <--CDR2-->                                                         F
             2(2,4)6.1 231  GATCTAT GCTGCATCC ACTTTGCAAAGTGGGGTCCCATCAAGGTTCAGTGGCAGTGGATCTGGGACAGAT  300
                             I  Y   A  A  S   T  L  Q  S  G  V  P  S  R  F  S  G  S  G  S  G  T  D
98.6(283/287) L5       141  ........S.........G.................................................  210
100(35/35)    JK4            I  Y   A  A  S   S  L  Q  S  G  V  P  S  R  F  S  G  S  G  S  G  T  D
                            -FWR3-->
             2(2,4)6.1 301  TTCACTCTCACCATCAGCAGCCTGCAGCCTGAAGATTTTGCAACTTACTATTGT CAACAGGCTAACAGTT  370
                             F  T  L  T  I  S  S  L  Q  P  E  D  F  A  T  Y  Y  C   Q  Q  A  N  S
98.6(283/287) L5       211  ....................................................  ...............  280
100(35/35)    JK4            F  T  L  T  I  S  S  L  Q  P  E  D  F  A  T  Y  Y  C   Q  Q  A  N  S

2(2,4)6.1 371  TCCCTCCCACTTTCGGCGGAGGGACCAAGGTGGAGATCAAAC  412
                             F  P  P  T  F  G  G  G  T  K  V  E  I  K
98.6(283/287) L5       281  ..........................................  287
100(35/35)    JK4        4  ..........................................   38
                             F  P  P
```

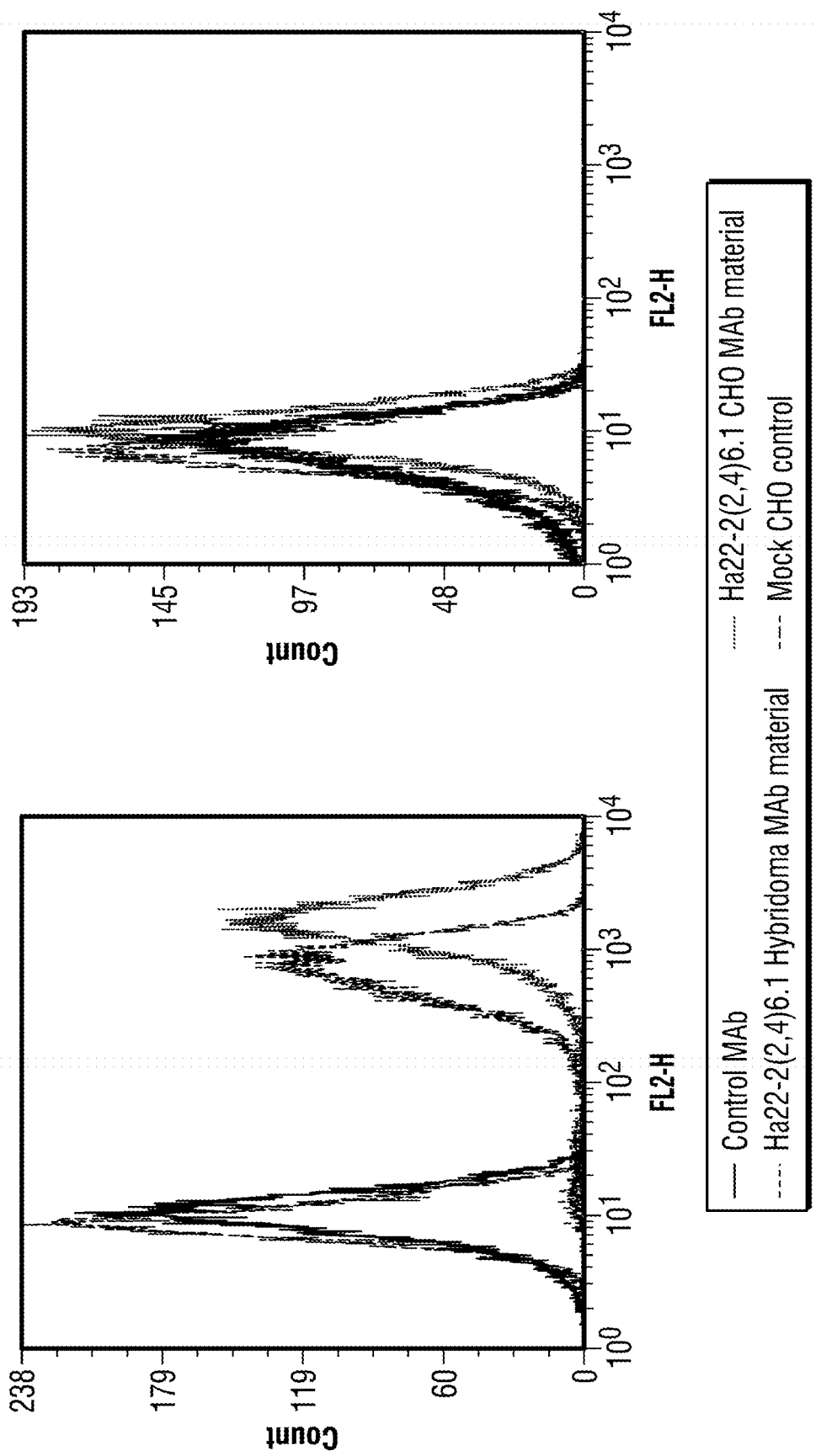
Figure 5A: Binding of Ha22-2(2,4)6.1 Mab using Flow Cytometry

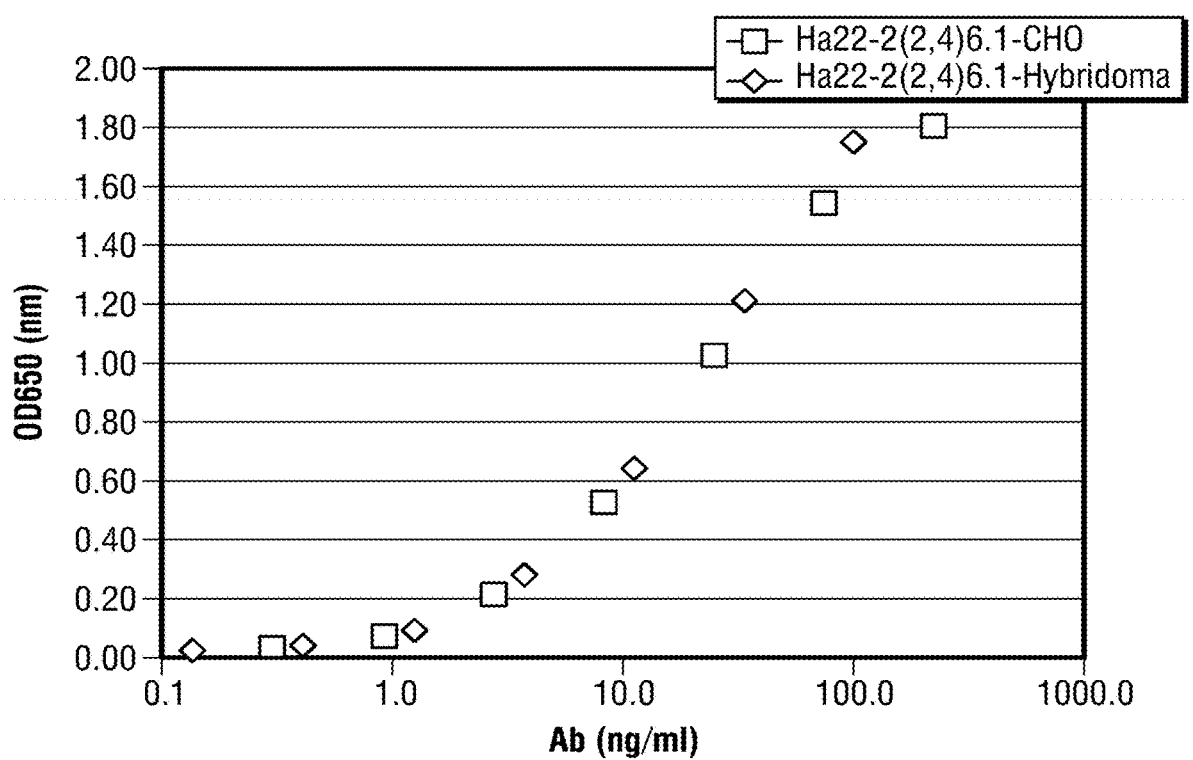
Figure 5B: Binding of Ha22-2(2,4)6.1 Mab using ELISA

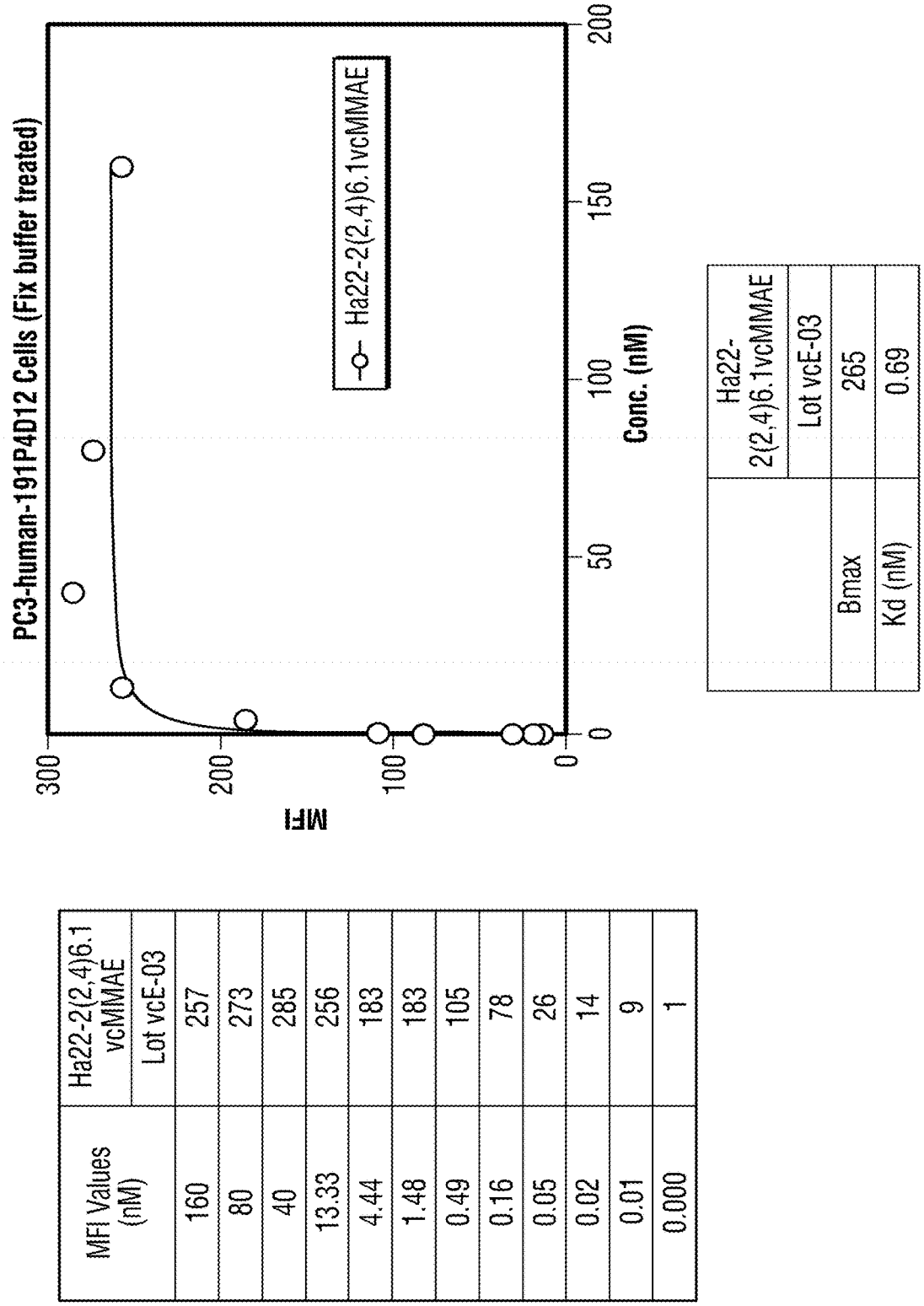
Figure 6: Ha22-2(2,4)6.1vcMMAE Affinity Determination by FACS using PC3-human-191P4D12

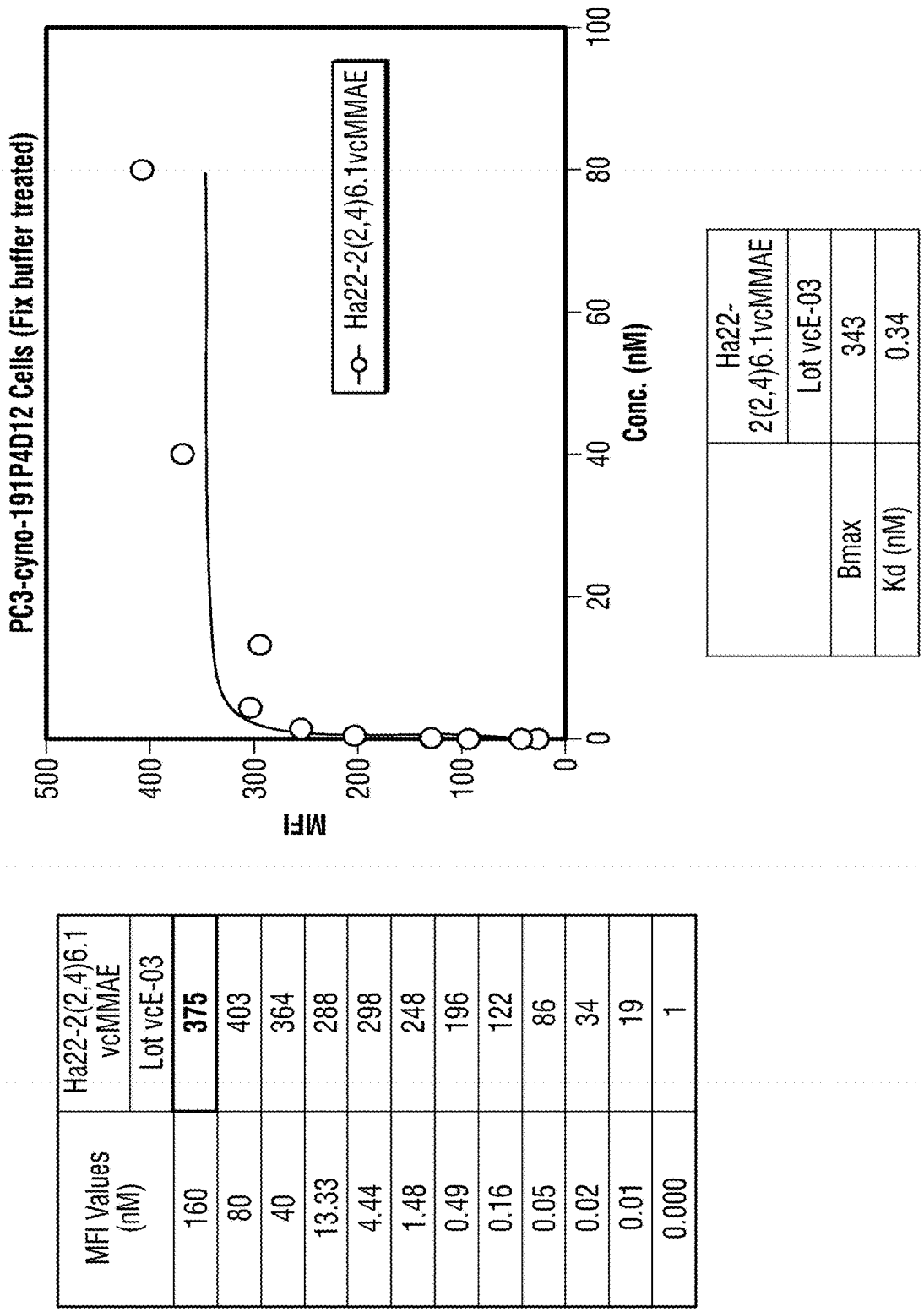
Figure 7: Ha22-2(2,4)6.1vcMMAE Affinity Determination by FACS using PC3-cynomolgus-191P4D12

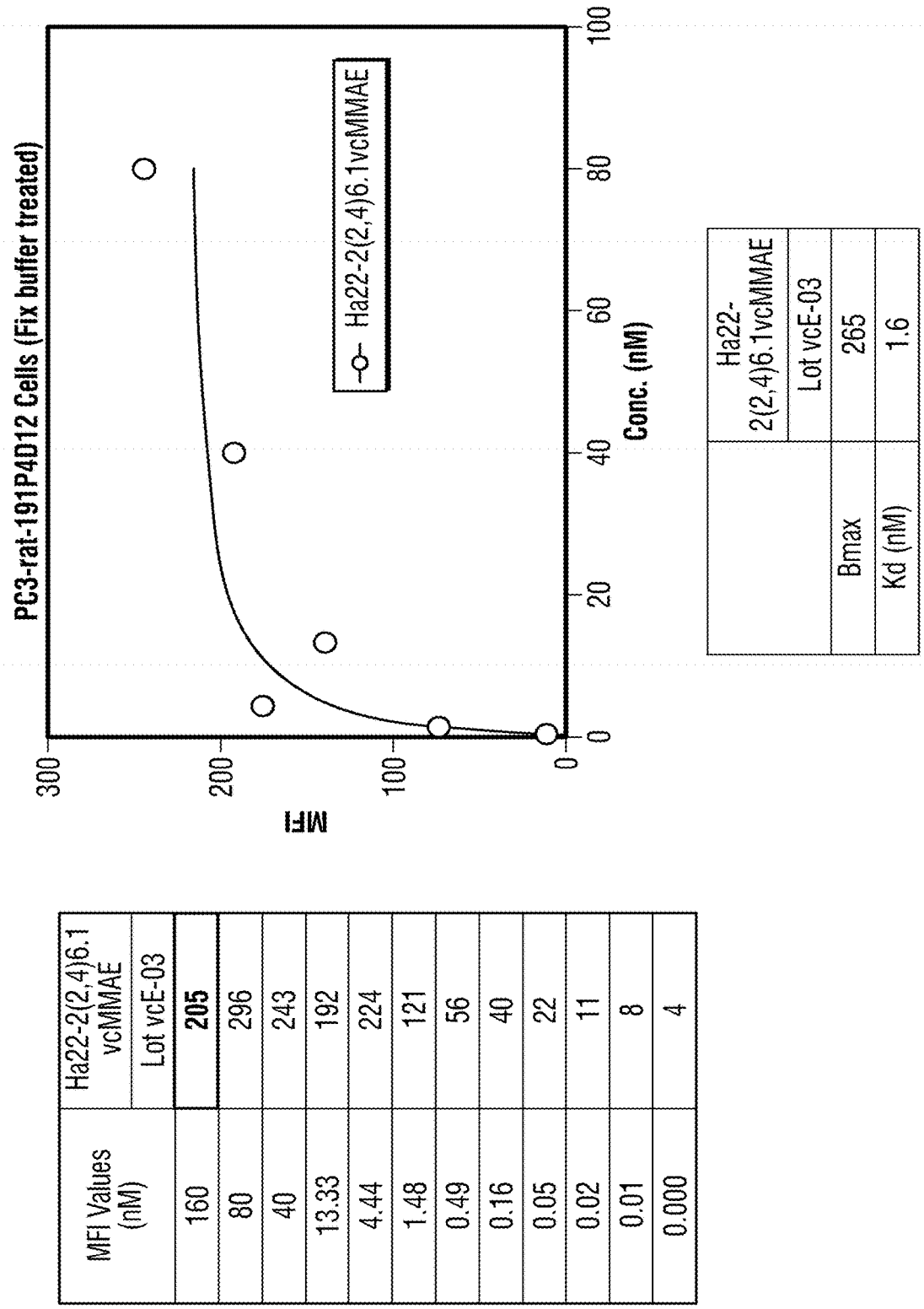
Figure 8: Ha22-2(2,4)6.1vcMMAE Affinity Determination by FACS using PC3-rat-191P4D12

Figure 9: Cell Cytotoxicity Mediated by Ha22-2(2,4)6.1vcMMAE

Figure 9: Cell Cytotoxicity Mediated by Ha22-2(2,4)6.1vcMMAE

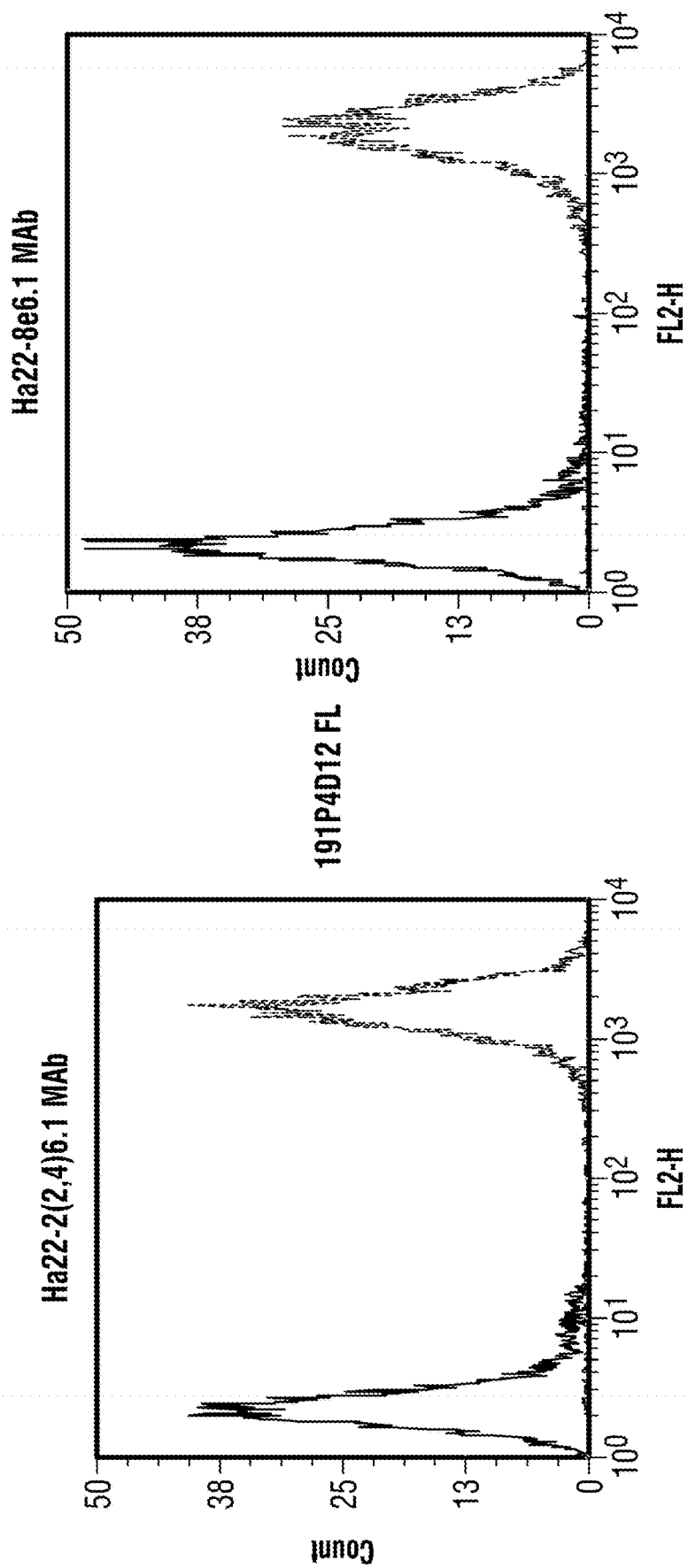
Figure 10: Domain Mapping of Ha22-(2,4)6.1 MAb by FACS

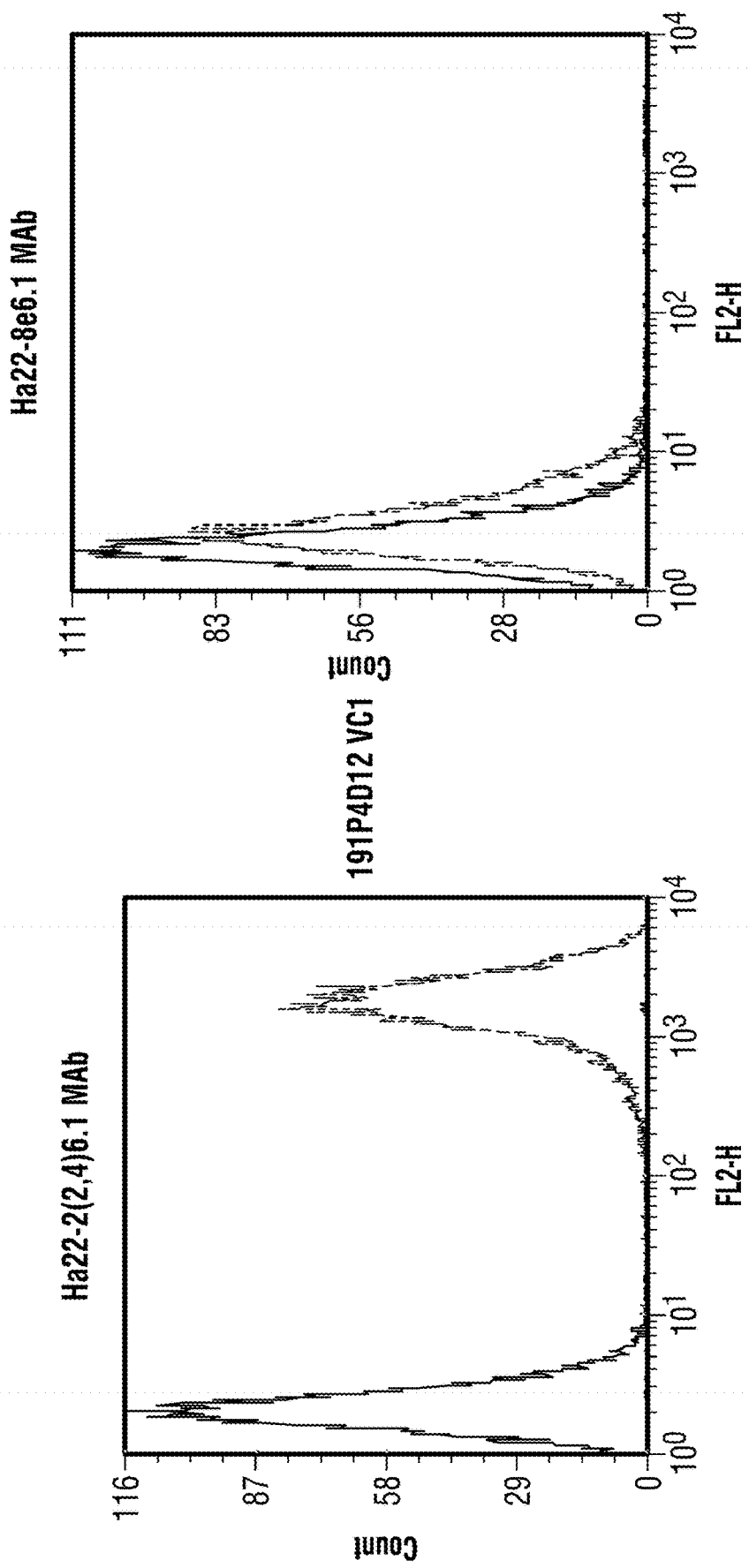

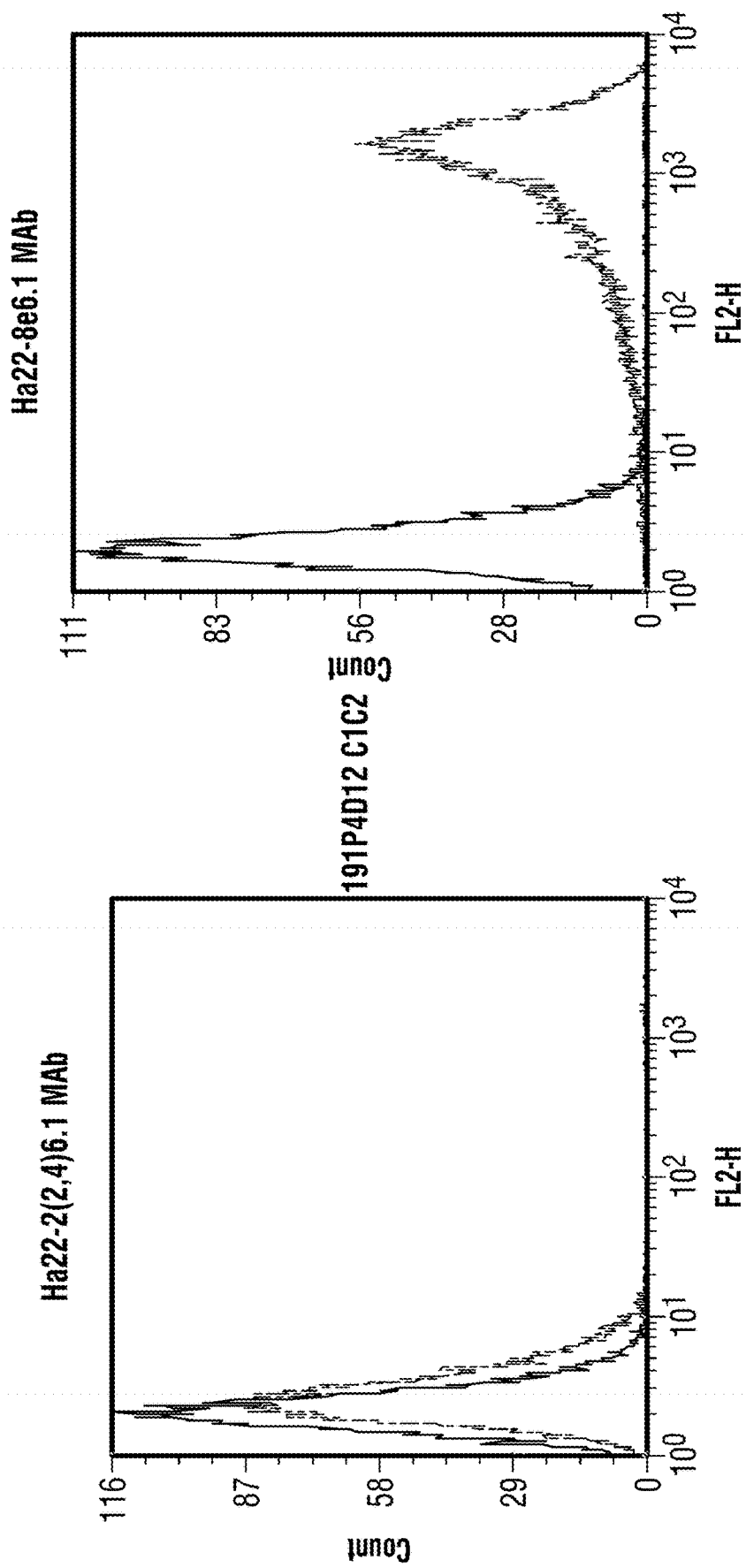
Figure 10 (Continued): Domain Mapping of Ha22-(2,4)6.1 MAb by FACS

Figure 11: Ha22-2(2,4)6 .1 MAb Domain Mapping by Western Blot Analysis.
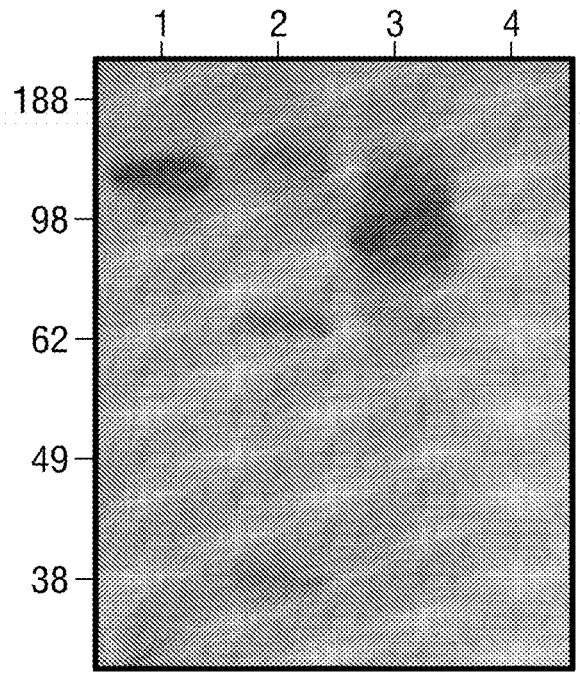
Probed with Ha22-2 (2,4)6.1-biotin and streptavidin-HRP
- 191P4D12 Full Length ECD, mFc Fusion
- 191P4D12 (aa 1-147, V Domain) mFc Fusion
- 191P4D12 (aa1-242, VC1 Domain) mFc Fusion
- 191P4D12 (aa1-31,147-346, C1C2 Domain) mFc Fusion
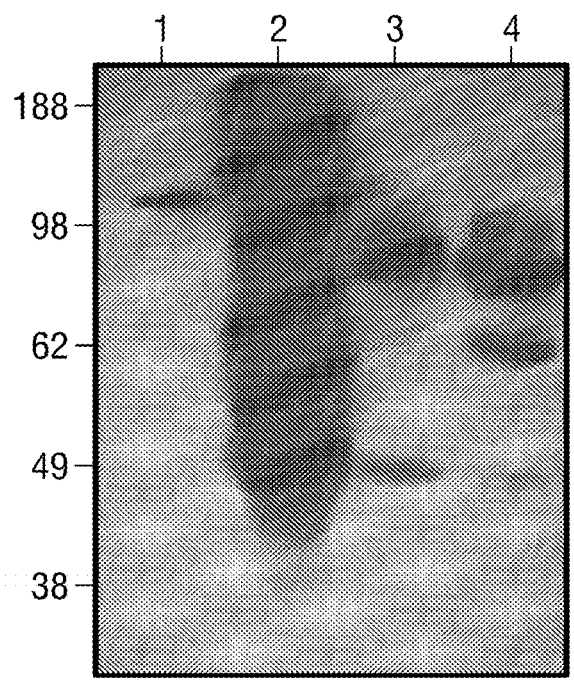
Probed with goat-anti-mouse HRP conjugate
- 191P4D12 Full Length ECD, mFc Fusion
- 191P4D12 (aa 1-147, V Domain) mFc Fusion
- 191P4D12 (aa1-242, VC1 Domain) mFc Fusion
- 191P4D12 (aa1-31,147-346, C1C2 Domain) mFc Fusion

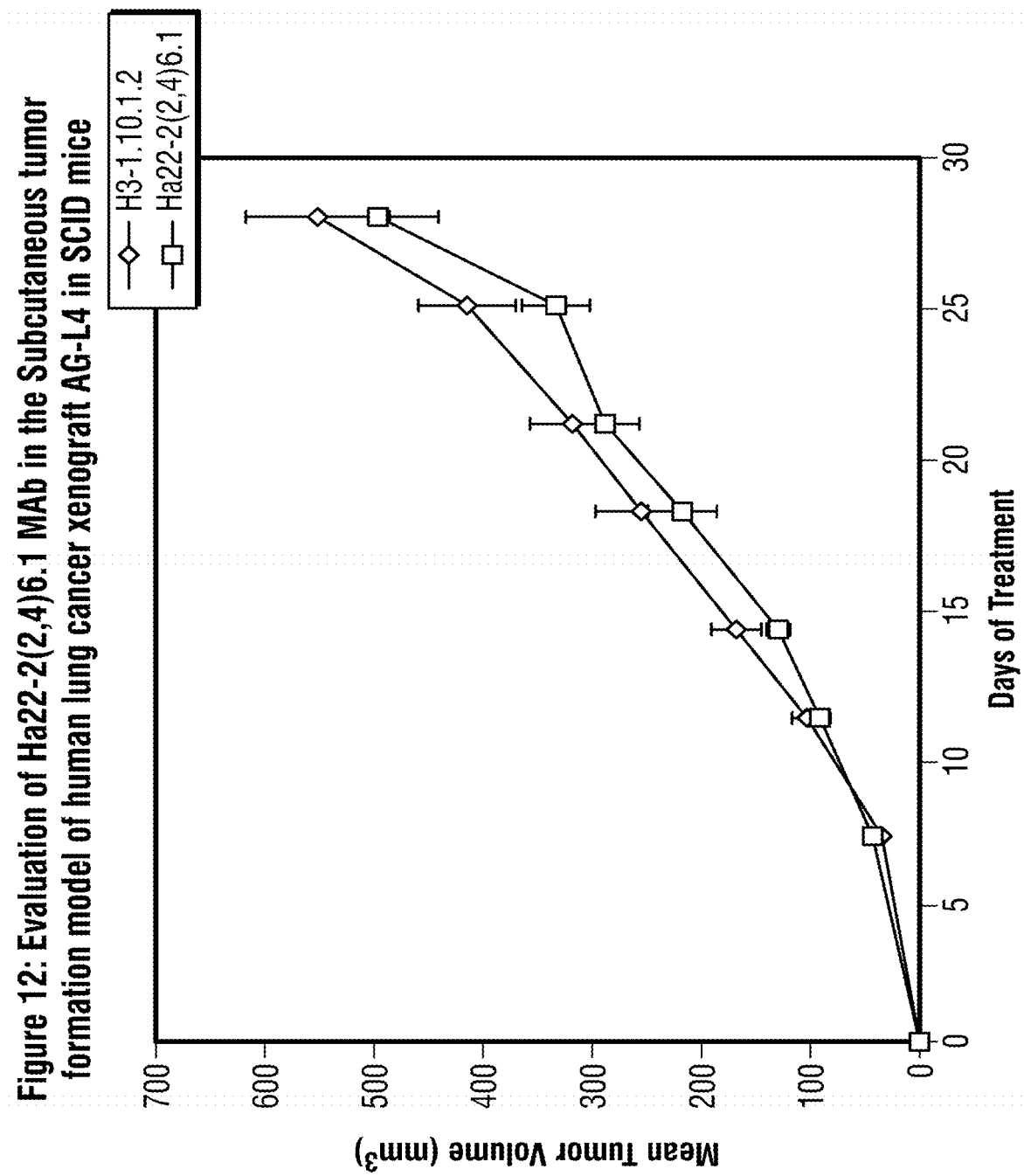
Figure 12: Evaluation of Ha22-2(2,4)6.1 MAb in the Subcutaneous tumor formation model of human lung cancer xenograft AG-L4 in SCID mice

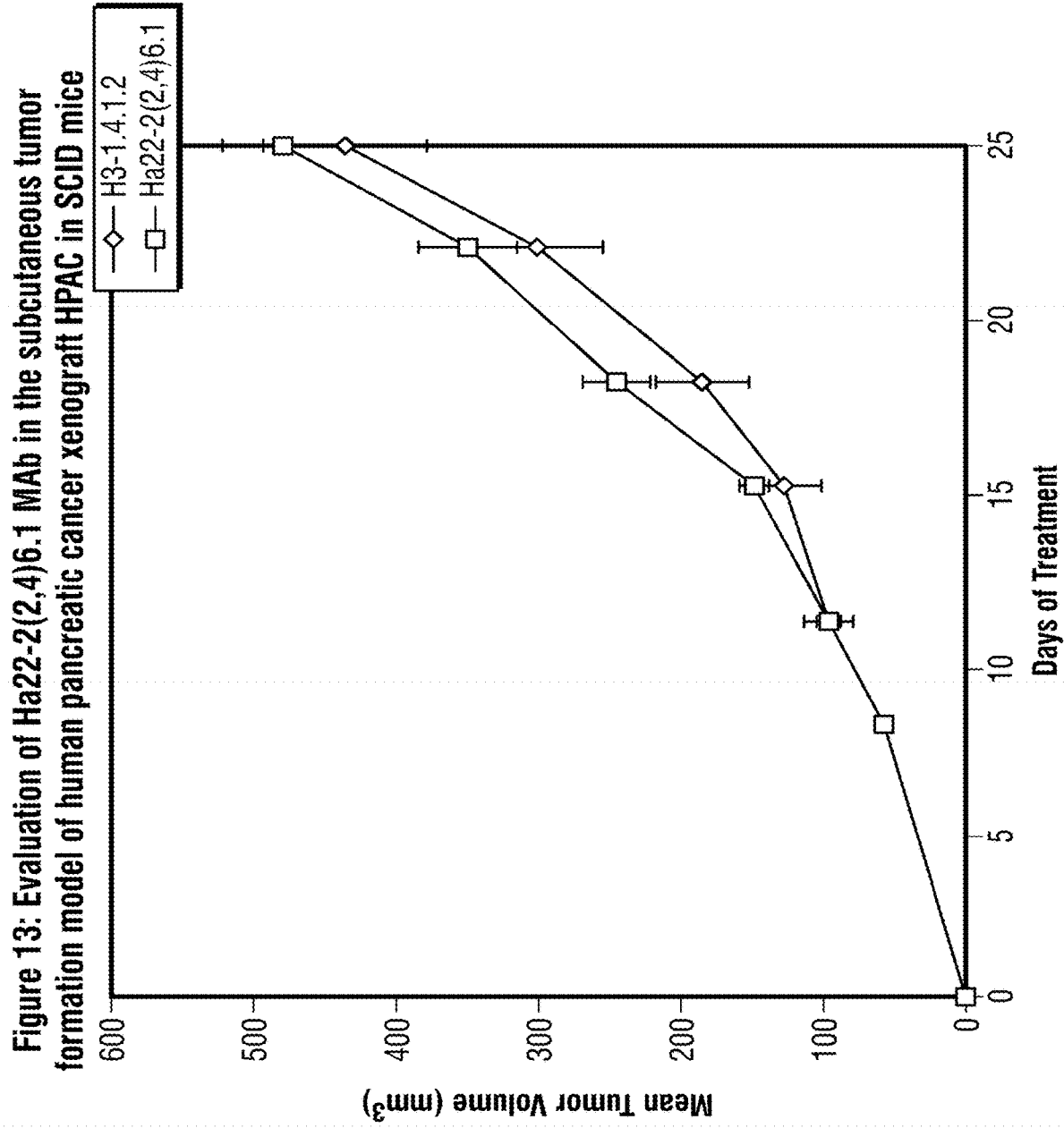
Figure 13: Evaluation of Ha22-2(2,4)6.1 MAb in the subcutaneous tumor formation model of human pancreatic cancer xenograft HPAC in SCID mice

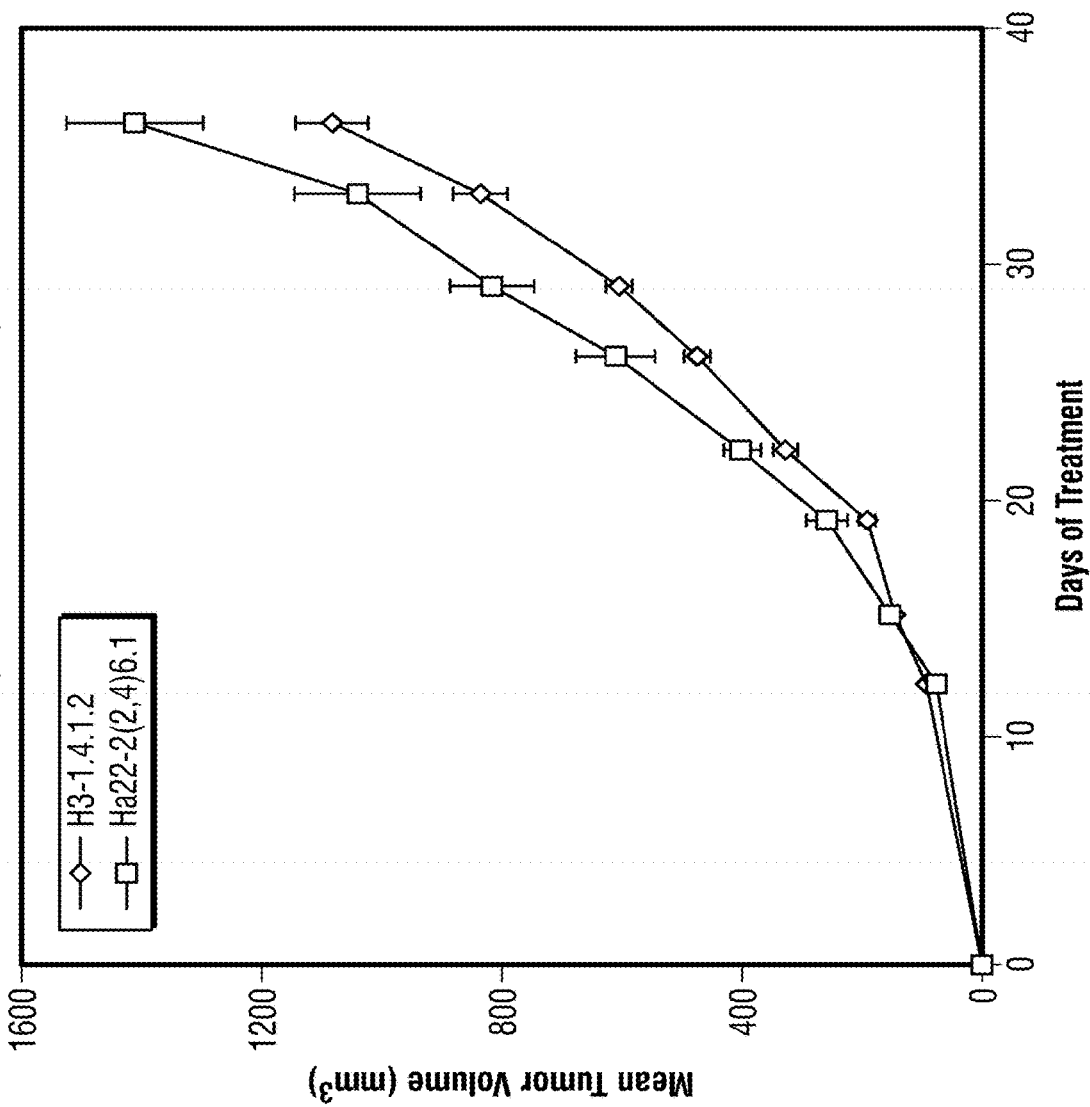
Figure 14: Evaluation of Ha22-2(2,4)6.1 MAb in the subcutaneous tumor formation model of human pancreatic cancer xenograft AG-Panc3 in SCID mice

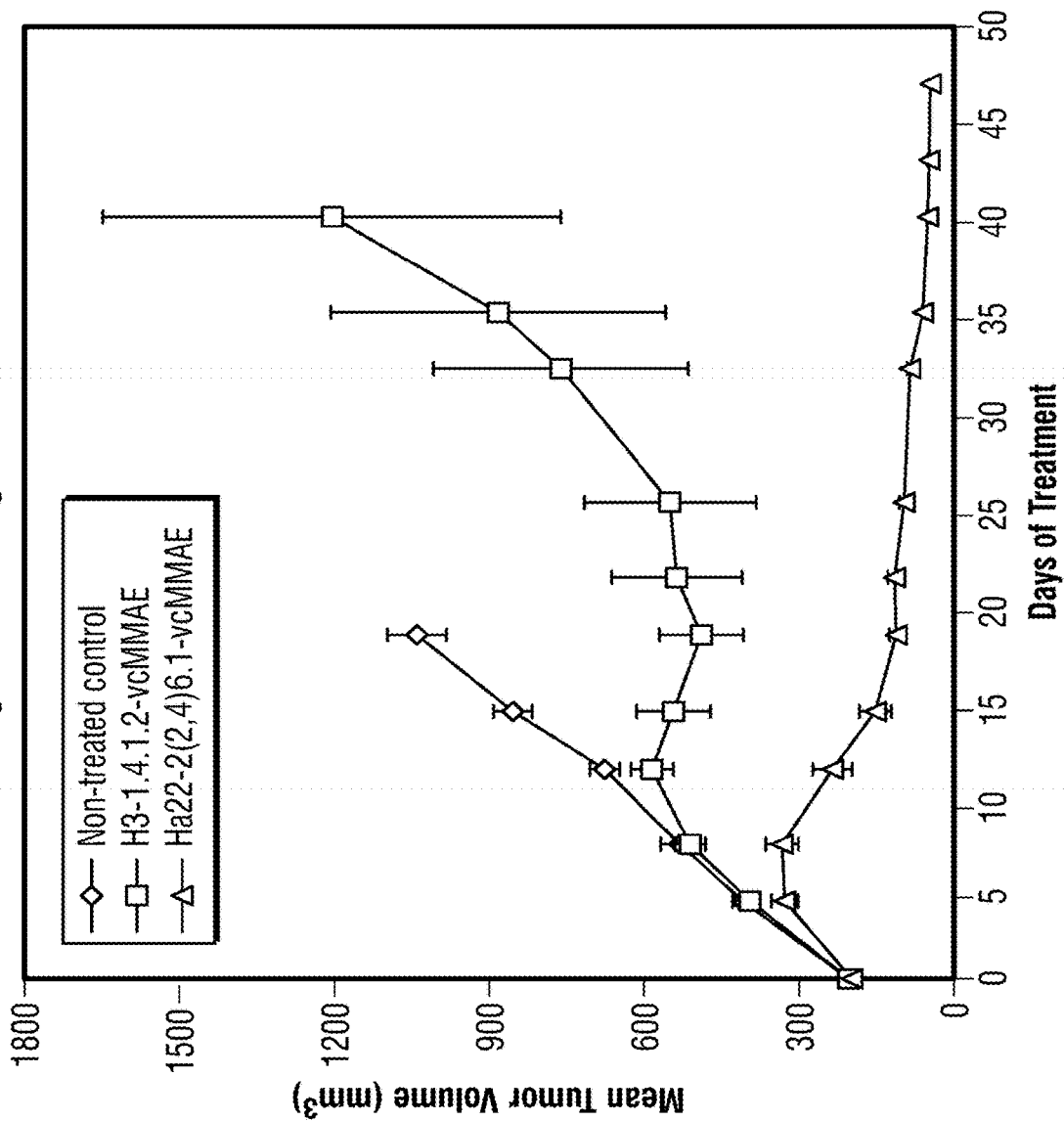

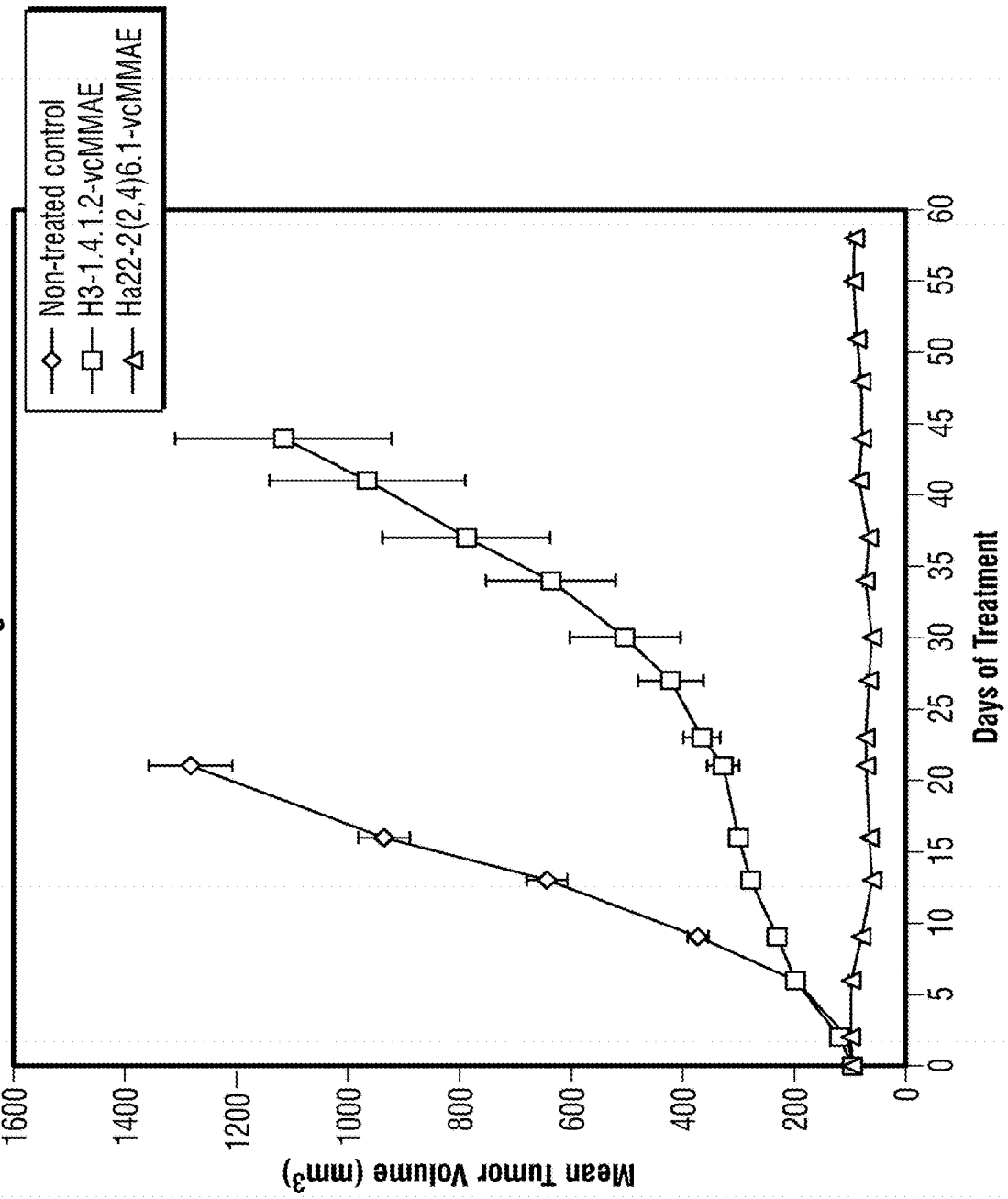

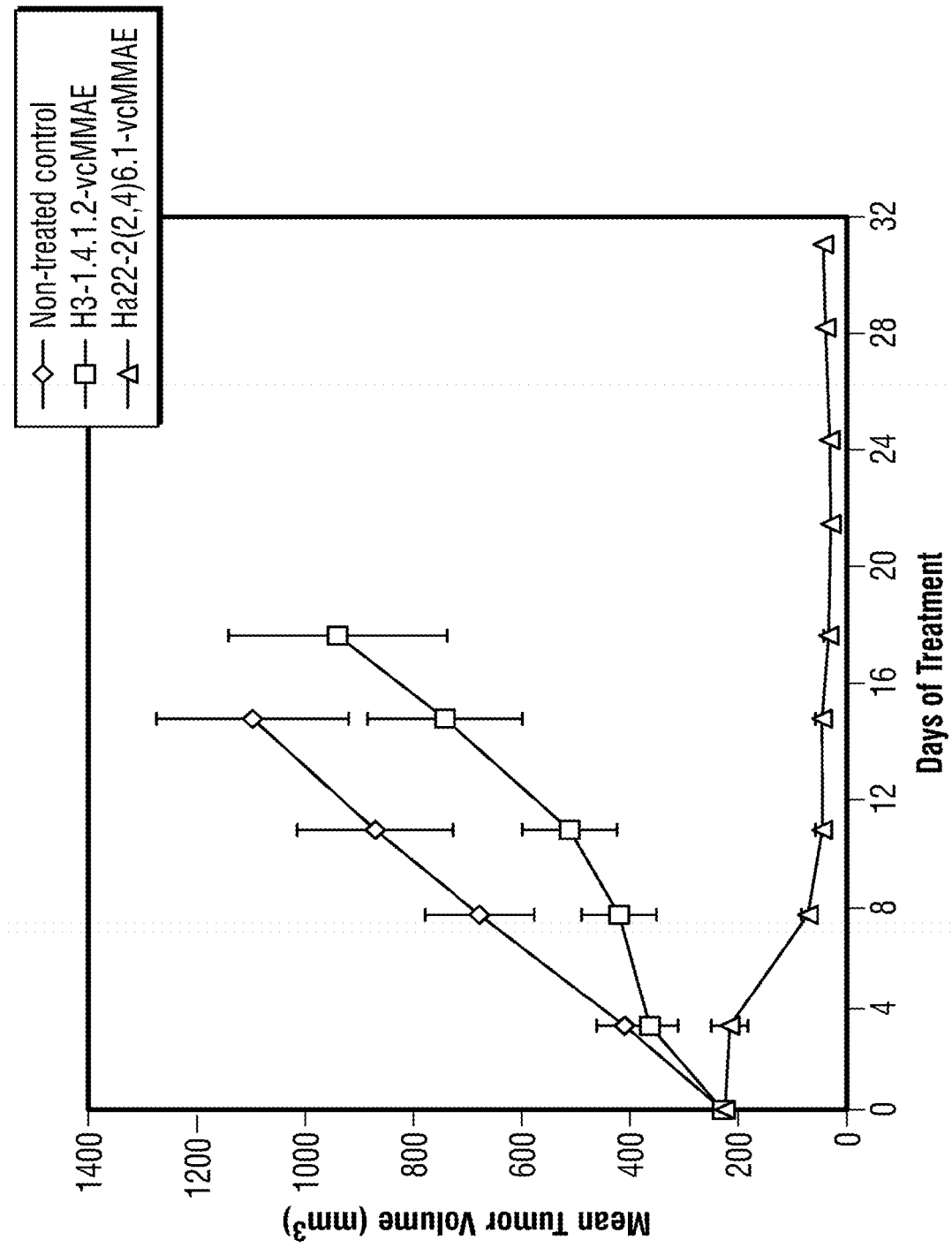
Figure 17: Efficacy of Ha22-2(2,4)6.1-vcMMAE in subcutaneous established human bladder cancer xenograft AG-B1 in SCID mice

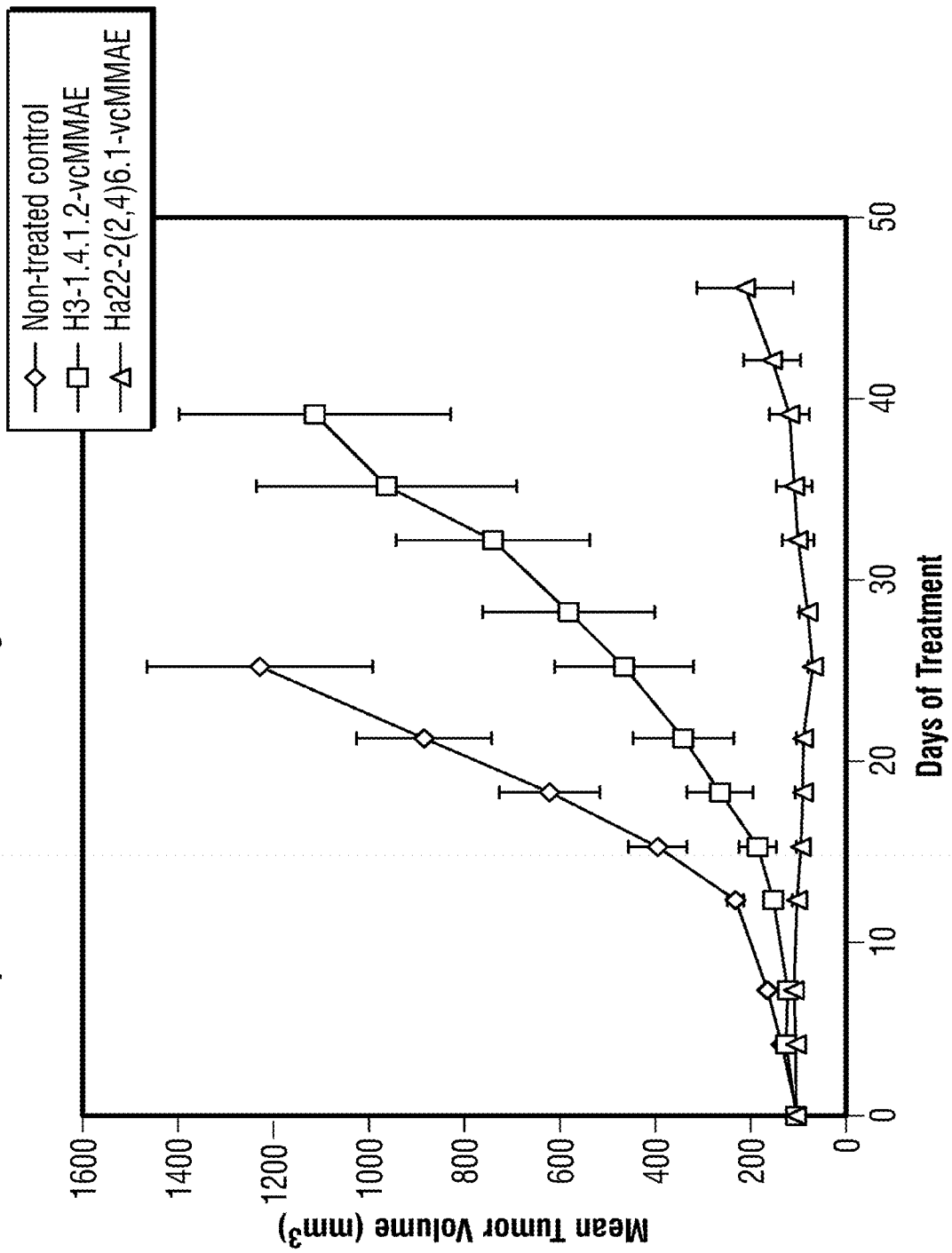
Figure 18: Efficacy of Ha22-2(2,4)6.1-vcMMAE in subcutaneous established human pancreatic cancer xenograft AG-Panc2 in SCID mice

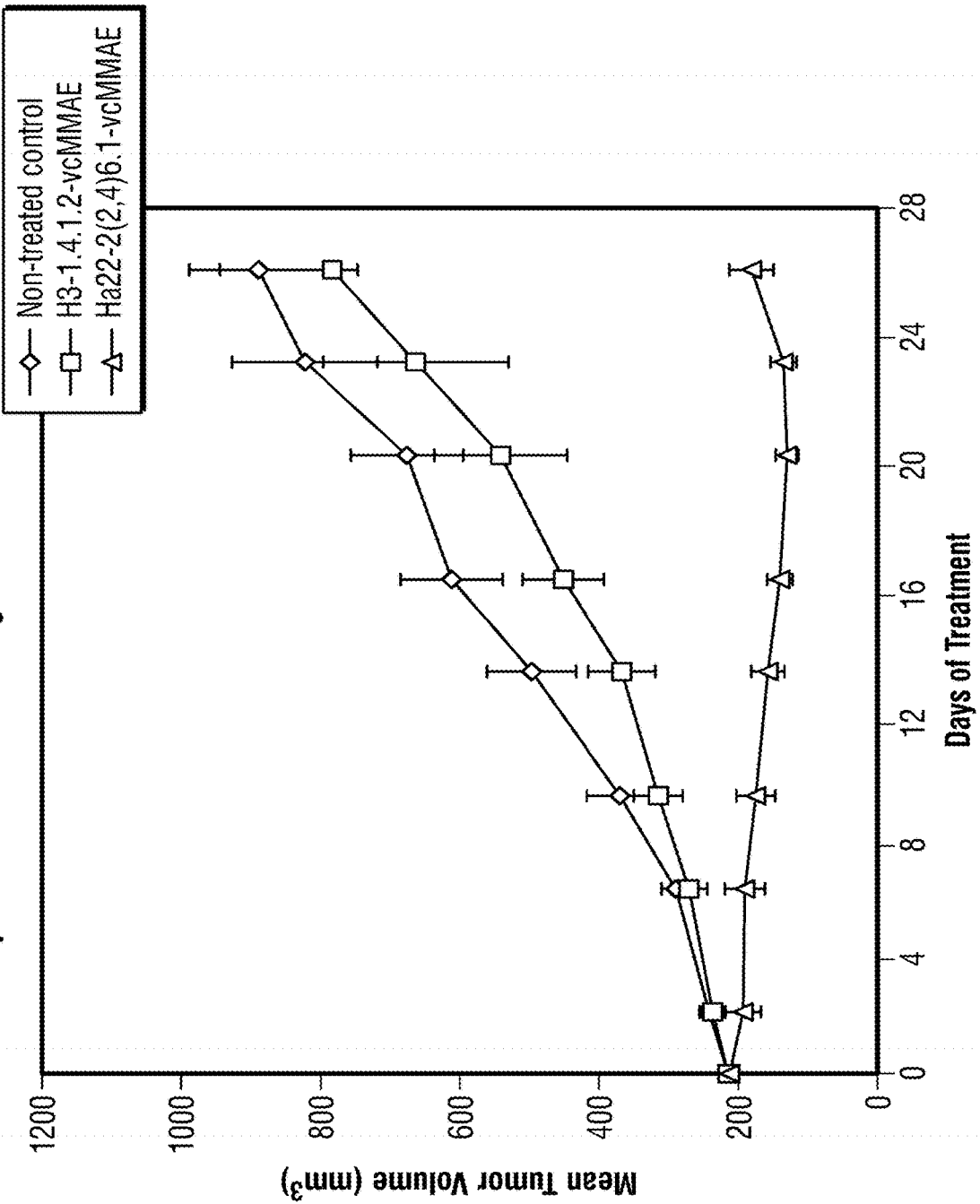

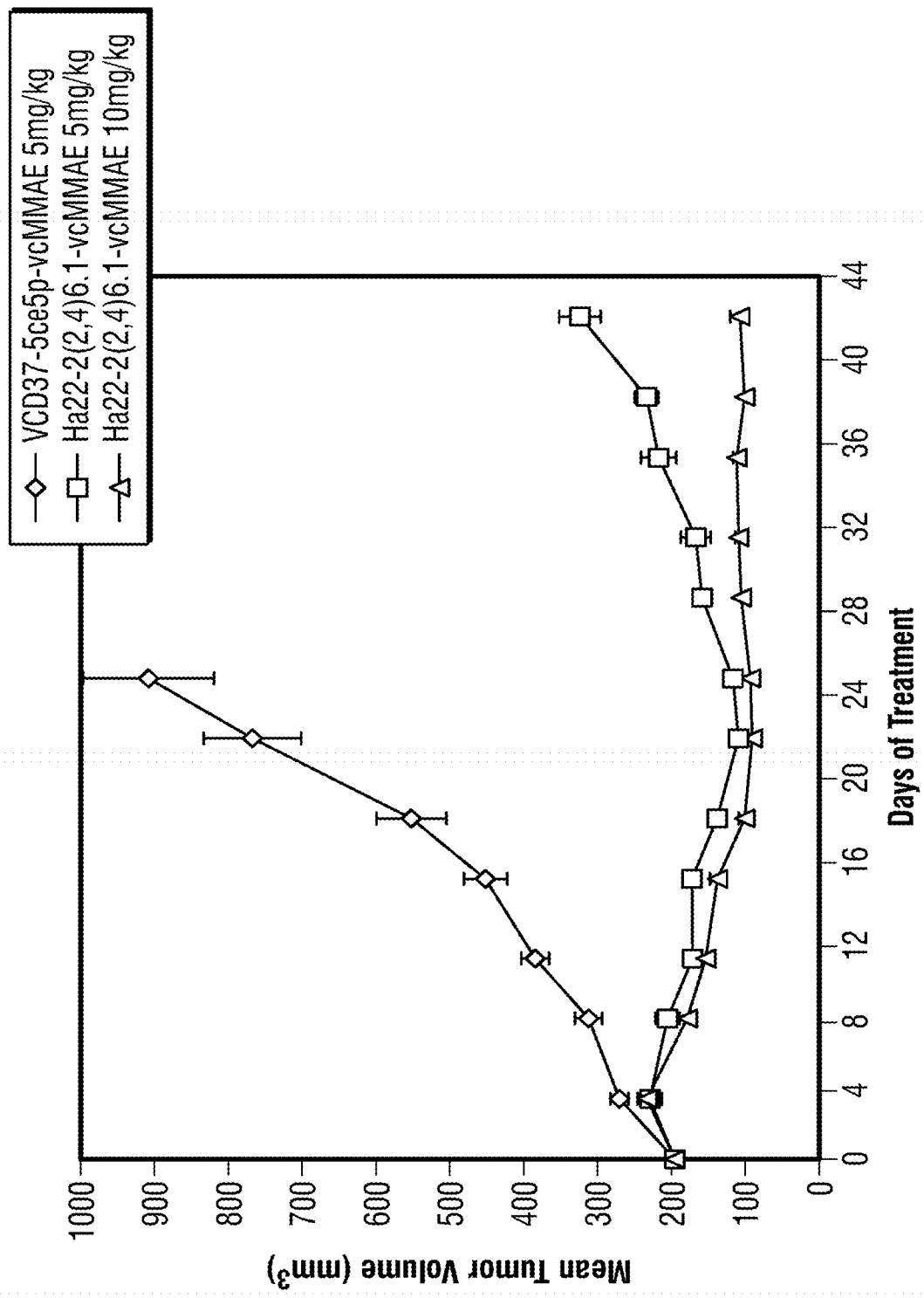
Figure 20: Efficacy of Ha22-2(2,4)6.1-vcMMAE at comparative dosage in subcutaneous established human bladder cancer xenograft AG-B8 in SCID Mice Figure 21: Detection of 191P4D12 protein in cancer
patient specimens by immunohistochemistry.

Bladder cancer specimen

Bladder cancer specimen

Breast cancer specimen

Breast cancer specimen

Pancreatic cancer specimen

Pancreatic cancer specimen

Lung cancer specimen

Lung cancer specimen

Ovarian cancer specimen

Ovarian cancer specimen

Esophageal cancer specimens

Esophageal cancer specimens

Head and neck cancer specimens

Head and neck cancer specimens

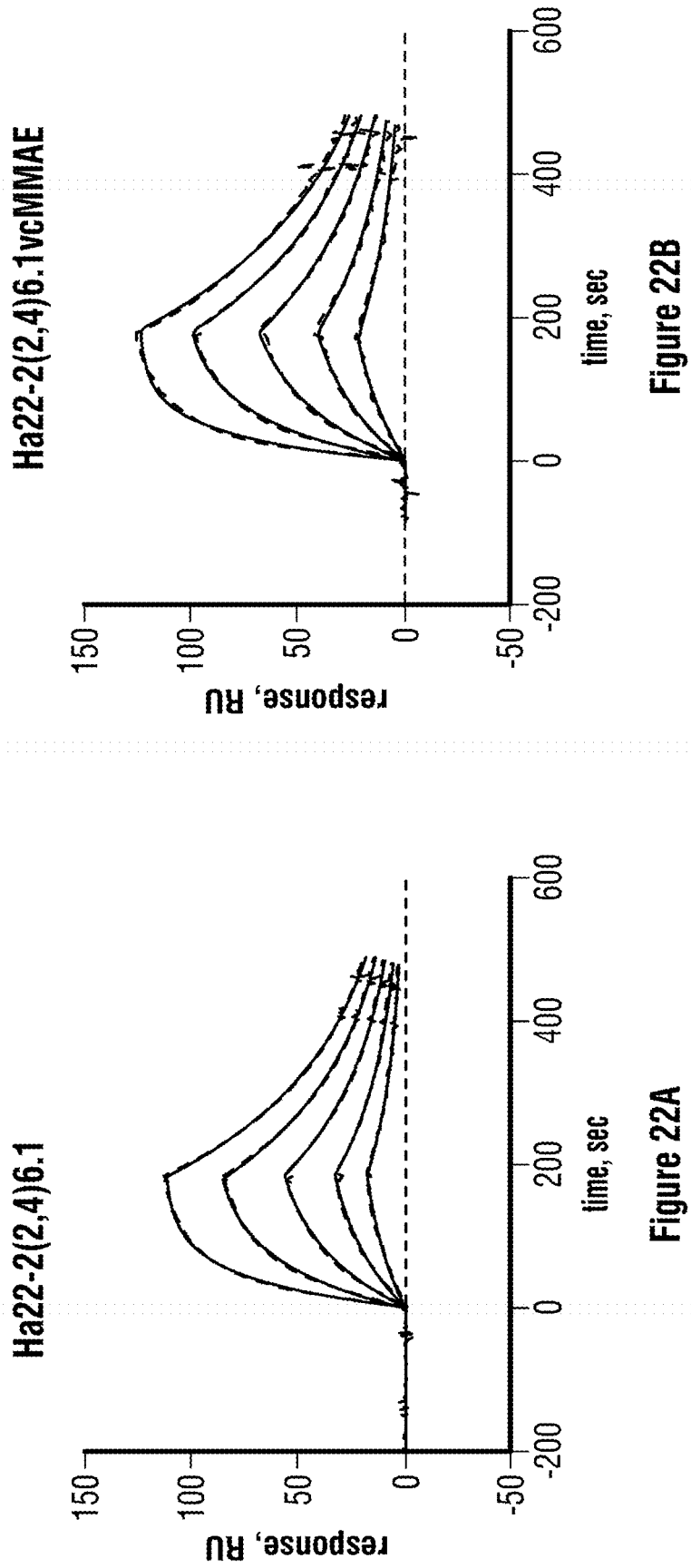
Figure 22: Binding Curves (Sensograms) Used to Determine Affinity via SPR

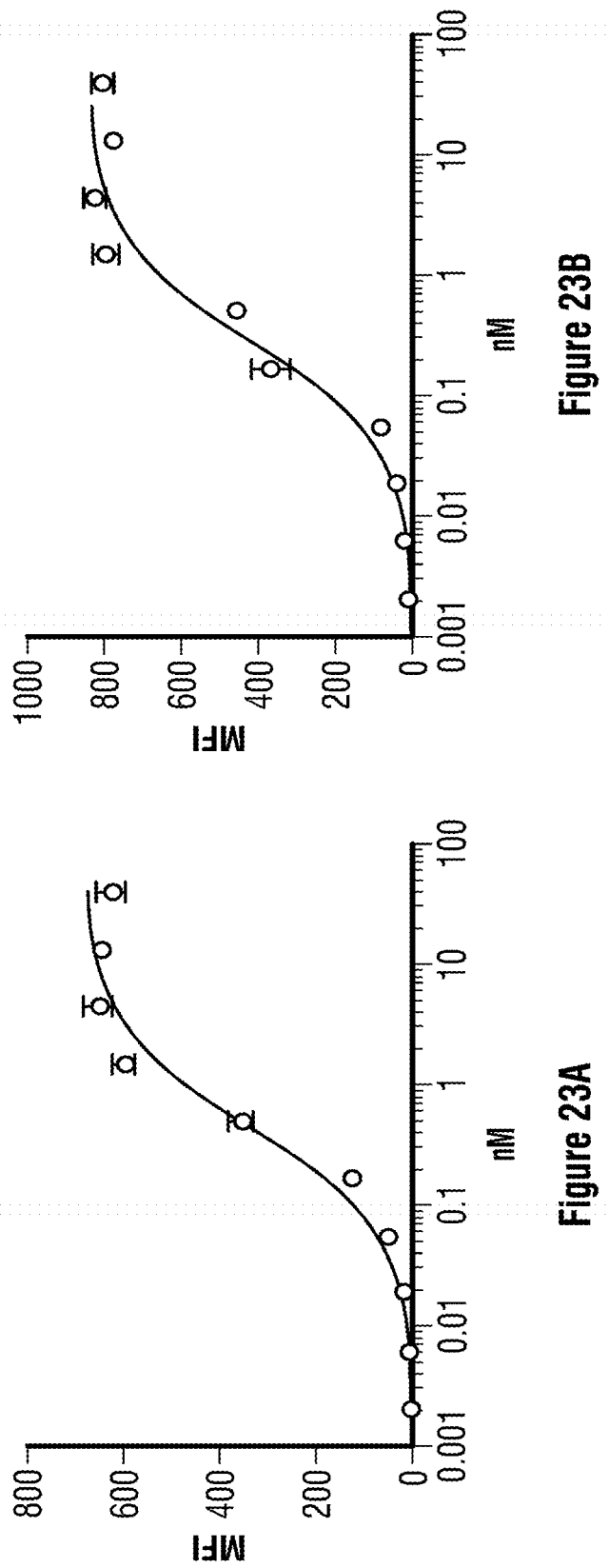
Figure 23: Ha22-2(2,4)6.1 binds to PC3 cells expressing 191P4D12 (A) and orthologs from cynomolgus monkey (B), rat (C) and mouse (D)

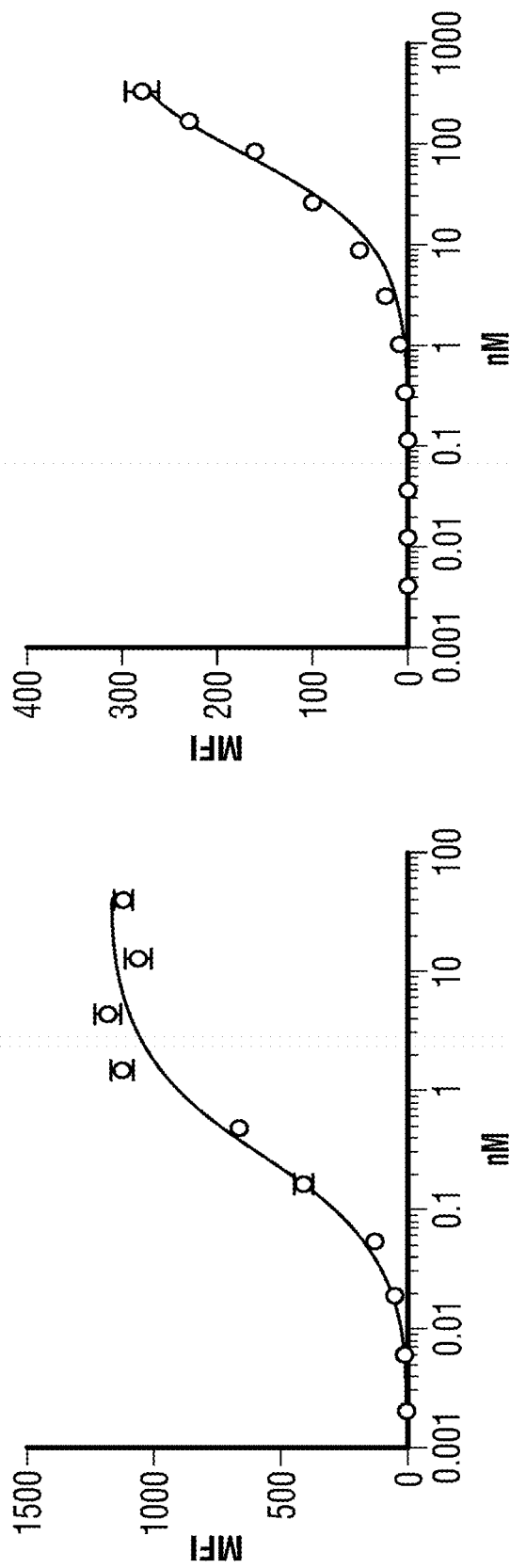
Figure 23 (Continued): Ha22-2(2,4)6.1 binds to PC3 cells expressing 191P4D12 (A) and orthologs from cynomolgus monkey (B), rat (C) and mouse (D)

Figure 24 (Continued):
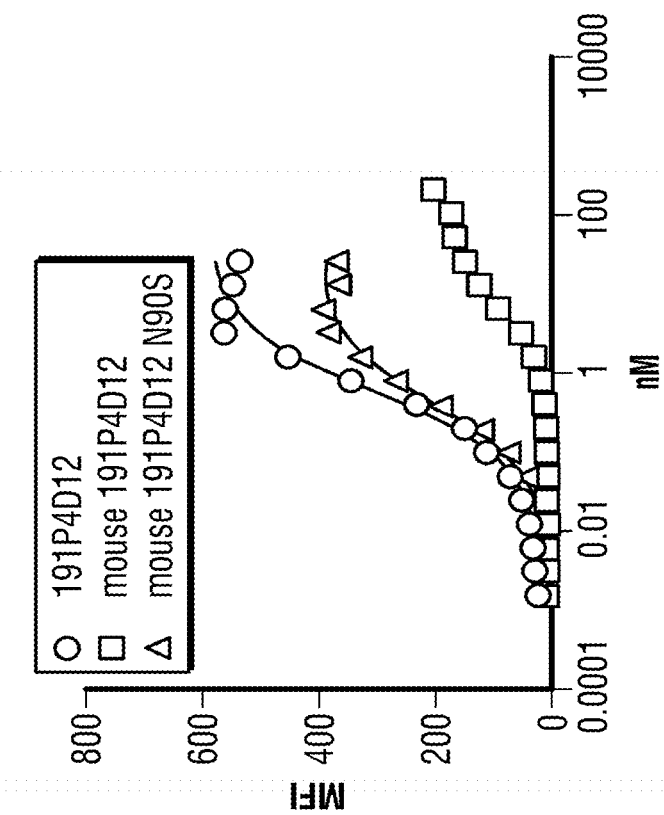
Figure 24C
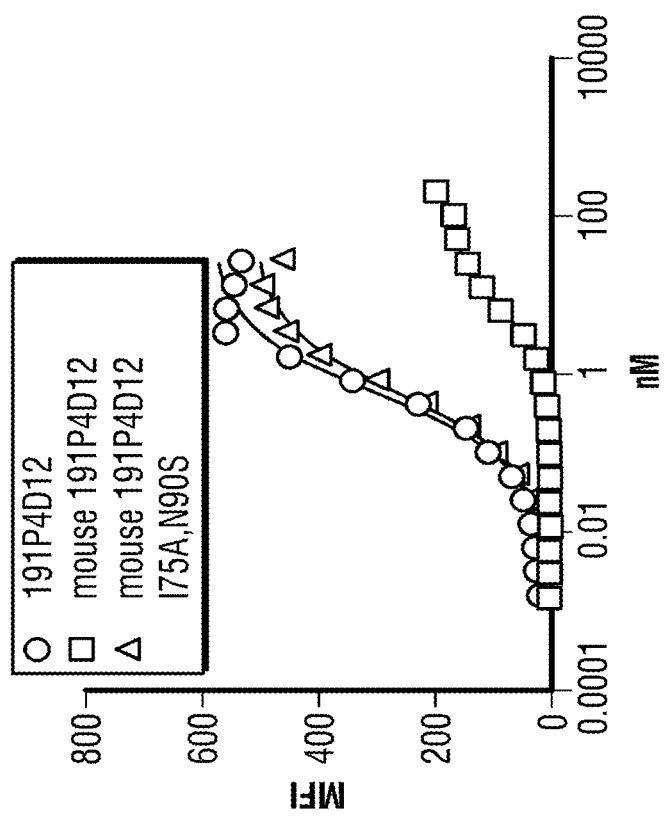
Figure 24D

Figure 26: Binding of Ha22-2(2,4)6.1 Mab assessed by FACS

Figure 26(Continued): Binding of Ha22-2(2,4)6.1 Mab assessed by FACS

ANTIBODY DRUG CONJUGATES (ADC) THAT BIND TO 191P4D12 PROTEINS

CROSS-REFERENCE TO RELATED APPLICATIONS

This application is a continuation of U.S. patent application Ser. No. 15/943,527, filed Apr. 2, 2018, which is a continuation of U.S. patent application Ser. No. 15/069,853, filed Mar. 14, 2016, now U.S. Pat. No. 9,962,454, issued May 8, 2018, which is a continuation of U.S. patent application Ser. No. 14/798,302, filed Jul. 13, 2015, now U.S. Pat. No. 9,314,538, issued Apr. 19, 2016, which is a continuation of U.S. patent application Ser. No. 13/830,899, filed Mar. 14, 2013, now U.S. Pat. No. 9,078,931, issued Jul. 14, 2015, which is a continuation of U.S. patent application Ser. No. 13/249,111, filed Sep. 29, 2011, now U.S. Pat. No. 8,637,642, issued Jan. 28, 2014, which claims the benefit of U.S. Provisional Patent Application No. 61/387,933, filed Sep. 29, 2010. The contents of each application listed in this paragraph are fully incorporated by reference herein.

SUBMISSION OF SEQUENCE LISTING ON ASCII TEXT FILE

This application incorporates by reference in its entirety the Computer Readable Form (CRF) of a Sequence Listing in ASCII text format submitted via EFS-Web. The Sequence Listing text file submitted via EFS-Web, entitled 14369-265-999_SEQ_LISTING.txt, was created on Dec. 7, 2020, and is 41,940 bytes in size.

STATEMENT OF RIGHTS TO INVENTIONS MADE UNDER FEDERALLY SPONSORED RESEARCH

Not applicable.

FIELD OF THE INVENTION

The invention described herein relates to antibodies, binding fragments, and antibody drug conjugates (ADCs) thereof, that bind proteins, termed 191P4D12. The invention further relates to prognostic, prophylactic and therapeutic methods and compositions useful in the treatment of cancers that express 191P4D12.

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, ovary, and bladder represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al., 1997, Nat. Med. 3:402). More recently identified prostate cancer markers include PCTA-1 (Su et al., 1996, Proc. Natl. Acad. Sci. USA 93: 7252), prostate-specific membrane antigen (PSMA) (Pinto et al., Clin Cancer Res 1996 Sep. 2 (9): 1445-51), STEAP (Hubert, et al., Proc Natl Acad Sci USA. 1999 Dec. 7; 96(25): 14523-8) and prostate stem cell antigen (PSCA) (Reiter et al., 1998, Proc. Natl. Acad. Sci. USA 95: 1735).

While previously identified markers such as PSA have facilitated efforts to diagnose and treat prostate cancer, there is need for the identification of additional markers and therapeutic targets for prostate and related cancers in order to further improve diagnosis and therapy. An estimated 130,200 cases of colorectal cancer occurred in 2000 in the United States, including 93,800 cases of colon cancer and 36,400 of rectal cancer.

Colorectal cancers are the third most common cancers in men and women. Incidence rates declined significantly during 1992-1996 (-2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 11% of all U.S. cancer deaths.

At present, surgery is the most common form of therapy for colorectal cancer, and for cancers that have not spread, it is frequently curative. Chemotherapy, or chemotherapy plus radiation, is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. There continues to be a need for effective diagnostic and treatment modalities for colorectal cancer.

Of all new cases of cancer in the United States, bladder cancer represents approximately 5 percent in men (fifth most common neoplasm) and 3 percent in women (eighth most common neoplasm). The incidence is increasing slowly, concurrent with an increasing older population. In 1998, there were an estimated 54,500 cases, including 39,500 in men and 15,000 in women. The age-adjusted incidence in the United States is 32 per 100,000 for men and eight per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increase with age and will be an increasing problem as the population becomes more elderly.

Most bladder cancers recur in the bladder. Bladder cancer is managed with a combination of transurethral resection of the bladder (TUR) and intravesical chemotherapy or immunotherapy. The multifocal and recurrent nature of bladder cancer points out the limitations of TUR. Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

There were an estimated 164,100 new cases of lung and bronchial cancer in 2000, accounting for 14% of all U.S. cancer diagnoses. The incidence rate of lung and bronchial cancer is declining significantly in men, from a high of 86.5 per 100,000 in 1984 to 70.0 in 1996. In the 1990s, the rate of increase among women began to slow. In 1996, the incidence rate in women was 42.3 per 100,000.

Lung and bronchial cancer caused an estimated 156,900 deaths in 2000, accounting for 28% of all cancer deaths. During 1992-1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long lasting. There is however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnosed in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer. Breast cancer ranks second among cancer deaths in women. According to the most recent data, mortality rates declined significantly during 1992-1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy; chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCIS) with adequate amounts of surrounding normal breast tissue may prevent the local recurrence of the DCIS. Radiation to the breast and/or tamoxifen may reduce the chance of DCIS occurring in the remaining breast tissue. This is important because DCIS, if left untreated, may develop into invasive breast cancer. Nevertheless, there are serious side effects or sequelae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992-1996, ovarian cancer incidence rates were significantly declining. Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to remove all intra-abdominal disease to enhance the effect of chemotherapy. There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among women.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for cancers. These include the use of antibodies, vaccines, and small molecules as treatment modalities. Additionally, there is also a need to use these modalities as research tools to diagnose, detect, monitor, and further the state of the art in all areas of cancer treatment and studies.

The therapeutic utility of monoclonal antibodies (mAbs) (G. Kohler and C. Milstein, Nature 256:495-497 (1975)) is being realized. Monoclonal antibodies have now been approved as therapies in transplantation, cancer, infectious disease, cardiovascular disease and inflammation. Different isotypes have different effector functions. Such differences in function are reflected in distinct 3-dimensional structures for the various immunoglobulin isotypes (P. M. Alzari et al., Annual Rev. Immunol., 6:555-580 (1988)).

Because mice are convenient for immunization and recognize most human antigens as foreign, mAbs against human targets with therapeutic potential have typically been of murine origin. However, murine mAbs have inherent disadvantages as human therapeutics. They require more frequent dosing as mAbs have a shorter circulating half-life in humans than human antibodies. More critically, the repeated administration of murine antibodies to the human immune system causes the human immune system to respond by recognizing the mouse protein as a foreign and generating a human anti-mouse antibody (HAMA) response. Such a HAMA response may result in allergic reaction and the rapid clearing of the murine antibody from the system thereby rendering the treatment by murine antibody useless. To avoid such affects, attempts to create human immune systems within mice have been attempted.

Initial attempts hoped to create transgenic mice capable of responding to antigens with antibodies having human sequences (See Bruggemann et al., Proc. Nat'l. Acad. Sci. USA 86:6709-6713 (1989)), but were limited by the amount of DNA that could be stably maintained by available cloning vehicles. The use of yeast artificial chromosome (YAC) cloning vectors led the way to introducing large germline fragments of human Ig locus into transgenic mammals. Essentially a majority of the human V, D, and J region genes arranged with the same spacing found in the human genome and the human constant regions were introduced into mice using YACs. One such transgenic mouse strain is known as XenoMouse® mice and is commercially available from Amgen Fremont, Inc. (Fremont Calif.).

SUMMARY OF THE INVENTION

The invention provides antibodies, binding fragments, and antibody drug conjugates (ADCs) thereof that bind to 191P4D12 proteins and polypeptide fragments of 191P4D12 proteins. In some embodiments, the invention comprises fully human antibodies conjugated with a therapeutic agent. In certain embodiments, there is a proviso that the entire nucleic acid sequence of FIG. 3 is not encoded and/or the entire amino acid sequence of FIG. 2 is not prepared. In certain embodiments, the entire nucleic acid sequence of FIG. 3 is encoded and/or the entire amino acid sequence of FIG. 2 is prepared, either of which are in respective human unit dose forms.

The invention further provides various immunogenic or therapeutic compositions, such as antibody drug conjugates, and strategies for treating cancers that express 191P4D12 such as cancers of tissues listed in Table I.

BRIEF DESCRIPTION OF THE FIGURES

FIG. 1. The cDNA and amino acid sequence of 191P4D12 is shown in FIG. 1. The start methionine is underlined. The open reading frame extends from nucleic acid 264-1796 including the stop codon.

FIGS. 2A-B. Nucleic acid and amino acid sequences of 191P4D12 antibodies. FIG. 2A. The cDNA and amino acid sequence of Ha22-2(2,4)6.1 heavy chain. Double-underlined is the leader sequence, underlined is the heavy chain variable region, and underlined with a dashed line is the human IgG1 constant region. FIG. 2B. The cDNA and amino acid sequence of Ha22-2(2,4)6.1 light chain. Double-underlined is the leader sequence, underlined is the light chain variable region, and underlined with a dashed line is the human kappa constant region.

FIGS. 3A-B. Amino acid sequences of 191P4D12 antibodies. FIG. 3A. The amino acid sequence of Ha22-2(2,4)6.1 heavy chain. Double-underlined is the leader sequence, underlined is the heavy chain variable region, and underlined with a dashed line is the human IgG1 constant region. FIG. 3B. The amino acid sequence of Ha22-2(2,4)6.1 light chain. Double-underlined is the leader sequence, underlined is the light chain variable region, and underlined with a dashed line is the human kappa constant region.

FIGS. 4A-B. Alignment of Ha22-2(2,4)6.1 antibodies to human Ig germline. FIG. 4A. Alignment of Ha22-2(2,4)6.1 heavy chain to human Ig germline. FIG. 4B. Alignment of Ha22-2(2,4)6.1 light chain to human Ig germline.

FIGS. 5A-B. Ha22-2(2,4)6.1 MAb binding assays. FIG. 5A: RAT-control and RAT-191P4D12 cells were stained with Ha22-2(2,4)6.1 MAb from either hybridoma or CHO cells. Binding was detected by flow cytometry. Results show Ha22-2(2,4)6.1 MAb recombinantly expressed in CHO cells is secreted and binds specifically to cell-surface 191P4D12. FIG. 5B: Ha22-2(2,4)6.1 MAb from either hybridoma or CHO cells was tested for binding to recombinant 191P4D12 purified extracellular protein by ELISA. The results show that 191P4D12 protein binding to Ha22-2(2,4)6.1 derived from CHO and hybridoma was identical.

FIG. 6. Ha22-2(2,4)6.1vcMMAE Affinity Determination by FACS using PC3-Human-191P4D12 cells. The affinity is 0.69 Kd.

FIG. 7. Ha22-2(2,4)6.1vcMMAE Affinity Determination by FACS using PC3-Cynomolgus-191P4D12 cells. The affinity is 0.34 Kd.

FIG. 8. Ha22-2(2,4)6.1vcMMAE Affinity Determination by FACS using PC3-Rat-191P4D12 cells. The affinity is 1.6 Kd.

FIG. 9, which includes FIGS. 9A-D. Cell cytotoxicity mediated by Ha22-2(2,4)6.1vcMMAE.

FIG. 10. Domain mapping of Ha22-(2,4)6.1 MAb by FACS.

FIG. 11. Ha22-2(2,4)6.1 MAb domain mapping by Western Blot Analysis.

FIG. 12. Evaluation of Ha22-2(2,4)6.1 MAb in the subcutaneous tumor formation model of human lung cancer xenograft AG-L4 in SCID mice. The results show that the 191P4D12 MAbs did not significantly inhibit tumor growth in human lung cancer xenograft AG-L4 in SCID mice.

FIG. 13. Evaluation of Ha22-2(2,4)6.1 MAb in the subcutaneous tumor formation model of human pancreatic cancer xenograft HPAC in SCID mice. The results show that the 191P4D12 MAbs did not inhibit tumor growth in a human pancreatic xenograft in SCID mice when compared to the control antibody.

FIG. 14. Evaluation of Ha22-2(2,4)6.1 MAb in the subcutaneous tumor formation model of human pancreatic cancer xenograft AG-Panc3 in SCID mice. The results show that the 191P4D12 MAbs did not inhibit tumor growth in a human pancreatic xenograft in SCID mice when compared to the control antibody.

FIG. 15. Efficacy of Ha22-2(2,4)6.1-vcMMAE in subcutaneous established human lung cancer xenograft AG-L4 in SCID mice. The results show that treatment with Ha22-2(2,4)6.1-vcMMAE significantly inhibited the growth of AG-L4 lung cancer xenografts implanted subcutaneously in nude mice compared to both the treated and untreated control.

FIG. 16. Efficacy of Ha22-2(2,4)6.1-vcMMAE in subcutaneous established human breast cancer xenograft BT-483 in SCID mice. The results show that treatment with Ha22-2(2,4)6.1-vcMMAE significantly inhibited the growth of BT-483 breast tumor xenografts implanted subcutaneously in SCID mice compared to the treated and untreated control ADCs.

FIG. 17. Efficacy of Ha22-2(2,4)6.1-vcMMAE in subcutaneous established human bladder cancer xenograft AG-B1 in SCID mice. The results show that treatment with Ha22-2(2,4)6.1-vcMMAE significantly inhibited the growth of AG-B1 bladder cancer xenografts as compared to the control ADCs.

FIG. 18. Efficacy of Ha22-2(2,4)6.1-vcMMAE in subcutaneous established human pancreatic cancer xenograft AG-Panc2 in SCID mice. The results show that treatment with Ha22-2(2,4)6.1-vcMMAE significantly inhibited the growth of AG-Panc2 pancreatic cancer xenografts as compared to the control ADCs.

FIG. 19. Efficacy of Ha22-2(2,4)6.1-vcMMAE in subcutaneous established human lung cancer xenograft AG-Panc4 in SCID mice. The results show that treatment with Ha22-2(2,4)6.1-vcMMAE significantly inhibited the growth of AG-Panc4 pancreatic cancer xenografts as compared to the control ADCs.

FIG. 20. Efficacy of Ha22-2(2,4)6.1-vcMMAE at comparative dosage in subcutaneous established human bladder cancer xenograft AG-B8 in SCID mice. The results show that treatment with Ha22-2(2,4)6.1vcMMAE at 10 mg/kg significantly inhibited the growth of AG-B8 bladder cancer xenografts as compared to the Ha22-2(2,4)6.1vcMMAE at 5 mg/kg.

FIG. 21, which includes FIGS. 21A-N. Detection of 191P4D12 protein in cancer patient specimens by IHC.

FIG. 22, which includes FIGS. 22A-B. Show binding curves used to determine the affinity of Ha22-2(2,4)6.1 Mab and Ha22-2(2,4)6.1vcMMAE to purified recombinant 191P4D12 (ECD amino acids 1-348).

FIG. 23, which includes FIGS. 23A-D. Show binding of Ha22-2(2,4)6.1 to PC3 cells expressing 191P4D12 (FIG. 23A) and orthologs from cynomolgus monkey (FIG. 23B), rat (FIG. 23C) and mouse (FIG. 23D).

FIGS. 24A-D. Show binding of Ha22-2(2,4)6.1 to the double mutant A761, S91N is similar to murine ortholog binding.

DETAILED DESCRIPTION OF THE INVENTION

Outline of Sections

Figure 9A:
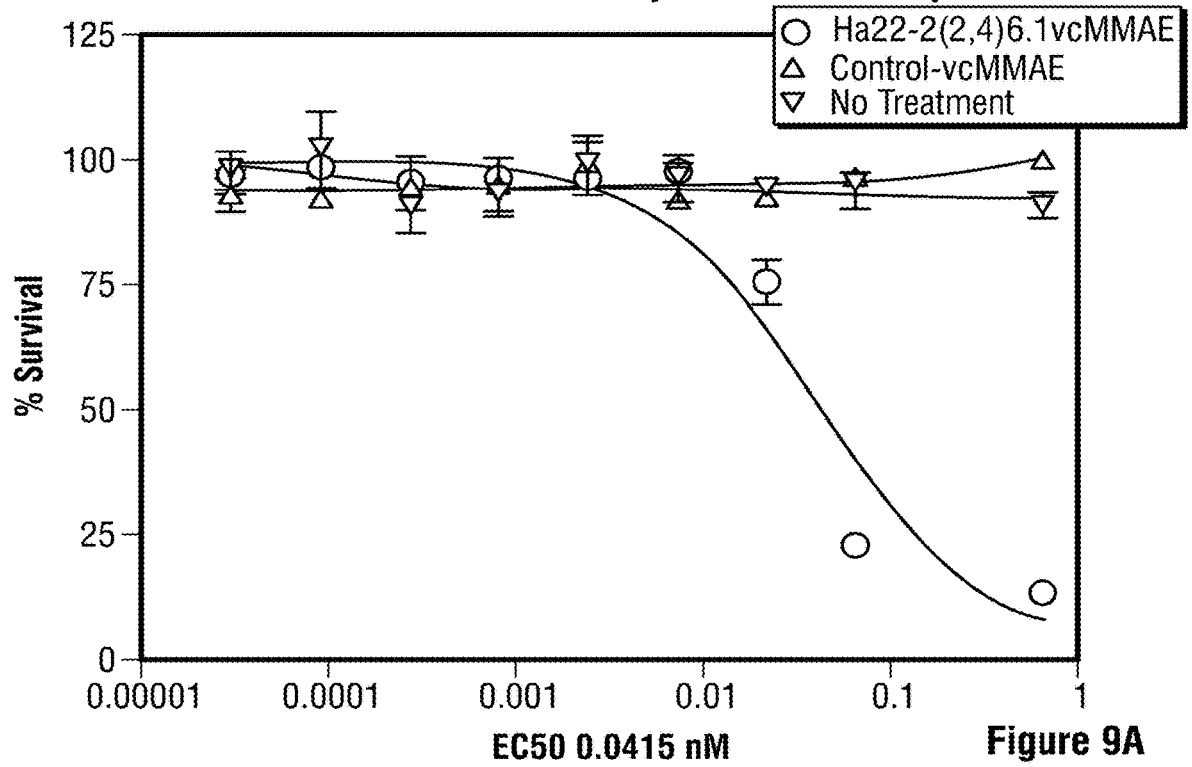
FIG. 9A: Cell cytotoxicity assay using PC3-Human-191P4D12 cells.
Figure 9B:
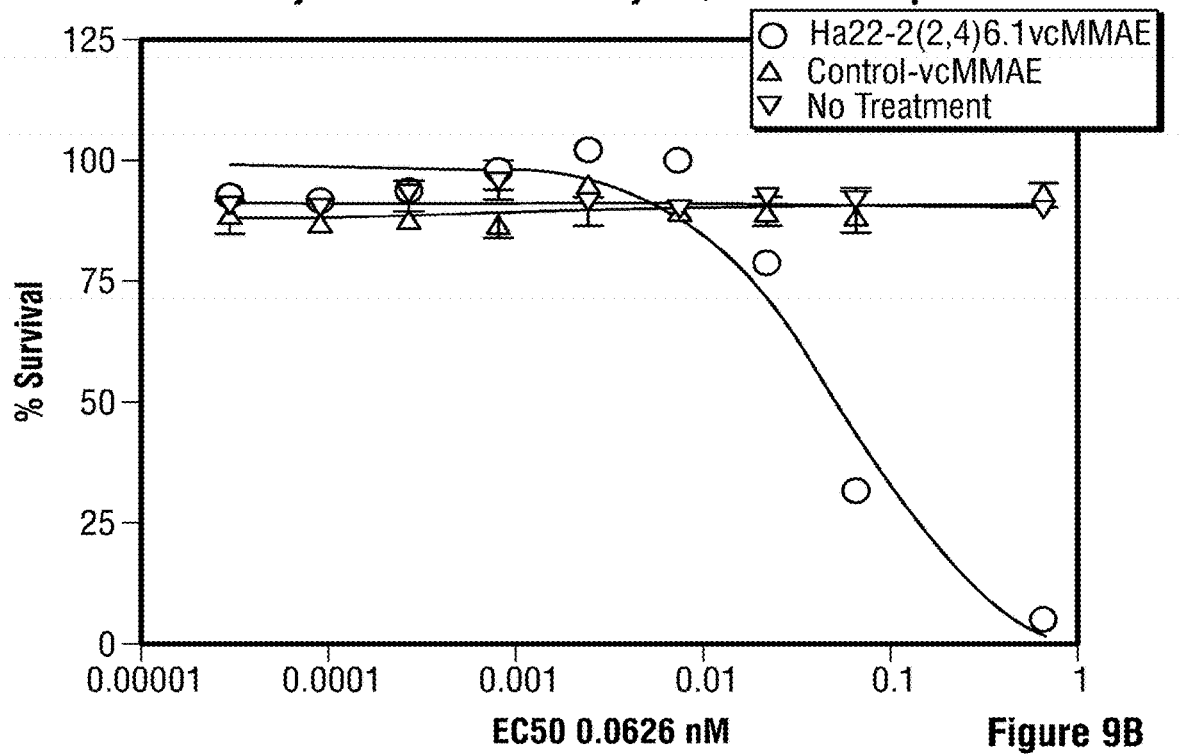
FIG. 9B: Cell cytotoxicity assay using PC3-Cynomolgus-191P4D12 cells.
Figure 9C:
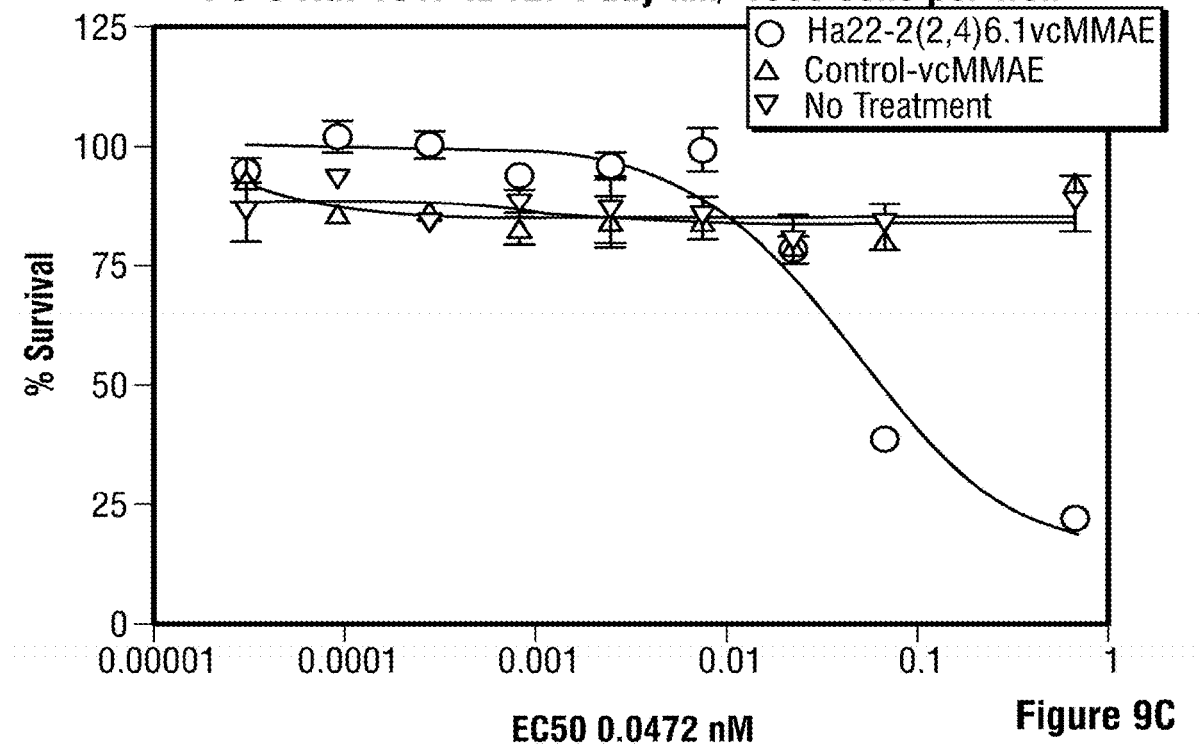
FIG. 9C: Cell cytotoxicity assay using PC3-Rat-191P4D12 cells.

I.) Definitions
II.) 191P4D12 Antibodies
III.) Antibody Drug Conjugates Generally
   III(A). Maytansinoids
   III(B). Auristatins and dolostatins
   III(C). Calicheamicin
   III(D). Other Cytotoxic Agents
IV.) Antibody Drug Conjugates which Bind 191P4D12
V.) Linker Units
VI.) The Stretcher Unit
VII.) The Amino Acid Unit
VIII.) The Spacer Unit
IX.) The Drug Unit
X.) Drug Loading
XI.) Methods of Determining Cytotoxic effect of ADCs
XII.) Treatment of Cancer(s) Expressing 191P4D12
XIII.) 191P4D12 as a Target for Antibody-based Therapy
XIV.) 191P4D12 ADC Cocktails
XV.) Combination Therapy
XVI.) Kits/Articles of Manufacture I.) Definitions Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., *Molecular Cloning: A Laboratory Manual* 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

When a trade name is used herein, reference to the trade name also refers to the product formulation, the generic drug, and the active pharmaceutical ingredient(s) of the trade name product, unless otherwise indicated by context.

The terms "advanced cancer", "locally advanced cancer", "advanced disease" and "locally advanced disease" mean cancers that have extended through the relevant tissue capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) cancer.

The abbreviation "AFP" refers to dimethylvaline-valine-dolaisoleuine-dolaproine-phenylalanine-p-phenylenediamine (see Formula XVI infra).

The abbreviation "MMAE" refers to monomethyl auristatin E (see Formula XI infra).

The abbreviation "AEB" refers to an ester produced by reacting auristatin E with paraacetyl benzoic acid (see Formula XX infra).

The abbreviation "AEVB" refers to an ester produced by reacting auristatin E with benzoylvaleric acid (see Formula XXI infra).

The abbreviation "MMAF" refers to dovaline-valine-dolaisoleuine-dolaproine-phenylalanine (see Formula XVIV infra).

Unless otherwise noted, the term "alkyl" refers to a saturated straight or branched hydrocarbon having from about 1 to about 20 carbon atoms (and all combinations and subcombinations of ranges and specific numbers of carbon atoms therein), with from about 1 to about 8 carbon atoms being preferred. Examples of alkyl groups are methyl, ethyl, n-propyl, iso-propyl, n-butyl, iso-butyl, sec-butyl, tert-butyl, n-pentyl, 2-pentyl, 3-pentyl, 2-methyl-2-butyl, n-hexyl, n-heptyl, n-octyl, n-nonyl, n-decyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

Alkyl groups, whether alone or as part of another group, can be optionally substituted with one or more groups, preferably 1 to 3 groups (and any additional substituents selected from halogen), including, but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR',
—C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl, and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be optionally further substituted with one or more groups including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each $R^{11}$ is independently selected from —H, —$C_1$-$C_8$ alkyl, —$C_2$-$C_8$ alkenyl,
—$C_2$-$C_8$ alkynyl, or -aryl.

Unless otherwise noted, the terms "alkenyl" and "alkynyl" refer to straight and branched carbon chains having from about 2 to about 20 carbon atoms (and all combinations and subcombinations of ranges and specific numbers of carbon atoms therein), with from about 2 to about 8 carbon atoms being preferred. An alkenyl chain has at least one double bond in the chain and an alkynyl chain has at least one triple bond in the chain. Examples of alkenyl groups include, but are not limited to, ethylene or vinyl, allyl, -1-butenyl, -2-butenyl, -isobutylenyl, -1-pentenyl, -2-pentenyl, -3-methyl-1-butenyl, -2-methyl-2-butenyl, and -2,3-dimethyl-2-butenyl. Examples of alkynyl groups include, but are not limited to, acetylenic, propargyl, acetyl enyl, propynyl, -1-butynyl, -2-butynyl, -1-pentynyl, -2-pentynyl, and -3-methyl-1 butynyl.

Alkenyl and alkynyl groups, whether alone or as part of another group, can be optionally substituted with one or more groups, preferably 1 to 3 groups (and any additional substituents selected from halogen), including but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkyenl, —$C_2$-$C_8$ alkynyl, or -aryl and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be optionally further substituted with one or more substituents including, but not limited to,
—$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each $R^{11}$ is independently selected from —H, —$C_1$-$C_8$ alkyl, —$C_2$-$C_8$ alkenyl, —$C_2$-$C_8$ alkynyl, or -aryl.

Unless otherwise noted, the term "alkylene" refers to a saturated branched or straight chain hydrocarbon radical having from about 1 to about 20 carbon atoms (and all combinations and subcombinations of ranges and specific numbers of carbon atoms therein), with from about 1 to about 8 carbon atoms being preferred and having two monovalent radical centers derived by the removal of two hydrogen atoms from the same or two different carbon atoms of a parent alkane. Typical alkylenes include, but are not limited to, methylene, ethylene, propylene, butylene, pentylene, hexylene, heptylene, ocytylene, nonylene, decalene, 1,4-cyclohexylene, and the like. Alkylene groups, whether alone or as part of another group, can be optionally substituted with one or more groups, preferably 1 to 3 groups (and any additional substituents selected from halogen), including, but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be further optionally substituted with one or more substituents including, but not limited to,
—$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each $R^{11}$ is independently selected from —H, —$C_1$-$C_8$ alkyl,
—$C_2$-$C_8$ alkenyl, —$C_2$-$C_8$ alkynyl, or -aryl.

Unless otherwise noted, the term "alkenylene" refers to an optionally substituted alkylene group containing at least one carbon-carbon double bond. Exemplary alkenylene groups include, for example, ethenylene (—CH=CH—) and propenylene (—CH=CHCH$_2$—).

Unless otherwise noted, the term "alkynylene" refers to an optionally substituted alkylene group containing at least one carbon-carbon triple bond. Exemplary alkynylene groups include, for example, acetylene (—C≡C—), propargyl (—CH$_2$C≡C—), and 4-pentynyl (—CH$_2$CH$_2$CH$_2$C≡CH—).

Unless otherwise noted, the term "aryl" refers to a monovalent aromatic hydrocarbon radical of 6-20 carbon atoms (and all combinations and subcombinations of ranges and specific numbers of carbon atoms therein) derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, phenyl, naphthalene, anthracene, biphenyl, and the like.

An aryl group, whether alone or as part of another group, can be optionally substituted with one or more, preferably 1 to 5, or even 1 to 2 groups including, but not limited to, -halogen, —C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —NO$_2$, —N$_3$, —NH$_2$, —NH(R'), —N(R')$_2$ and —CN, where each R' is independently selected from —H, —C$_1$-C$_8$ alkyl, —C$_2$-C$_8$ alkenyl, —C$_2$-C$_8$ alkynyl, or -aryl and wherein said —C$_1$-C$_8$ alkyl, —C$_2$-C$_8$ alkenyl, —C$_2$-C$_8$ alkynyl, O—(C$_1$-C$_8$ alkyl), —O—(C$_2$-C$_8$ alkenyl), —O—(C$_2$-C$_8$ alkynyl), and -aryl groups can be further optionally substituted with one or more substituents including, but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R$^{11}$ is independently selected from —H, —C$_1$-C$_8$ alkyl, —C$_2$-C$_8$ alkenyl, —C$_2$-C$_8$ alkynyl, or -aryl.

Unless otherwise noted, the term "arylene" refers to an optionally substituted aryl group which is divalent (i.e., derived by the removal of two hydrogen atoms from the same or two different carbon atoms of a parent aromatic ring system) and can be in the ortho, meta, or para configurations as shown in the following structures with phenyl as the exemplary aryl group.

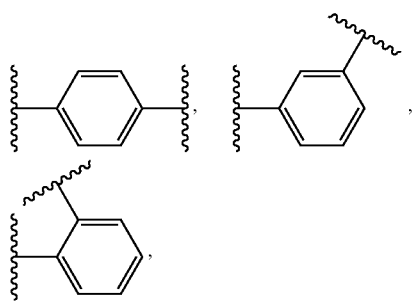

Typical "—(C$_1$-C$_8$ alkylene)aryl," "—(C$_2$-C$_8$ alkenylene)aryl", "and —(C$_2$-C$_8$ alkynylene)aryl" groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

Unless otherwise noted, the term "heterocycle," refers to a monocyclic, bicyclic, or polycyclic ring system having from 3 to 14 ring atoms (also referred to as ring members) wherein at least one ring atom in at least one ring is a heteroatom selected from N, O, P, or S (and all combinations and subcombinations of ranges and specific numbers of carbon atoms and heteroatoms therein). The heterocycle can have from 1 to 4 ring heteroatoms independently selected from N, O, P, or S. One or more N, C, or S atoms in a heterocycle can be oxidized. A monocylic heterocycle preferably has 3 to 7 ring members (e.g., 2 to 6 carbon atoms and 1 to 3 heteroatoms independently selected from N, O, P, or S), and a bicyclic heterocycle preferably has 5 to 10 ring members (e.g., 4 to 9 carbon atoms and 1 to 3 heteroatoms independently selected from N, O, P, or S). The ring that includes the heteroatom can be aromatic or non-aromatic. Unless otherwise noted, the heterocycle is attached to its pendant group at any heteroatom or carbon atom that results in a stable structure.

Heterocycles are described in Paquette, "*Principles of Modern Heterocyclic Chemistry*" (W. A. Benjamin, New York, 1968), particularly Chapters 1, 3, 4, 6, 7, and 9; "*The Chemistry of Heterocyclic Compounds, A series of Monographs*" (John Wiley & Sons, New York, 1950 to present), in particular Volumes 13, 14, 16, 19, and 28; and *J. Am. Chem. Soc.* 82:5566 (1960).

Examples of "heterocycle" groups include by way of example and not limitation pyridyl, dihydropyridyl, tetrahydropyridyl (piperidyl), thiazolyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl. Preferred "heterocycle" groups include, but are not limited to, benzofuranyl, benzothiophenyl, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl.

A heterocycle group, whether alone or as part of another group, can be optionally substituted with one or more groups, preferably 1 to 2 groups, including but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —N$_3$, —NH$_2$, —NH(R'), —N(R')$_2$ and —CN, where each R' is independently selected from —H, —C$_1$-C$_8$ alkyl, —C$_2$-C$_8$ alkenyl, —C$_2$-C$_8$ alkynyl, or -aryl and wherein said —O—(C$_1$-C$_8$ alkyl), —O—(C$_2$-C$_8$ alkenyl), —O—(C$_2$-C$_8$ alkynyl), —C$_1$-C$_8$ alkyl, —C$_2$-C$_8$ alkenyl, —C$_2$-C$_8$ alkynyl, and -aryl groups can be further optionally substituted with one or more substituents including, but not limited to, —C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R$^{11}$ is independently selected from —H, —C$_1$-C$_8$ alkyl, —C$_2$-C$_8$ alkenyl, —C$_2$-C$_8$ alkynyl, or aryl.

By way of example and not limitation, carbon-bonded heterocycles can be bonded at the following positions: position 2, 3, 4, 5, or 6 of a pyridine; position 3, 4, 5, or 6 of a pyridazine; position 2, 4, 5, or 6 of a pyrimidine; position 2, 3, 5, or 6 of a pyrazine; position 2, 3, 4, or 5 of a furan, tetrahydrofuran, thiofuran, thiophene, pyrrole or tetrahydropyrrole; position 2, 4, or 5 of an oxazole, imidazole or thiazole; position 3, 4, or 5 of an isoxazole, pyrazole, or isothiazole; position 2 or 3 of an aziridine; position 2, 3, or 4 of an azetidine; position 2, 3, 4, 5, 6, 7, or 8 of a quinoline; or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, or 1H-indazole; position 2 of a isoindole, or isoindoline; position 4 of a morpholine; and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

Unless otherwise noted, the term "carbocycle," refers to a saturated or unsaturated non-aromatic monocyclic, bicyclic, or polycyclic ring system having from 3 to 14 ring atoms (and all combinations and subcombinations of ranges and specific numbers of carbon atoms therein) wherein all of the ring atoms are carbon atoms. Monocyclic carbocycles preferably have 3 to 6 ring atoms, still more preferably 5 or 6 ring atoms. Bicyclic carbocycles preferably have 7 to 12 ring atoms, e.g., arranged as a bicyclo [4,5], [5,5], [5,6] or [6,6] system, or 9 or 10 ring atoms arranged as a bicyclo [5,6] or [6,6] system. The term "carbocycle" includes, for example, a monocyclic carbocycle ring fused to an aryl ring (e.g., a monocyclic carbocycle ring fused to a benzene ring). Carbocyles preferably have 3 to 8 carbon ring atoms.

Carbocycle groups, whether alone or as part of another group, can be optionally substituted with, for example, one or more groups, preferably 1 or 2 groups (and any additional substituents selected from halogen), including, but not limited to, -halogen, —C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —C$_1$-C$_8$ alkyl, —C$_2$-C$_8$ alkenyl, —C$_2$-C$_8$ alkynyl, or -aryl and wherein said —C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), and -aryl groups can be further optionally substituted with one or more substituents including, but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R$^{11}$ is independently selected from —H, —C$_1$-C$_8$ alkyl, —C$_2$-C$_8$ alkenyl, —C$_2$-C$_8$ alkynyl, or -aryl.

Examples of monocyclic carbocylic substituents include -cyclopropyl, -cyclobutyl, -cyclopentyl, -1-cyclopent-1-enyl, -1-cyclopent-2-enyl, -1-cyclopent-3-enyl, cyclohexyl, -1-cyclohex-1-enyl, -1-cyclohex-2-enyl, -1-cyclohex-3-enyl, -cycloheptyl, -cyclooctyl. -1,3-cyclohexadienyl, -1,4-cyclohexadienyl, -1,3-cycloheptadienyl, -1,3,5-cycloheptatrienyl, and -cyclooctadienyl.

A "carbocyclo," whether used alone or as part of another group, refers to an optionally substituted carbocycle group as defined above that is divalent (i.e., derived by the removal of two hydrogen atoms from the same or two different carbon atoms of a parent carbocyclic ring system).

Unless otherwise indicated by context, a hyphen (-) designates the point of attachment to the pendant molecule. Accordingly, the term "—(C$_1$-C$_8$ alkylene)aryl" or "—C$_1$-C$_8$ alkylene(aryl)" refers to a C$_1$-C$_8$ alkylene radical as defined herein wherein the alkylene radical is attached to the pendant molecule at any of the carbon atoms of the alkylene radical and one of the hydrogen atoms bonded to a carbon atom of the alkylene radical is replaced with an aryl radical as defined herein.

When a particular group is "substituted", that group may have one or more substituents, preferably from one to five substituents, more preferably from one to three substituents, most preferably from one to two substituents, independently selected from the list of substituents. The group can, however, generally have any number of substituents selected from halogen. Groups that are substituted are so indicated.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Protective groups as used herein refer to groups which selectively block, either temporarily or permanently, one reactive site in a multifunctional compound. Suitable hydroxy-protecting groups for use in the present invention are pharmaceutically acceptable and may or may not need to be cleaved from the parent compound after administration to a subject in order for the compound to be active. Cleavage is through normal metabolic processes within the body. Hydroxy protecting groups are well known in the art, see, *Protective Groups in Organic Synthesis* by T. W. Greene and P. G. M. Wuts (John Wiley & sons, 3$^{rd}$ Edition) incorporated herein by reference in its entirety and for all purposes and include, for example, ether (e.g., alkyl ethers and silyl ethers including, for example, dialkylsilylether, trialkylsilylether, dialkylalkoxysilylether), ester, carbonate, carbamates, sulfonate, and phosphate protecting groups. Examples of hydroxy protecting groups include, but are not limited to, methyl ether; methoxymethyl ether, methylthiomethyl ether, (phenyldimethylsilyl)methoxymethyl ether, benzyloxymethyl ether, p-methoxybenzyloxymethyl ether, p-nitrobenzyloxymethyl ether, o-nitrobenzyloxymethyl ether, (4-methoxyphenoxy)methyl ether, guaiacolmethyl ether, t-butoxymethyl ether, 4-pentenyloxymethyl ether, siloxymethyl ether, 2-methoxyethoxymethyl ether, 2,2,2-trichloroethoxymethyl ether, bis(2-chloroethoxy)methyl ether, 2-(trimethylsilyl)ethoxymethyl ether, menthoxymethyl ether, tetrahydropyranyl ether, 1-methoxycylcohexyl ether, 4-methoxytetrahydrothiopyranyl ether, 4-methoxytetrahydrothiopyranyl ether S,S-Dioxide, 1-[(2-choro-4-methyl) phenyl]-4-methoxypiperidin-4-yl ether, 1-(2-fluorophneyl)-4-methoxypiperidin-4-yl ether, 1,4-dioxan-2-yl ether, tetrahydrofuranyl ether, tetrahydrothiofuranyl ether; substituted ethyl ethers such as 1-ethoxyethyl ether, 1-(2-chloroethoxy)ethyl ether, 1-[2-(trimethylsilyl)ethoxy]ethyl ether, 1-methyl-1-methoxyethyl ether, 1-methyl-1-benzyloxyethyl ether, 1-methyl-1-benzyloxy-2-fluoroethyl ether, 1-methyl-1phenoxyethyl ether, 2-trimethylsilyl ether, t-butyl ether, allyl ether, propargyl ethers, p-chlorophenyl ether, p-methoxyphenyl ether, benzyl ether, p-methoxybenzyl ether 3,4-dimethoxybenzyl ether, trimethylsilyl ether, triethylsilyl ether, tripropylsilylether, dimethylisopropylsilyl ether, diethylisopropylsilyl ether, dimethylhexylsilyl ether, t-butyldimethylsilyl ether, diphenylmethylsilyl ether, benzoylformate ester, acetate ester, chloroacetate ester, dichloroacetate ester, trichloroacetate ester, trifluoroacetate ester, methoxyacetate ester, triphneylmethoxyacetate ester, phenylacetate ester, benzoate ester, alkyl methyl carbonate, alkyl 9-fluorenylmethyl carbonate, alkyl ethyl carbonate, alkyl 2,2,2,-trichloroethyl carbonate, 1,1,-dimethyl-2,2,2-trichloroethyl carbonate, alkylsulfonate, methanesulfonate, benzylsulfonate, tosylate, methylene acetal, ethylidene acetal, and t-butylmethylidene ketal. Preferred protecting groups are represented by the formulas —$R^a$,
—$Si(R^a)(R^a)(R^a)$, —$C(O)R^a$, —$C(O)OR^a$, —$C(O)NH(R^a)$, —$S(O)_2R^a$, —$S(O)_2OH$, $P(O)(OH)_2$, and —$P(O)(OH)OR^a$, wherein $R^a$ is $C_1$-$C_{20}$ alkyl, $C_2$-$C_{20}$ alkenyl, $C_2$-$C_{20}$ alkynyl, —$C_1$-$C_{20}$ alkylene(carbocycle), —$C_2$-$C_{20}$ alkenylene(carbocycle), —$C_2$-$C_{20}$ alkynylene(carbocycle), —$C_6$-$C_{10}$ aryl, —$C_1$-$C_{20}$ alkylene(aryl), —$C_2$-$C_{20}$ alkenylene(aryl), —$C_2$-$C_{20}$ alkynylene(aryl), —$C_1$-$C_{20}$ alkylene(heterocycle), —$C_2$-$C_{20}$ alkenylene(heterocycle), or —$C_2$-$C_{20}$ alkynylene (heterocycle) wherein said alkyl, alkenyl, alkynyl, alkylene, alkenylene, alkynylene, aryl, carbocycle, and heterocycle radicals whether alone or as part of another group are optionally substituted.

"Altering the native glycosylation pattern" is intended for purposes herein to mean deleting one or more carbohydrate moieties found in native sequence 191P4D12 (either by removing the underlying glycosylation site or by deleting the glycosylation by chemical and/or enzymatic means), and/or adding one or more glycosylation sites that are not present in the native sequence 191P4D12. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a 191P4D12-related protein). For example, an analog of a 191P4D12 protein can be specifically bound by an antibody or T cell that specifically binds to 191P4D12.

The term "antibody" is used in the broadest sense unless clearly indicated otherwise. Therefore, an "antibody" can be naturally occurring or man-made such as monoclonal antibodies produced by conventional hybridoma technology. 191P4D12 antibodies comprise monoclonal and polyclonal antibodies as well as fragments containing the antigen-binding domain and/or one or more complementarity determining regions of these antibodies. As used herein, the term "antibody" refers to any form of antibody or fragment thereof that specifically binds 191P4D12 and/or exhibits the desired biological activity and specifically covers monoclonal antibodies (including full length monoclonal antibodies), polyclonal antibodies, multispecific antibodies (e.g., bispecific antibodies), and antibody fragments so long as they specifically bind 191P4D12 and/or exhibit the desired biological activity. Any specific antibody can be used in the methods and compositions provided herein. Thus, in one embodiment the term "antibody" encompasses a molecule comprising at least one variable region from a light chain immunoglobulin molecule and at least one variable region from a heavy chain molecule that in combination form a specific binding site for the target antigen. In one embodiment, the antibody is an IgG antibody. For example, the antibody is a IgG1, IgG2, IgG3, or IgG4 antibody. The antibodies useful in the present methods and compositions can be generated in cell culture, in phage, or in various animals, including but not limited to cows, rabbits, goats, mice, rats, hamsters, guinea pigs, sheep, dogs, cats, monkeys, chimpanzees, and apes. Therefore, in one embodiment, an antibody of the present invention is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, ANTIBODY PRODUCTION: ESSENTIAL TECHNIQUES (Wiley, 1997); Shephard, et al., MONOCLONAL ANTIBODIES (Oxford University Press, 2000); Goding, MONOCLONAL ANTIBODIES: PRINCIPLES AND PRACTICE (Academic Press, 1993); and CURRENT PROTOCOLS IN IMMUNOLOGY (John Wiley & Sons, most recent edition). An antibody of the present invention can be modified by recombinant means to increase efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. Nos. 5,624,821, 6,194,551, Application No. WO 9958572; and Angal, et al., *Mol. Immunol.* 30: 105-08 (1993). The modification in amino acids includes deletions, additions, and substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to normal or defective 191P4D12. See e.g., *Antibody Engineering: A Practical Approach* (Oxford University Press, 1996). Suitable antibodies with the desired biologic activities can be identified using the following in vitro assays including but not limited to: proliferation, migration, adhesion, soft agar growth, angiogenesis, cell-cell communication, apoptosis, transport, signal transduction, and the following in vivo assays such as the inhibition of tumor growth. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays. They can also be used to quantify the 191P4D12 or its receptor.

The term "antigen-binding portion" or "antibody fragment" of an antibody (or simply "antibody portion"), as used herein, refers to one or more fragments of a 191P4D12 antibody that retain the ability to specifically bind to an antigen (e.g., 191P4D12 and variants; FIG. 1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarily determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

As used herein, any form of the "antigen" can be used to generate an antibody that is specific for 191P4D12. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may be genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids. In one embodiment, the antibody of the methods and compositions herein specifically bind at least a portion of the extracellular domain of the 191P4D12 of interest.

The antibodies or antigen binding fragments thereof provided herein may be conjugated to a "bioactive agent." As used herein, the term "bioactive agent" refers to any synthetic or naturally occurring compound that binds the antigen and/or enhances or mediates a desired biological effect to enhance cell-killing toxins. In one embodiment, the binding fragments useful in the present invention are biologically active fragments. As used herein, the term "biologically active" refers to an antibody or antibody fragment that is capable of binding the desired antigenic epitope and directly or indirectly exerting a biologic effect. Direct effects include, but are not limited to the modulation, stimulation, and/or inhibition of a growth signal, the modulation, stimulation, and/or inhibition of an anti-apoptotic signal, the modulation, stimulation, and/or inhibition of an apoptotic or necrotic signal, modulation, stimulation, and/or inhibition the ADCC cascade, and modulation, stimulation, and/or inhibition the CDC cascade.

"Bispecific" antibodies are also useful in the present methods and compositions. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al., Nature 305:537-39 (1983). Alternatively, bispecific antibodies can be prepared using chemical linkage. See, e.g., Brennan, et al., Science 229:81 (1985). Bispecific antibodies include bispecific antibody fragments. See, e.g., Hollinger, et al., Proc. Natl. Acad. Sci. U.S.A. 90:6444-48 (1993), Gruber, et al., J. Immunol. 152:5368 (1994).

The monoclonal antibodies described herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity (U.S. Pat. No. 4,816,567; and Morrison et al., Proc. Natl. Acad. Sci. USA 81: 6851-6855 (1984)).

The term "Chemotherapeutic Agent" refers to all chemical compounds that are effective in inhibiting tumor growth. Non-limiting examples of chemotherapeutic agents include alkylating agents; for example, nitrogen mustards, ethyleneimine compounds and alkyl sulphonates; antimetabolites, for example, folic acid, purine or pyrimidine antagonists; mitotic inhibitors, for example, anti-tubulin agents such as vinca alkaloids, auristatins and derivatives of podophyllotoxin; cytotoxic antibiotics; compounds that damage or interfere with DNA expression or replication, for example, DNA minor groove binders; and growth factor receptor antagonists. In addition, chemotherapeutic agents include cytotoxic agents (as defined herein), antibodies, biological molecules and small molecules.

The term "compound" refers to and encompasses the chemical compound itself as well as, whether explicitly stated or not, and unless the context makes clear that the following are to be excluded: amorphous and crystalline forms of the compound, including polymorphic forms, where these forms may be part of a mixture or in isolation; free acid and free base forms of the compound, which are typically the forms shown in the structures provided herein; isomers of the compound, which refers to optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, preferably pharmaceutically acceptable salts, including acid addition salts and base addition salts, including salts having organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different. In some instances, reference made herein to a compound of the invention will include an explicit reference to one or of the above forms, e.g., salts and/or solvates; however, this reference is for emphasis only, and is not to be construed as excluding other of the above forms as identified above.

As used herein, the term "conservative substitution" refers to substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., MOLECULAR BIOLOGY OF THE GENE, The Benjamin/Cummings Pub. Co., p. 224 (4th Edition 1987)). Such exemplary substitutions are preferably made in accordance with those set forth in Table II and Table(s) III(a-b). For example, such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III(a) herein; pages 13-15 "Biochemistry" 2nd ED. Lubert Stryer ed (Stanford University); Henikoff et al., PNAS 1992 Vol 89 10915-10919; Lei et al., J Biol Chem 1995 May 19; 270(20):11882-11886). Other substitutions are also permissible and may be determined empirically or in accord with known conservative substitutions.

The term "cytotoxic agent" refers to a substance that inhibits or prevents the expression activity of cells, function of cells and/or causes destruction of cells. The term is intended to include radioactive isotopes, chemotherapeutic agents, and toxins such as small molecule toxins or enzymatically active toxins of bacterial, fungal, plant or animal origin, including fragments and/or variants thereof. Examples of cytotoxic agents include, but are not limited to auristatins (e.g., auristatin E, auristatin F, MMAE and MMAF), auromycins, maytansinoids, ricin, ricin A-chain, combrestatin, duocarmycins, dolastatins, doxorubicin, daunorubicin, taxols, cisplatin, cc1065, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, *Sapaonaria officinalis* inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212}$ or $^{213}$, $P^{32}$ and radioactive isotopes of Lu including $Lu^{177}$. Antibodies may also be conjugated to an anti-cancer pro-drug activating enzyme capable of converting the pro-drug to its active form.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Hollinger et al., Proc. Natl. Acad. Sci. USA 90:6444-48 (1993).

The term "deplete," in the context of the effect of a 191P4D12 binding agent on 191P4D12-expressing cells, refers to a reduction in the number of or elimination of the 191P4D12-expressing cells.

The term "gene product" is used herein to indicate a peptide/protein or mRNA. For example, a "gene product of the invention" is sometimes referred to herein as a "cancer amino acid sequence", "cancer protein", "protein of a cancer listed in Table I", a "cancer mRNA", "mRNA of a cancer listed in Table I", etc. In one embodiment, the cancer protein is encoded by a nucleic acid of FIG. 1. The cancer protein can be a fragment, or alternatively, be the full-length protein encoded by nucleic acids of FIG. 1. In one embodiment, a cancer amino acid sequence is used to determine sequence identity or similarity. In another embodiment, the sequences are naturally occurring allelic variants of a protein encoded by a nucleic acid of FIG. 1. In another embodiment, the sequences are sequence variants as further described herein.

"Heteroconjugate" antibodies are useful in the present methods and compositions. As used herein, the term "heteroconjugate antibody" refers to two covalently joined antibodies. Such antibodies can be prepared using known methods in synthetic protein chemistry, including using crosslinking agents. See, e.g., U.S. Pat. No. 4,676,980.

The term "homolog" refers to a molecule which exhibits homology to another molecule, by for example, having sequences of chemical residues that are the same or similar at corresponding positions.

In one embodiment, the antibody provided herein is a "human antibody." As used herein, the term "human antibody" refers to an antibody in which essentially the entire sequences of the light chain and heavy chain sequences, including the complementary determining regions (CDRs), are from human genes. In one embodiment, human monoclonal antibodies are prepared by the trioma technique, the human B-cell technique (see, e.g., Kozbor, et al., Immunol. Today 4: 72 (1983), EBV transformation technique (see, e.g., Cole et al. *Monoclonal Antibodies And Cancer Therapy*

77-96 (1985)), or using phage display (see, e.g., Marks et al., *J. Mol. Biol.* 222:581 (1991)). In a specific embodiment, the human antibody is generated in a transgenic mouse. Techniques for making such partially to fully human antibodies are known in the art and any such techniques can be used. According to one particularly preferred embodiment, fully human antibody sequences are made in a transgenic mouse engineered to express human heavy and light chain antibody genes. An exemplary description of preparing transgenic mice that produce human antibodies found in Application No. WO 02/43478 and U.S. Pat. No. 6,657,103 (Abgenix) and its progeny. B cells from transgenic mice that produce the desired antibody can then be fused to make hybridoma cell lines for continuous production of the antibody. See, e.g., U.S. Pat. Nos. 5,569,825; 5,625,126; 5,633,425; 5,661,016; and 5,545,806; and Jakobovits, Adv. Drug Del. Rev. 31:33-42 (1998); Green, et al., J. Exp. Med. 188:483-95 (1998).

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. See e.g., Cabilly U.S. Pat. No. 4,816,567; Queen et al. (1989) Proc. Nat'l Acad. Sci. USA 86:10029-10033; and *Antibody Engineering: A Practical Approach* (Oxford University Press 1996).

The terms "inhibit" or "inhibition" of as used herein means to reduce by a measurable amount, or to prevent entirely.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the 191P4D12 genes or that encode polypeptides other than 191P4D12 gene product or fragments thereof. A skilled artisan can readily employ nucleic acid isolation procedures to obtain an isolated 191P4D12 polynucleotide. A protein is said to be "isolated," for example, when physical, mechanical or chemical methods are employed to remove the 191P4D12 proteins from cellular constituents that are normally associated with the protein. A skilled artisan can readily employ standard purification methods to obtain an isolated 191P4D12 protein. Alternatively, an isolated protein can be prepared by chemical means.

Suitable "labels" include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. In addition, the antibodies provided herein can be useful as the antigen-binding component of fluorobodies. See e.g., Zeytun et al., *Nat. Biotechnol.* 21:1473-79 (2003).

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic cancer" and "metastatic disease" mean cancers that have spread to regional lymph nodes or to distant sites, and are meant to include stage D disease under the AUA system and stage TxNxM+ under the TNM system.

The term "modulator" or "test compound" or "drug candidate" or grammatical equivalents as used herein describe any molecule, e.g., protein, oligopeptide, small organic molecule, polysaccharide, polynucleotide, etc., to be tested for the capacity to directly or indirectly alter the cancer phenotype or the expression of a cancer sequence, e.g., a nucleic acid or protein sequences, or effects of cancer sequences (e.g., signaling, gene expression, protein interaction, etc.) In one aspect, a modulator will neutralize the effect of a cancer protein of the invention. By "neutralize" is meant that an activity of a protein is inhibited or blocked, along with the consequent effect on the cell. In another aspect, a modulator will neutralize the effect of a gene, and its corresponding protein, of the invention by normalizing levels of said protein. In preferred embodiments, modulators alter expression profiles, or expression profile nucleic acids or proteins provided herein, or downstream effector pathways. In one embodiment, the modulator suppresses a cancer phenotype, e.g. to a normal tissue fingerprint. In another embodiment, a modulator induced a cancer phenotype. Generally, a plurality of assay mixtures is run in parallel with different agent concentrations to obtain a differential response to the various concentrations. Typically, one of these concentrations serves as a negative control, i.e., at zero concentration or below the level of detection.

Modulators, drug candidates, or test compounds encompass numerous chemical classes, though typically they are organic molecules, preferably small organic compounds having a molecular weight of more than 100 and less than about 2,500 Daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Modulators also comprise biomolecules such as peptides, saccharides, fatty acids, steroids, purines, pyrimidines, derivatives, structural analogs or combinations thereof. Particularly preferred are peptides. One class of modulators are peptides, for example of from about five to about 35 amino acids, with from about five to about 20 amino acids being preferred, and from about 7 to about 15 being particularly preferred. Preferably, the cancer modulatory protein is soluble, includes a non-transmembrane region, and/or, has an N-terminal Cys to aid in solubility. In one embodiment, the C-terminus of the fragment is kept as a free acid and the N-terminus is a free amine to aid in coupling, i.e., to cysteine. In one embodiment, a cancer protein of the invention is conjugated to an immunogenic agent as discussed herein. In one embodiment, the cancer protein is conjugated to BSA. The peptides of the invention, e.g., of preferred lengths, can be linked to each other or to other amino acids to create a longer peptide/protein. The modulatory peptides can be digests of naturally occurring proteins as is outlined above, random peptides, or "biased" random peptides. In a preferred embodiment, peptide/protein-based modulators are antibodies, and fragments thereof, as defined herein.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. In one embodiment, the polyclonal antibody contains a plurality of monoclonal antibodies with different epitope specificities, affinities, or avidities within a single antigen that contains multiple antigenic epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352: 624-628 (1991) and Marks et al., J. Mol. Biol. 222: 581-597 (1991), for example. These monoclonal antibodies will usually bind with at least a Kd of about 1 µM, more usually at least about 300 nM, typically at least about 30 nM, preferably at least about 10 nM, more preferably at least about 3 nM or better, usually determined by ELISA.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T), as shown for example in FIG. 1, can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

A "recombinant" DNA or RNA molecule is a DNA or RNA molecule that has been subjected to molecular manipulation in vitro.

As used herein, the term "single-chain Fv" or "scFv" or "single chain" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun, The Pharmacology Of Monoclonal Antibodies, vol. 113, Rosenburg and Moore eds. Springer-Verlag, New York, pp. 269-315 (1994).

As used herein, the terms "specific", "specifically binds" and "binds specifically" refer to the selective binding of the antibody to the target antigen epitope. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific. In one embodiment, a specific antibody is one that only binds the 191P4D12 antigen, but does not bind to the irrelevant antigen. In another embodiment, a specific antibody is one that binds human 191P4D12 antigen but does not bind a non-human 191P4D12 antigen with 70%, 75%, 80%, 85%, 90%, 91%, 92%, 93%, 94%, 95%, 96%, 97%, 98%, 99% or greater amino acid homology with the 191P4D12 antigen. In another embodiment, a specific antibody is one that binds human 191P4D12 antigen and binds murine 191P4D12 antigen, but with a higher degree of binding the human antigen. In another embodiment, a specific antibody is one that binds human 191P4D12 antigen and binds primate 191P4D12 antigen, but with a higher degree of binding the human antigen. In another embodiment, the specific antibody binds to human 191P4D12 antigen and any non-human 191P4D12 antigen, but with a higher degree of binding the human antigen or any combination thereof.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred but albeit not a requirement for a treatment act.

The term "variant" refers to a molecule that exhibits a variation from a described type or norm, such as a protein that has one or more different amino acid residues in the corresponding position(s) of a specifically described protein (e.g. the 191P4D12 protein shown in FIG. 1.) An analog is an example of a variant protein. Splice isoforms and single nucleotides polymorphisms (SNPs) are further examples of variants.

The "191P4D12 proteins" and/or "191P4D12 related proteins" of the invention include those specifically identified herein (see, FIG. 1), as well as allelic variants, conservative substitution variants, analogs and homologs that can be isolated/generated and characterized without undue experimentation following the methods outlined herein or readily available in the art. Fusion proteins that combine parts of different 191P4D12 proteins or fragments thereof, as well as fusion proteins of a 191P4D12 protein and a heterologous polypeptide are also included. Such 191P4D12 proteins are collectively referred to as the 191P4D12-related proteins, the proteins of the invention, or 191P4D12. The term "191P4D12-related protein" refers to a polypeptide fragment or a 191P4D12 protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 330, 335, 339 or more amino acids.

II.) 191P4D12 Antibodies

Another aspect of the invention provides antibodies that bind to 191P4D12-related proteins (See FIG. 1). In one embodiment, the antibody that binds to 191P4D12-related proteins is an antibody that specifically binds to 191P4D12 protein comprising amino acid sequence of SEQ ID NO.: 2. The antibody that specifically binds to 191P4D12 protein comprising amino acid sequence of SEQ ID NO.: 2 includes antibodies that can bind to other 191P4D12-related proteins. For example, antibodies that bind 191P4D12 protein comprising amino acid sequence of SEQ ID NO.:2 can bind 191P4D12-related proteins such as 191P4D12 variants and the homologs or analogs thereof.

191P4D12 antibodies of the invention are particularly useful in cancer (see, e.g., Table I) prognostic assays, imaging, and therapeutic methodologies. Similarly, such antibodies are useful in the treatment, and/or prognosis of colon and other cancers, to the extent 191P4D12 is also expressed or overexpressed in these other cancers. Moreover, intracellularly expressed antibodies (e.g., single chain antibodies) are therapeutically useful in treating cancers in which the expression of 191P4D12 is involved, such as advanced or metastatic colon cancers or other advanced or metastatic cancers.

Various methods for the preparation of antibodies, specifically monoclonal antibodies, are well known in the art. For example, antibodies can be prepared by immunizing a suitable mammalian host using a 191P4D12-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of 191P4D12 can also be used, such as a 191P4D12 GST-fusion protein. In a particular embodiment, a GST fusion protein comprising all or most of the amino acid sequence of FIG. 1 is produced, and then used as an immunogen to generate appropriate antibodies. In another embodiment, a 191P4D12-related protein is synthesized and used as an immunogen.

In addition, naked DNA immunization techniques known in the art are used (with or without purified 191P4D12-related protein or 191P4D12 expressing cells) to generate an immune response to the encoded immunogen (for review, see Donnelly et al., 1997, Ann. Rev. Immunol. 15: 617-648).

The amino acid sequence of a 191P4D12 protein as shown in FIG. 1 can be analyzed to select specific regions of the 191P4D12 protein for generating antibodies. For example, hydrophobicity and hydrophilicity analyses of a 191P4D12 amino acid sequence are used to identify hydrophilic regions in the 191P4D12 structure. Regions of a 191P4D12 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Hydrophilicity profiles can be generated using the method of Hopp, T. P. and Woods, K. R., 1981, Proc. Natl. Acad. Sci. U.S.A. 78:3824-3828. Hydropathicity profiles can be generated using the method of Kyte, J. and Doolittle, R. F., 1982, J. Mol. Biol. 157:105-132. Percent (%) Accessible Residues profiles can be generated using the method of Janin J., 1979, Nature 277:491-492. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each region identified by any of these programs or methods is within the scope of the present invention. Preferred methods for the generation of 191P4D12 antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a 191P4D12 immunogen is often conducted by injection over a suitable time period and with use of a suitable adjuvant, as is understood in the art. During the immunization schedule, titers of antibodies can be taken to determine adequacy of antibody formation.

191P4D12 monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a 191P4D12-related protein. When the appropriate immortalized cell culture is identified, the cells can be expanded and antibodies produced either from in vitro cultures or from ascites fluid.

The antibodies or fragments of the invention can also be produced by recombinant means. Regions that bind specifically to the desired regions of a 191P4D12 protein can also be produced in the context of chimeric or complementarity-determining region (CDR) grafted antibodies of multiple species origin. Humanized or human 191P4D12 antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

In a preferred embodiment, the antibodies of the present invention comprise fully human 191P4D12 antibodies (191P4D12 MAbs). Various methods in the art provide means for producing fully human 191P4D12 MAbs. For example, a preferred embodiment provides for techniques using transgenic mice, inactivated for antibody production, engineered with human heavy and light chains loci referred to as Xenomouse (Amgen Fremont, Inc.). An exemplary description of preparing transgenic mice that produce human antibodies can be found in U.S. Pat. No. 6,657,103. See, also, U.S. Pat. Nos. 5,569,825; 5,625,126; 5,633,425; 5,661, 016; and 5,545,806; and Mendez, et. al. Nature Genetics, 15: 146-156 (1998); Kellerman, S. A. & Green, L. L., Curr. Opin. Biotechnol 13, 593-597 (2002).

In addition, human antibodies of the invention can be generated using the HuMAb mouse (Medarex, Inc.) which contains human immunoglobulin gene miniloci that encode unrearranged human heavy (mu and gamma) and kappa light chain immunoglobulin sequences, together with targeted mutations that inactivate the endogenous mu and kappa chain loci (see e.g., Lonberg, et al. (1994) Nature 368(6474): 856-859).

In another embodiment, fully human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM mice", such mice are described in Tomizuka et al. (2000) Proc. Natl. Acad. Sci. USA 97:722-727 and PCT Publication WO 02/43478 to Tomizuka, et al.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In a preferred embodiment, an 191P4D12 MAbs of the invention comprises heavy and light chain variable regions of an antibody designated Ha22-2(2,4)6.1 produced by a hybridoma deposited under the American Type Culture Collection (ATCC) Accession No.: PTA-11267 (See, FIG. 3), or heavy and light variable regions comprising amino acid sequences that are homologous to the amino acid sequences of the heavy and light chain variable regions of Ha22-2(2,4)6.1, and wherein the antibodies retain the desired functional properties of the 191P4D12 MAbs of the invention. The heavy chain variable region of Ha22-2(2,4)6.1 consists of the amino acid sequence ranging from $20^{th}$ E residue to the $136^{th}$ S residue of SEQ ID NO:7, and the light chain variable region of Ha22-2(2,4)6.1 consists of the amino acid sequence ranging from $23^{rd}$ D residue to the $130^{th}$ R residue of SEQ ID NO:8. As the constant region of the antibody of the invention, any subclass of constant region can be chosen. In one embodiment, human IgG1 constant region as the heavy chain constant region and human Ig kappa constant region as the light chain constant region can be used.

For example, the invention provides an isolated monoclonal antibody, or antigen binding portion thereof, comprising a heavy chain variable region and a light chain variable region, wherein:

(a) the heavy chain variable region comprises an amino acid sequence that is at least 80% homologous to heavy chain variable region amino acid sequence set forth in FIG. 3; and (b) the light chain variable region comprises an amino acid sequence that is at least 80% homologous to the light chain variable region amino acid sequence set forth in FIG. 3.

In other embodiments, the $V_H$ and/or $V_L$ amino acid sequences may be 85%, 86%, 87%, 88%, 89%, 90%, 91%, 92%, 93%, 94%, 95%, 96%, 97%, 98% or 99% homologous to the $V_H$ and $V_L$ sequences set forth in FIG. 3.

In another embodiment, the invention provides an isolated monoclonal antibody, or antigen binding portion thereof, comprising a humanized heavy chain variable region and a humanized light chain variable region, wherein:

(a) the heavy chain variable region comprises complementarity determining regions (CDRs) having the amino acid sequences of the heavy chain variable region CDRs set forth in FIG. 3;

(b) the light chain variable region comprises CDRs having the amino acid sequences of the light chain variable region CDRs set forth in FIG. 3.

Engineered antibodies of the invention include those in which modifications have been made to framework residues within $V_H$ and/or $V_L$ (e.g. to improve the properties of the antibody). Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis (e.g., "backmutated" from leucine to methionine). Such "backmutated" antibodies are also intended to be encompassed by the invention.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 2003/0153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, a 191P4D12 MAb of the invention may be chemically modified (e.g., one or more chemical moieties can be attached to the antibody) or be modified to alter its glycosylation, again to alter one or more functional properties of the MAb. Each of these embodiments is described in further detail below.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the 191P4D12 MAb.

In another embodiment, the Fc hinge region of an antibody is mutated to decrease the biological half life of the 191P4D12 MAb. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the 191P4D12 MAb is modified to increase its biological half life. Various approaches are possible. For example, mutations can be introduced as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the 191P4D12 MAb. For example, one or more amino acids selected from amino acid specific residues can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

Reactivity of 191P4D12 antibodies with a 191P4D12-related protein can be established by a number of well known means, including Western blot, immunoprecipitation, ELISA, and FACS analyses using, as appropriate, 191P4D12-related proteins, 191P4D12-expressing cells or extracts thereof. A 191P4D12 antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 191P4D12 epitopes are generated using methods generally known in the art. Homodimeric antibodies can also be generated by cross-linking techniques known in the art (e.g., Wolff et al., Cancer Res. 53: 2560-2565).

In yet another preferred embodiment, the 191P4D12 MAb of the invention is an antibody comprising heavy and light chain of an antibody designated Ha22-2(2,4)6.1. The heavy chain of Ha22-2(2,4)6.1 consists of the amino acid sequence ranging from $20^{th}$ E residue to the $466^{th}$ K residue of SEQ ID NO:7 and the light chain of Ha22-2(2,4)6.1 consists of amino acid sequence ranging from $23^{rd}$ D residue to the $236^{th}$ C residue of SEQ ID NO:8 sequence. The sequence of which is set forth in FIG. 2 and FIG. 3. In a preferred embodiment, Ha22-2(2,4)6.1 is conjugated to a cytotoxic agent.

The hybridoma producing the antibody designated Ha22-2(2,4)6.1 was sent (via Federal Express) to the American Type Culture Collection (ATCC), P.O. Box 1549, Manassas, Va. 20108 on 18 Aug. 2010 and assigned Accession number PTA-11267.

III.) Antibody-Drug Conjugates Generally

In another aspect, the invention provides antibody-drug conjugates (ADCs), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In another aspect, the invention further provides methods of using the ADCs. In one aspect, an ADC comprises any of the herein 191P4D12 MAbs covalently attached to a cytotoxic agent or a detectable agent.

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986): 603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.$), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may assert their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Examples of antibody drug conjugates are, ZEVALIN® (ibritumomab tiuxetan, Biogen/Idec) which is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69).

Additionally, MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001).

In addition, Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others.

Additionally, MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors.

Finally, the auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Further, chemotherapeutic agents useful in the generation of ADCs are described herein. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al (1987) Science, 238:1098. Carbon-14-labeled 1-isothiocyanatobenzyl-3-methyldiethylene triaminepentaacetic acid (MX-DTPA) is an exemplary chelating agent for conjugation of radionucleotide to the antibody (WO94/11026).

Conjugates of an antibody and one or more small molecule toxins, such as a calicheamicin, maytansinoids, dolastatins, auristatins, a trichothecene, and CC1065, and the derivatives of these toxins that have toxin activity, are also contemplated herein.

III(A). Maytansinoids

Maytansine compounds suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides) and those having modifications at other positions.

Exemplary maytansinoid drug moieties also include those having modifications such as: C-9-SH (U.S. Pat. No. 4,424,219) (prepared by the reaction of maytansinol with $H_2S$ or $P_2S_5$); C-14-alkoxymethyl(demethoxy/$CH_2$ OR)(U.S. Pat. No. 4,331,598); C-14-hydroxymethyl or acyloxymethyl ($CH_2OH$ or $CH_2OAc$) (U.S. Pat. No. 4,450,254) (prepared from *Nocardia*); C-15-hydroxy/acyloxy (U.S. Pat. No. 4,364,866) (prepared by the conversion of maytansinol by *Streptomyces*); C-15-methoxy (U.S. Pat. Nos. 4,313,946 and 4,315,929) (isolated from Trewia nudlflora); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol).

ADCs containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference. Liu et al., Proc. Natl. Acad. Sci. USA 93:8618-8623 (1996) described ADCs comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe ADCs in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

III(B). Auristatins and Dolastatins

In some embodiments, the ADC comprises an antibody of the invention conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Senter et al, Proceedings of the American Association for Cancer Research, Volume 45, Abstract Number 623, presented Mar. 28, 2004 and described in United States Patent Publication No. 2005/0238649, the disclosure of which is expressly incorporated by reference in its entirety.

An exemplary auristatin embodiment is MMAE (wherein the wavy line indicates the covalent attachment to a linker (L) of an antibody drug conjugate).

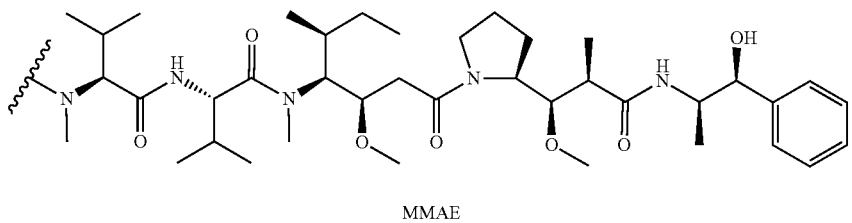 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

Another exemplary auristatin embodiment is MMAF, wherein the wavy line indicates the covalent attachment to a linker (L) of an antibody drug conjugate (US 2005/0238649):

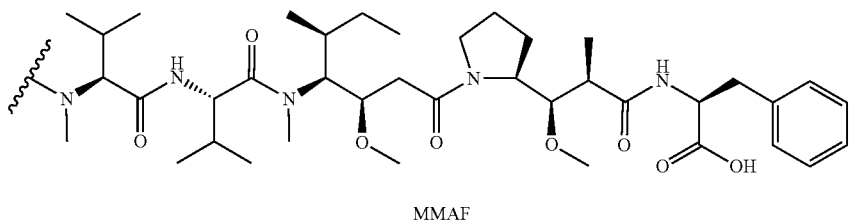

MMAF

Additional exemplary embodiments comprising MMAE or MMAF and various linker components (described further herein) have the following structures and abbreviations (wherein Ab means antibody, S is a sulfur of the antibody, and p is 1 to about 8):

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lake, "The Peptides", volume 1, pp 76-136, 1965, Academic Press) that is well known in the field of peptide chemistry. The auristatin/dolastatin drug moieties may be prepared according to the methods of: U.S. Pat. Nos. 5,635,483; 5,780,588; Pettit et al

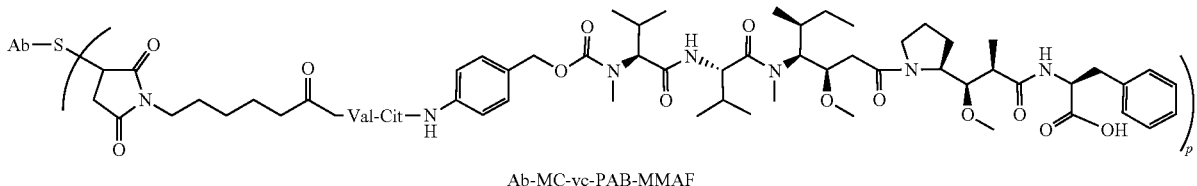

Ab-MC-vc-PAB-MMAF

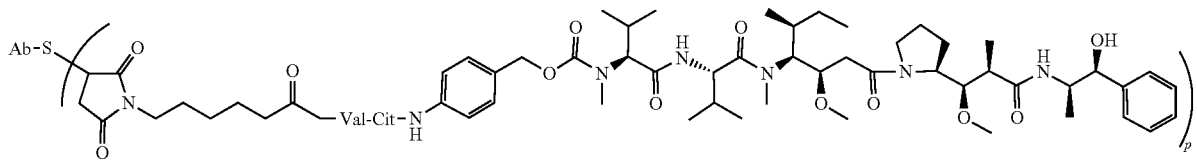

Ab-MC-vc-PAB-MMAE

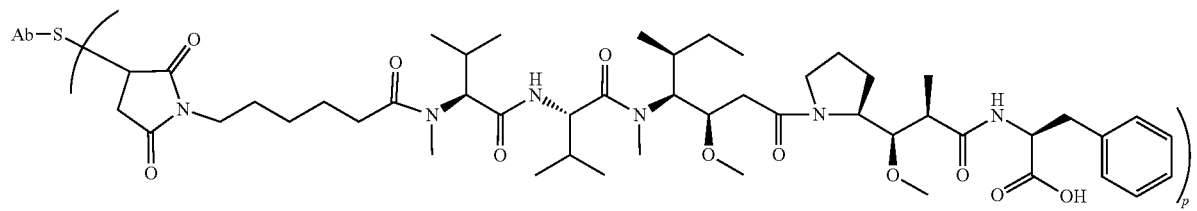

Ab-MC-MMAF (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat Biotechnol 21(7):778-784.

III(C). Calicheamicin

In other embodiments, the ADC comprises an antibody of the invention conjugated to one or more calicheamicin molecules. The calicheamicin family of antibiotics are capable of producing double-stranded DNA breaks at subpicomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

III(D). Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

The present invention further contemplates an ADC formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

IV.) Antibody-Drug Conjugate Compounds which Bind 191P4D12

The present invention provides, inter alia, antibody-drug conjugate compounds for targeted delivery of drugs. The inventors have made the discovery that the antibody-drug conjugate compounds have potent cytotoxic and/or cytostatic activity against cells expressing 191P4D12. The antibody-drug conjugate compounds comprise an Antibody unit covalently linked to at least one Drug unit. The Drug units can be covalently linked directly or via a Linker unit (LU).

In some embodiments, the antibody drug conjugate compound has the following formula:

$$L-(LU-D)_p \quad (I)$$

or a pharmaceutically acceptable salt or solvate thereof; wherein:
L is the Antibody unit, e.g., 191P4D12 MAb of the present invention, and (LU-D) is a Linker unit-Drug unit moiety, wherein:
LU- is a Linker unit, and
-D is a drug unit having cytostatic or cytotoxic activity against a target cell; and
p is an integer from 1 to 20.

In some embodiments, p ranges from 1 to 10, 1 to 9, 1 to 8, 1 to 7, 1 to 6, 1 to 5, 1 to 4, 1 to 3, or 1 to 2. In some embodiments, p ranges from 2 to 10, 2 to 9, 2 to 8, 2 to 7, 2 to 6, 2 to 5, 2 to 4 or 2 to 3. In other embodiments, p is 1, 2, 3, 4, 5 or 6. In some embodiments, p is 2 or 4.

In some embodiments, the antibody drug conjugate compound has the following formula:

$$L-(A_a-W_w-Y_y-D)_p \quad (II)$$

or a pharmaceutically acceptable salt or solvate thereof, wherein:
L is the Antibody unit, e.g., 191P4D12 MAb; and
-$A_a$-$W_w$—$Y_y$— is a Linker unit (LU), wherein:
-A- is a Stretcher unit,
a is 0 or 1,
each —W— is independently an Amino Acid unit,
w is an integer ranging from 0 to 12,
—Y— is a self-immolative spacer unit,
y is 0, 1 or 2;
-D is a drug units having cytostatic or cytotoxic activity against the target cell; and
p is an integer from 1 to 20.

In some embodiments, a is 0 or 1, w is 0 or 1, and y is 0, 1 or 2. In some embodiments, a is 0 or 1, w is 0 or 1, and y is 0 or 1. In some embodiments, p ranges from 1 to 10, 1 to 9, 1 to 8, 1 to 7, 1 to 6, 1 to 5, 1 to 4, 1 to 3, or 1 to 2. In some embodiments, p ranges from 2 to 8, 2 to 7, 2 to 6, 2 to 5, 2 to 4 or 2 to 3. In other embodiments, p is 1, 2, 3, 4, 5 or 6. In some embodiments, p is 2 or 4. In some embodiments, when w is not zero, y is 1 or 2. In some embodiments, when w is 1 to 12, y is 1 or 2. In some embodiments, w is 2 to 12 and y is 1 or 2. In some embodiments, a is 1 and w and y are 0.

For compositions comprising a plurality antibodies, the drug loading is represented by p, the average number of drug molecules per Antibody. Drug loading may range from 1 to 20 drugs (D) per Antibody. The average number of drugs per antibody in preparation of conjugation reactions may be characterized by conventional means such as mass spectroscopy, ELISA assay, and HPLC. The quantitative distribution of Antibody-Drug-Conjugates in terms of p may also be determined. In some instances, separation, purification, and characterization of homogeneous Antibody-Drug-conjugates where p is a certain value from Antibody-Drug-Conjugates with other drug loadings may be achieved by means such as reverse phase HPLC or electrophoresis. In exemplary embodiments, p is from 2 to 8.

The generation of Antibody-drug conjugate compounds can be accomplished by any technique known to the skilled artisan. Briefly, the Antibody-drug conjugate compounds comprise 191P4D12 MAb as the Antibody unit, a drug, and optionally a linker that joins the drug and the binding agent. In a preferred embodiment, the Antibody is 191P4D12 MAb comprising heavy and light chain variable regions of an antibody designated Ha22-2(2,4)6.1 described above. In more preferred embodiment, the Antibody is 191P4D12 MAb comprising heavy and light chain of an antibody designated Ha22-2(2,4)6.1 described above. A number of different reactions are available for covalent attachment of drugs and/or linkers to binding agents. This is often accomplished by reaction of the amino acid residues of the binding agent, e.g., antibody molecule, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates can also be used as coupling agents for covalently attaching drugs to binding agents. Other techniques are known to the skilled artisan and within the scope of the present invention.

In certain embodiments, an intermediate, which is the precursor of the linker, is reacted with the drug under appropriate conditions. In certain embodiments, reactive groups are used on the drug and/or the intermediate. The product of the reaction between the drug and the intermediate, or the derivatized drug, is subsequently reacted with the 191P4D12 MAb under appropriate conditions.

Each of the particular units of the Antibody-drug conjugate compounds is described in more detail herein. The synthesis and structure of exemplary Linker units, Stretcher units, Amino Acid units, self-immolative Spacer unit, and Drug units are also described in U.S. Patent Application Publication Nos. 2003-0083263, 2005-0238649 and 2005-0009751, each if which is incorporated herein by reference in its entirety and for all purposes.

V.) Linker Units

Typically, the antibody-drug conjugate compounds comprise a Linker unit between the drug unit and the antibody unit. In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Most typical are peptidyl linkers that are cleavable by enzymes that are present in 191P4D12-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker (SEQ ID NO:9)). Other examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the Val-Cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene), SPDB and SMPT. (See, e.g., Thorpe et al., 1987, Cancer Res. 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker unit is not cleavable and the drug is released by antibody degradation. (See U.S. Publication No. 2005/0238649 incorporated by reference herein in its entirety and for all purposes).

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of antibody-drug conjugate compound, are cleaved when the antibody-drug conjugate compound presents in an extracellular environment (e.g., in plasma). Whether a linker is not substantially sensitive to the extracellular environment can be determined, for example, by incubating with plasma the antibody-drug conjugate compound for a predetermined time period (e.g., 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent (i.e., in the milieu of the linker-therapeutic agent moiety of the antibody-drug conjugate compound as described herein). In yet other embodiments, the linker promotes cellular internalization when conjugated to both the auristatin compound and the 191P4D12 MAb.

A variety of exemplary linkers that can be used with the present compositions and methods are described in WO 2004-010957, U.S. Publication No. 2006/0074008, U.S. Publication No. 20050238649, and U.S. Publication No. 2006/0024317 (each of which is incorporated by reference herein in its entirety and for all purposes).

A "Linker unit" (LU) is a bifunctional compound that can be used to link a Drug unit and an Antibody unit to form an antibody-drug conjugate compound. In some embodiments, the Linker unit has the formula:

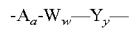

wherein: -A- is a Stretcher unit,
a is 0 or 1,
each —W— is independently an Amino Acid unit,
w is an integer ranging from 0 to 12,
—Y— is a self-immolative Spacer unit, and
y is 0, 1 or 2.

In some embodiments, a is 0 or 1, w is 0 or 1, and y is 0, 1 or 2. In some embodiments, a is 0 or 1, w is 0 or 1, and y is 0 or 1. In some embodiments, when w is 1 to 12, y is 1 or 2. In some embodiments, w is 2 to 12 and y is 1 or 2. In some embodiments, a is 1 and w and y are 0.

VI.) The Stretcher Unit

The Stretcher unit (A), when present, is capable of linking an Antibody unit to an Amino Acid unit (—W—), if present, to a Spacer unit (—Y—), if present; or to a Drug unit (-D). Useful functional groups that can be present on a 191P4D12 MAb (e.g. Ha22-2(2,4)6.1), either naturally or via chemical manipulation include, but are not limited to, sulfhydryl, amino, hydroxyl, the anomeric hydroxyl group of a carbohydrate, and carboxyl. Suitable functional groups are sulfhydryl and amino. In one example, sulfhydryl groups can be generated by reduction of the intramolecular disulfide bonds of a 191P4D12 MAb. In another embodiment, sulfhydryl groups can be generated by reaction of an amino group of a lysine moiety of a 191P4D12 MAb with 2-iminothiolane (Traut's reagent) or other sulfhydryl generating reagents. In certain embodiments, the 191P4D12 MAb is a recombinant antibody and is engineered to carry one or more lysines. In certain other embodiments, the recombinant 191P4D12 MAb is engineered to carry additional sulfhydryl groups, e.g., additional cysteines.

In one embodiment, the Stretcher unit forms a bond with a sulfur atom of the Antibody unit. The sulfur atom can be derived from a sulfhydryl group of an antibody. Representative Stretcher units of this embodiment are depicted within the square brackets of Formulas IIIa and IIIb, wherein L-, —W—, —Y—, -D, w and y are as defined above, and $R^{17}$ is selected from —$C_1$-$C_1$ alkylene-, alkenylene-, alkynylene-, carbocyclo-, ($C_1$-$C_8$ alkylene)-, O—($C_1$-$C_8$ alkenylene)-, alkynylene)-, -arylene-, alkylene-arylene-, alkenylene-arylene, alkynylene-arylene, -arylene-$C_1$-$C_{10}$ alkylene-, -arylene-$C_2$-$C_{10}$ alkenylene-, -arylene-$C_2$-$C_{10}$ alkynylene-, alkylene-(carbocyclo)-, alkenylene-(carbocyclo)-, —$C_2$-$C_{10}$ alkynylene-(carbocyclo)-, -(carbocyclo)-$C_1$-$C_{10}$ alkylene-, -(carbocyclo)-$C_2$-$C_{10}$ alkenylene-, -(carbocyclo)-$C_2$-$C_{10}$ alkynylene, -heterocyclo-, alkylene-(heterocyclo)-, —$C_2$-$C_{10}$ alkenylene-(heterocyclo)-, alkynylene-(heterocyclo)-, -(heterocyclo)-$C_1$-$C_{10}$ alkylene-, -(heterocyclo)-$C_2$-$C_{10}$ alkenylene-, -(heterocyclo)-$C_1$-$C_{10}$ alkynylene-, —$(CH_2CH_2O)_r$—, or —$(CH_2CH_2O)_r$—$CH_2$—, and r is an integer ranging from 1-10, wherein said alkyl, alkenyl, alkynyl, alkylene, alkenylene, alkynylene, aryl, carbocycle, carbocyclo, heterocyclo, and arylene radicals, whether alone or as part of another group, are optionally substituted. In some embodiments, said alkyl, alkenyl, alkynyl, alkylene, alkenylene, alkynyklene, aryl, carbocyle, carbocyclo, heterocyclo, and arylene radicals, whether alone or as part of another group, are unsubstituted. In some embodiments, $R^{17}$ is selected from —$C_1$-$C_{10}$ alkylene-, -carbocyclo-, —O—($C_1$-$C_8$ alkylene)-, -arylene-, alkylene-arylene-, -arylene-$C_1$-$C_{10}$ alkylene-, —$C_1$-$C_{10}$ alkylene-(carbocyclo)-, -(carbocyclo)-$C_1$-$C_{10}$ alkylene-, —$C_3$-$C_8$ heterocyclo-, alkylene-(heterocyclo)-, -(heterocyclo)-$C_1$-$C_{10}$ alkylene-, —$(CH_2CH_2O)_r$—, and —$(CH_2CH_2O)_r$—$CH_2$—; and r is an integer ranging from 1-10, wherein said alkylene groups are unsubstituted and the remainder of the groups are optionally substituted.

It is to be understood from all the exemplary embodiments that even where not denoted expressly, from 1 to 20 drug moieties can be linked to an Antibody (p=1-20).

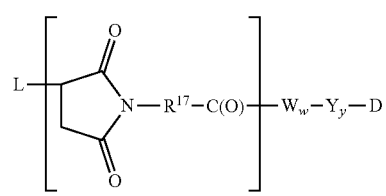

IIIa

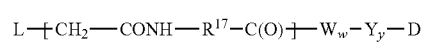

IIIb

An illustrative Stretcher unit is that of Formula IIIa wherein $R^{17}$ is —$(CH_2)_5$—:

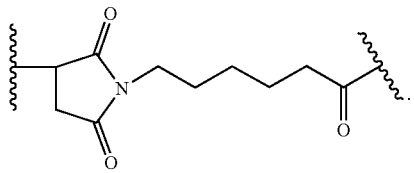 [SMILES: *C(=O)CCCCCN1C(=O)CC(*)C1=O]

Another illustrative Stretcher unit is that of Formula IIIa wherein $R^{17}$ is —$(CH_2CH_2O)_r$—$CH_2$—; and r is 2:

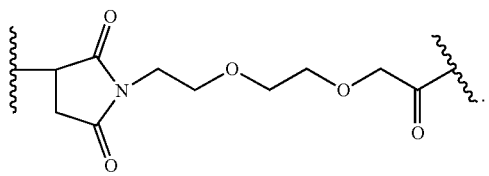 [SMILES: *C(=O)COCCOCCN1C(=O)CC(*)C1=O]

An illustrative Stretcher unit is that of Formula IIIa wherein $R^{17}$ is arylene- or arylene-$C_1$-$C_{10}$ alkylene-. In some embodiments, the aryl group is an unsubstituted phenyl group.

Still another illustrative Stretcher unit is that of Formula IIIb wherein $R^{17}$ is —$(CH_2)_5$—:

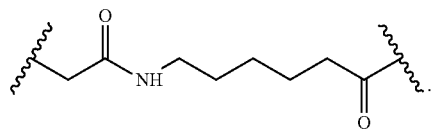 [SMILES: *CC(=O)NCCCCCC(*)=O]

In certain embodiments, the Stretcher unit is linked to the Antibody unit via a disulfide bond between a sulfur atom of the Antibody unit and a sulfur atom of the Stretcher unit. A representative Stretcher unit of this embodiment is depicted within the square brackets of Formula IV, wherein $R^{17}$, L-, —W—, —Y—, -D, w and y are as defined above.

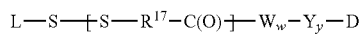
IV

It should be noted that throughout this application, the S moiety in the formula below refers to a sulfur atom of the Antibody unit, unless otherwise indicated by context.

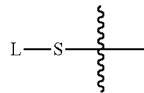

In yet other embodiments, the Stretcher contains a reactive site that can form a bond with a primary or secondary amino group of an Antibody. Examples of these reactive sites include, but are not limited to, activated esters such as succinimide esters, 4 nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas Va and Vb, wherein —$R^{17}$—, L-, —W—, —Y—, -D, w and y are as defined above;

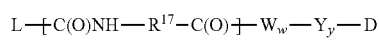
Va

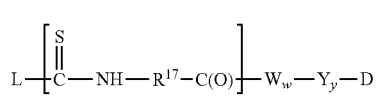
Vb

In some embodiments, the Stretcher contains a reactive site that is reactive to a modified carbohydrate's (—CHO) group that can be present on an Antibody. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko et al., 1991, *Bioconjugate Chem.* 2:133-41. Representative Stretcher units of this embodiment are depicted within the square brackets of Formulas VIa, VIb, and VIc, wherein —$R^{17}$—, L-, —W—, —Y—, -D, w and y are as defined as above.

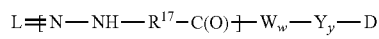
VIa

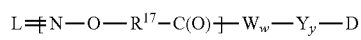
VIb

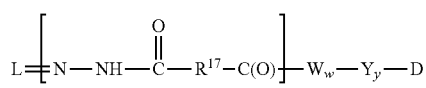
VIc

VII.) The Amino Acid Unit

The Amino Acid unit (—W—), when present, links the Stretcher unit to the Spacer unit if the Spacer unit is present, links the Stretcher unit to the Drug moiety if the Spacer unit is absent, and links the Antibody unit to the Drug unit if the Stretcher unit and Spacer unit are absent.

$W_w$— can be, for example, a monopeptide, dipeptide, tripeptide, tetrapeptide, pentapeptide, hexapeptide, heptapeptide, octapeptide, nonapeptide, decapeptide, undecapeptide or dodecapeptide unit. Each —W— unit independently has the formula denoted below in the square brackets, and w is an integer ranging from 0 to 12:

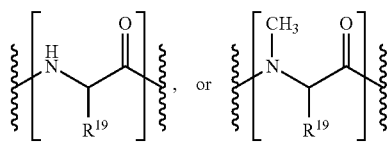

wherein $R^9$ is hydrogen, methyl, isopropyl, isobutyl, sec-butyl, benzyl, p-hydroxybenzyl, —$CH_2OH$, —$CH(OH)$ $CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC$ (=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl,

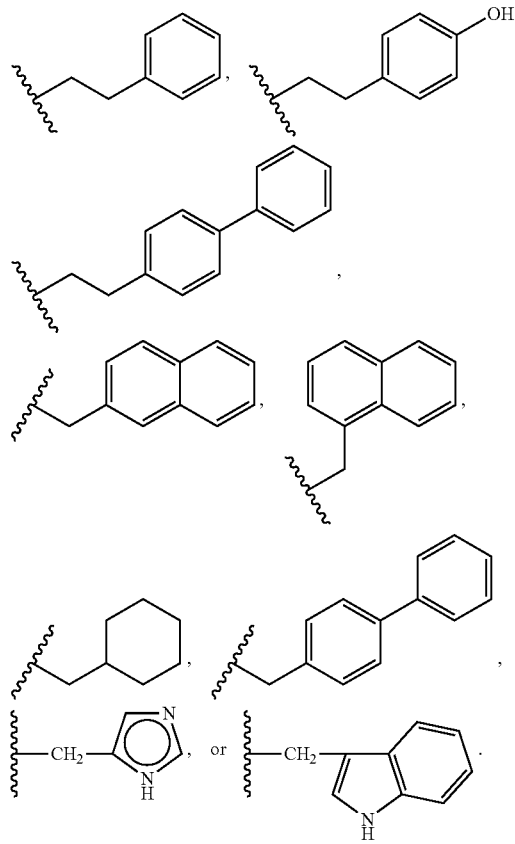

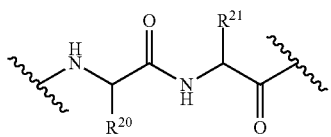

In some embodiments, the Amino Acid unit can be enzymatically cleaved by one or more enzymes, including a cancer or tumor-associated protease, to liberate the Drug unit (-D), which in one embodiment is protonated in vivo upon release to provide a Drug (D).

In certain embodiments, the Amino Acid unit can comprise natural amino acids. In other embodiments, the Amino Acid unit can comprise non-natural amino acids. Illustrative Ww units are represented by formulas (VII)-(IX):

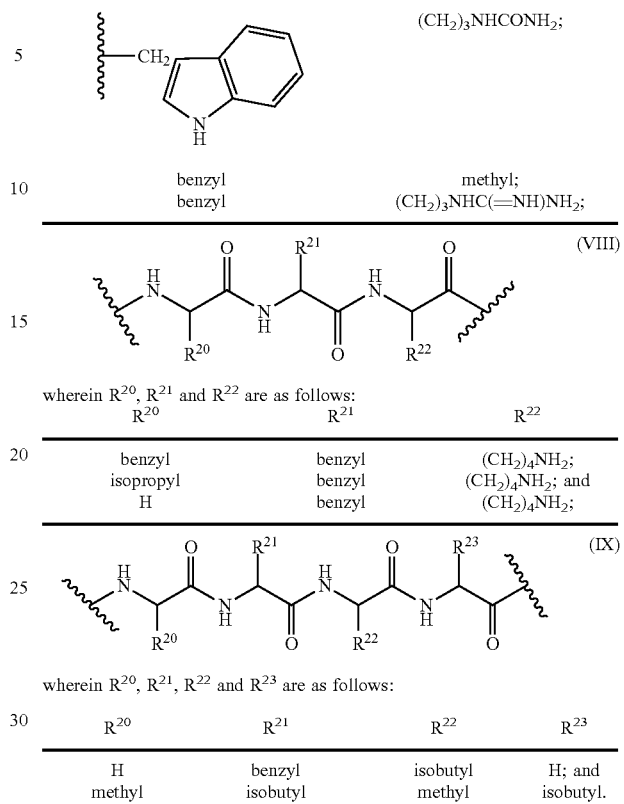

wherein R$^{20}$ and R$^{21}$ are as follows:

| R$^{20}$ | R$^{21}$ |
|---|---|
| Benzyl | (CH$_2$)$_4$NH$_2$; |
| methyl | (CH$_2$)$_4$NH$_2$; |
| isopropyl | (CH$_2$)$_4$NH$_2$; |
| isopropyl | (CH$_2$)$_3$NHCONH$_2$; |
| benzyl | (CH$_2$)$_3$NHCONH$_2$; |
| isobutyl | (CH$_2$)$_3$NHCONH$_2$; |
| sec-butyl | (CH$_2$)$_3$NHCONH$_2$; |
| CH$_2$-indolyl | (CH$_2$)$_3$NHCONH$_2$; |
| benzyl | methyl; |
| benzyl | (CH$_2$)$_3$NHC(=NH)NH$_2$; |

(VIII)

wherein R$^{20}$, R$^{21}$ and R$^{22}$ are as follows:

| R$^{20}$ | R$^{21}$ | R$^{22}$ |
|---|---|---|
| benzyl | benzyl | (CH$_2$)$_4$NH$_2$; |
| isopropyl | benzyl | (CH$_2$)$_4$NH$_2$; and |
| H | benzyl | (CH$_2$)$_4$NH$_2$; |

(IX)

wherein R$^{20}$, R$^{21}$, R$^{22}$ and R$^{23}$ are as follows:

| R$^{20}$ | R$^{21}$ | R$^{22}$ | R$^{23}$ |
|---|---|---|---|
| H | benzyl | isobutyl | H; and |
| methyl | isobutyl | methyl | isobutyl. |

Exemplary Amino Acid units include, but are not limited to, units of formula VII where: R$^{20}$ is benzyl and R$^{21}$ is —(CH$_2$)$_4$NH$_2$; R$^{20}$ is isopropyl and R$^{21}$ is —(CH$_2$)$_4$NH$_2$; or R$^{20}$ is isopropyl and R$^{21}$ is —(CH$_2$)$_3$NHCONH$_2$. Another exemplary Amino Acid unit is a unit of formula VIII wherein R$^{20}$ is benzyl, R$^{21}$ is benzyl, and R$^{22}$ is —(CH$_2$)$_4$NH$_2$.

Useful —W$_w$— units can be designed and optimized in their selectivity for enzymatic cleavage by a particular enzyme, for example, a tumor-associated protease. In one embodiment, a —W$_w$— unit is that whose cleavage is catalyzed by cathepsin B, C and D, or a plasmin protease.

In one embodiment, —W$_w$— is a dipeptide, tripeptide, tetrapeptide or pentapeptide. When R$^{19}$, R$^{20}$, R$^{21}$, R$^{22}$ or R$^{23}$ is other than hydrogen, the carbon atom to which R$^{19}$, R$^{20}$, R$^{21}$, R$^{22}$ or R$^{23}$ is attached is chiral.

Each carbon atom to which R$^{19}$, R$^{20}$, R$^{21}$, R$^{22}$ or R$^{23}$ is attached is independently in the (S) or (R) configuration.

In one aspect of the Amino Acid unit, the Amino Acid unit is valine-citrulline (vc or Val-Cit). In another aspect, the Amino Acid unit is phenylalanine-lysine (i.e., fk). In yet another aspect of the Amino Acid unit, the Amino Acid unit is N-methylvaline-citrulline. In yet another aspect, the Amino Acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine and isonepecotic acid.

VIII.) the Spacer Unit

The Spacer unit (—Y—), when present, links an Amino Acid unit to the Drug unit when an Amino Acid unit is present. Alternately, the Spacer unit links the Stretcher unit to the Drug unit when the Amino Acid unit is absent. The Spacer unit also links the Drug unit to the Antibody unit when both the Amino Acid unit and Stretcher unit are absent.

Spacer units are of two general types: non self-immolative or self-immolative. A non self-immolative Spacer unit is one in which part or all of the Spacer unit remains bound to the Drug moiety after cleavage, particularly enzymatic, of an Amino Acid unit from the antibody-drug conjugate. Examples of a non self-immolative Spacer unit include, but are not limited to a (glycine-glycine) Spacer unit and a glycine Spacer unit (both depicted in Scheme 1) (infra). When a conjugate containing a glycine-glycine Spacer unit or a glycine Spacer unit undergoes enzymatic cleavage via an enzyme (e.g., a tumor-cell associated-protease, a cancer-cell-associated protease or a lymphocyte-associated protease), a glycine-glycine-Drug moiety or a glycine-Drug moiety is cleaved from L-Aa-Ww-. In one embodiment, an independent hydrolysis reaction takes place within the target cell, cleaving the glycine-Drug moiety bond and liberating the Drug.

Scheme 1

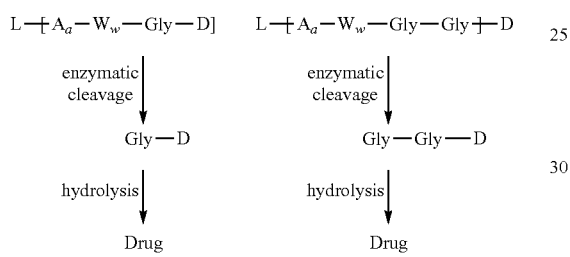

In some embodiments, a non self-immolative Spacer unit (—Y—) is -Gly-. In some embodiments, a non self-immolative Spacer unit (—Y—) is -Gly-Gly-.

In one embodiment, a Drug-Linker conjugate is provided in which the Spacer unit is absent (—$Y_y$— where y=0), or a pharmaceutically acceptable salt or solvate thereof.

Alternatively, a conjugate containing a self-immolative Spacer unit can release -D. As used herein, the term "self-immolative Spacer" refers to a bifunctional chemical moiety that is capable of covalently linking together two spaced chemical moieties into a stable tripartite molecule. It will spontaneously separate from the second chemical moiety if its bond to the first moiety is cleaved.

In some embodiments, —$Y_y$— is a p-aminobenzyl alcohol (PAB) unit (see Schemes 2 and 3) whose phenylene portion is substituted with $Q_m$ wherein Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; and m is an integer ranging from 0-4. The alkyl, alkenyl and alkynyl groups, whether alone or as part of another group, can be optionally substituted.

In some embodiments, —Y— is a PAB group that is linked to —$W_w$— via the amino nitrogen atom of the PAB group, and connected directly to -D via a carbonate, carbamate or ether group. Without being bound by any particular theory or mechanism, Scheme 2 depicts a possible mechanism of Drug release of a PAB group which is attached directly to -D via a carbamate or carbonate group as described by Toki et al., 2002, *J. Org. Chem.* 67:1866-1872.

Scheme 2

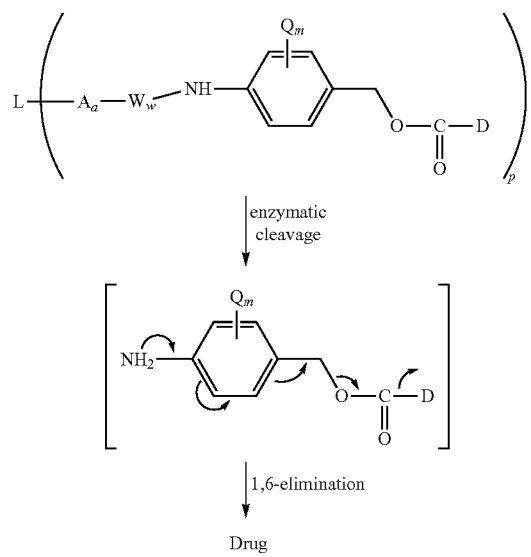

In Scheme 2, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; and p ranges from 1 to about 20. The alkyl, alkenyl and alkynyl groups, whether alone or as part of another group, can be optionally substituted.

Without being bound by any particular theory or mechanism, Scheme 3 depicts a possible mechanism of Drug release of a PAB group which is attached directly to -D via an ether or amine linkage, wherein D includes the oxygen or nitrogen group that is part of the Drug unit.

Scheme 3

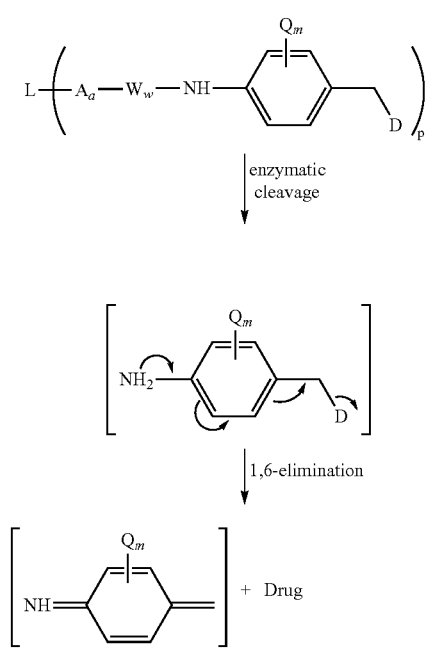

In Scheme 3, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; and p ranges from 1 to about 20. The alkyl, alkenyl and alkynyl groups, whether alone or as part of another group, can be optionally substituted.

Other examples of self-immolative spacers include, but are not limited to, aromatic compounds that are electronically similar to the PAB group such as 2-aminoimidazol-5-methanol derivatives (Hay et al., 1999, *Bioorg. Med. Chem. Lett.* 9:2237) and ortho or para-aminobenzylacetals. Spacers can be used that undergo cyclization upon amide bond hydrolysis, such as substituted and unsubstituted 4-aminobutyric acid amides (Rodrigues et al., 1995, *Chemistry Biology* 2:223), appropriately substituted bicyclo[2.2.1] and bicyclo[2.2.2] ring systems (Storm et al., 1972, *J. Amer. Chem. Soc.* 94:5815) and 2-aminophenylpropionic acid amides (Amsberry et al., 1990, *J. Org. Chem.* 55:5867). Elimination of amine-containing drugs that are substituted at the α-position of glycine (Kingsbury et al., 1984, *J Med. Chem.* 27:1447) are also examples of self-immolative spacers.

In one embodiment, the Spacer unit is a branched bis(hydroxymethyl)-styrene (BHMS) unit as depicted in Scheme 4, which can be used to incorporate and release multiple drugs.

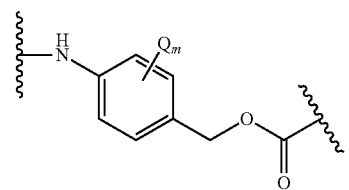

X wherein Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; and m is an integer ranging from 0-4. The alkyl, alkenyl and alkynyl groups, whether alone or as part of another group, can be optionally substituted.

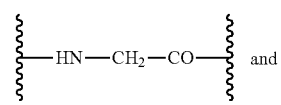

XI

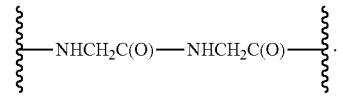

XII

Embodiments of the Formula I and II comprising antibody-drug conjugate compounds can include:

Scheme 4

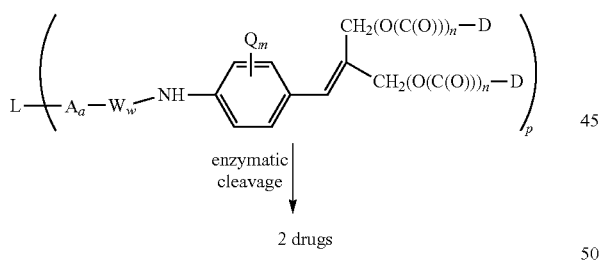

2 drugs

In Scheme 4, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; n is 0 or 1; and p ranges raging from 1 to about 20. The alkyl, alkenyl and alkynyl groups, whether alone or as part of another group, can be optionally substituted.

In some embodiments, the -D moieties are the same. In yet another embodiment, the -D moieties are different.

In one aspect, Spacer units (—$Y_y$—) are represented by Formulas (X)-(XII):

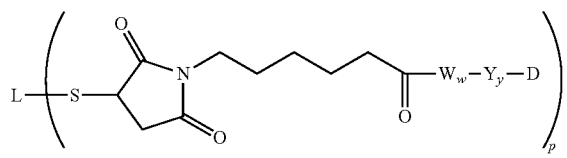

wherein w and y are each 0, 1 or 2, and,

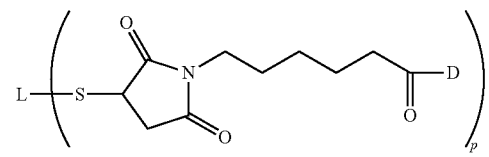

wherein w and y are each 0,

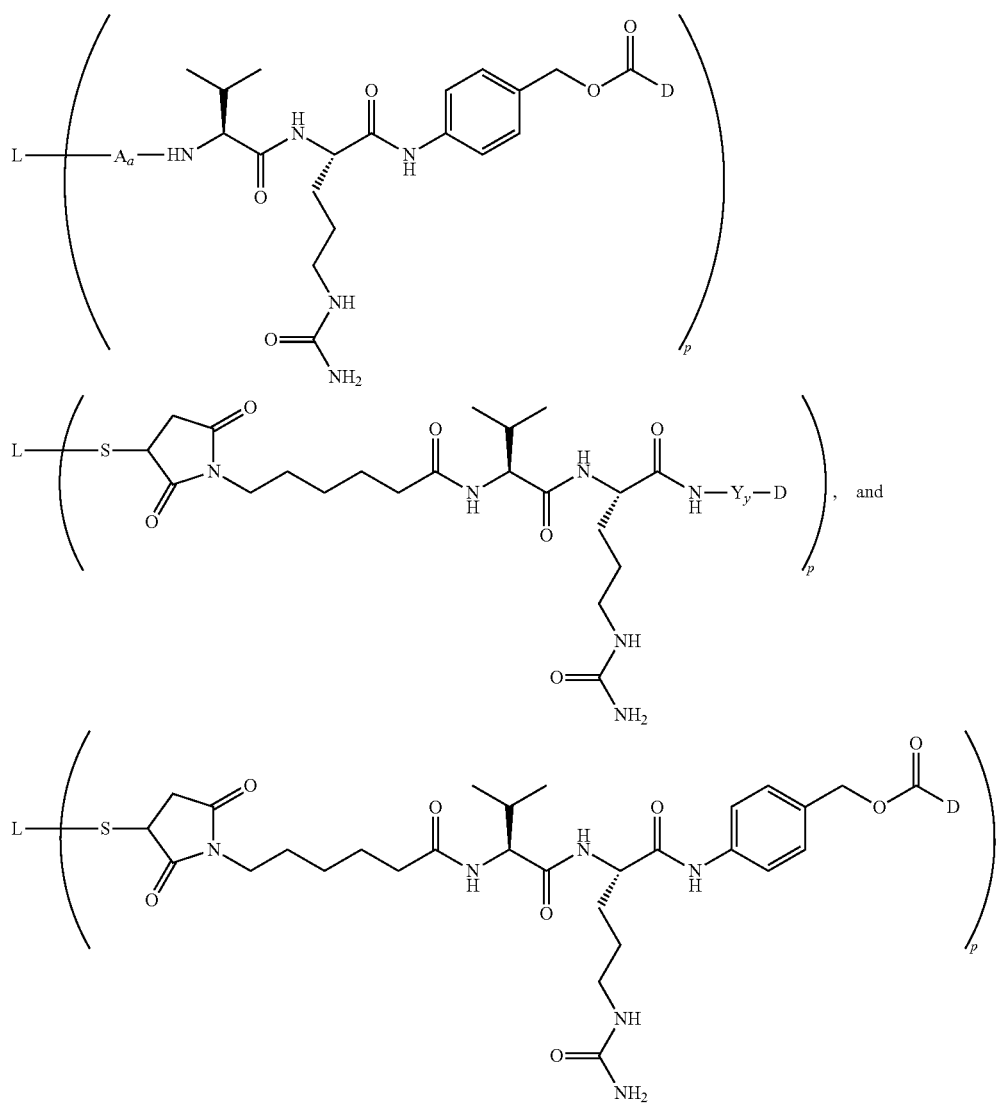

IX.) The Drug Unit

The Drug moiety (D) can be any cytotoxic, cytostatic or immunomodulatory (e.g., immunosuppressive) drug. D is a Drug unit (moiety) having an atom that can form a bond with the Spacer unit, with the Amino Acid unit, with the Stretcher unit or with the Antibody unit. In some embodiments, the Drug unit D has a nitrogen atom that can form a bond with the Spacer unit. As used herein, the terms "Drug unit" and "Drug moiety" are synonymous and used interchangeably.

Useful classes of cytotoxic, cytostatic, or immunomodulatory agents include, for example, antitubulin agents, DNA minor groove binders, DNA replication inhibitors, and alkylating agents.

In some embodiments, the Drug is an auristatin, such as auristatin E (also known in the art as a derivative of dolastatin-10) or a derivative thereof. The auristatin can be, for example, an ester formed between auristatin E and a keto acid. For example, auristatin E can be reacted with paraacetyl benzoic acid or benzoylvaleric acid to produce AEB and AEVB, respectively. Other typical auristatins include AFP, MMAF, and MMAE. The synthesis and structure of exemplary auristatins are described in U.S. Patent Application Publication No. 2003-0083263; International Patent Publication No. WO 04/010957, International Patent Publication No. WO 02/088172, and U.S. Pat. Nos. 7,498,298, 6,884,869, 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein in its entirety and for all purposes.

Auristatins have been shown to interfere with microtubule dynamics and nuclear and cellular division and have anticancer activity. Auristatins bind tubulin and can exert a cytotoxic or cytostatic effect on a 191P4D12-expressing cell. There are a number of different assays, known in the art, which can be used for determining whether an auristatin or resultant antibody-drug conjugate exerts a cytostatic or cytotoxic effect on a desired cell line.

Methods for determining whether a compound binds tubulin are known in the art. See, for example, Muller et al., *Anal. Chem* 2006, 78, 4390-4397; Hamel et al., *Molecular Pharmacology*, 1995 47: 965-976; and Hamel et al., *The*

*Journal of Biological Chemistry*, 1990 265:28, 17141-17149. For purposes of the present invention, the relative affinity of a compound to tubulin can be determined. Some preferred auristatins of the present invention bind tubulin with an affinity ranging from 10 fold lower (weaker affinity) than the binding affinity of MMAE to tubulin to 10 fold, 20 fold or even 100 fold higher (higher affinity) than the binding affinity of MMAE to tublin.

In some embodiments, -D is an auristatin of the formula $D_E$ or $D_F$:

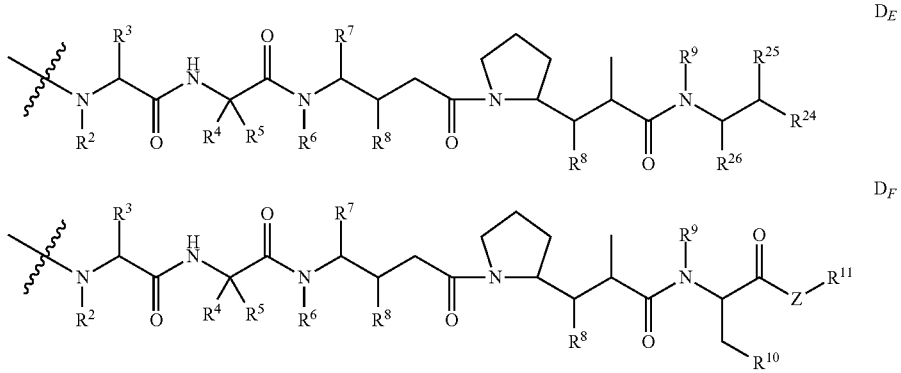

or a pharmaceutically acceptable salt or solvate form thereof;

wherein, independently at each location:

the wavy line indicates a bond;

$R^2$ is —$C_1$-$C_{20}$ alkyl, —$C_2$-$C_{20}$ alkenyl, or —$C_2$-$C_{20}$ alkynyl;

$R^3$ is —H, —$C_1$-$C_{20}$ alkyl, —$C_2$-$C_{20}$ alkenyl, —$C_2$-$C_{20}$ alkynyl, -carbocycle, —$C_1$-$C_{20}$ alkylene (carbocycle), —$C_2$-$C_{20}$ alkenylene(carbocycle), —$C_2$-$C_{20}$ alkynylene(carbocycle), -aryl, —$C_1$-$C_{20}$ alkylene(aryl), —$C_2$-$C_{20}$ alkenylene (aryl), —$C_2$-$C_{20}$ alkynylene(aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle);

$R^4$ is —H, —$C_1$-$C_{20}$ alkyl, —$C_2$-$C_{20}$ alkenyl, —$C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene(carbocycle), aryl, —$C_1$-$C_{20}$ alkylene(aryl), —$C_2$-$C_{20}$ alkenylene (aryl), —$C_2$-$C_{20}$ alkynylene(aryl), -heterocycle, —$C_1$-$C_{20}$ alkylene(heterocycle), —$C_2$-$C_{20}$ alkenylene(heterocycle), or —$C_2$-$C_{20}$ alkynylene(heterocycle);

$R^5$ is —H or —$C_1$-$C_8$ alkyl;

or $R^4$ and $R^5$ jointly form a carbocyclic ring and have the formula —$(CR^aR^b)_s$— wherein $R^a$ and $R^b$ are independently —H, —$C_1$-$C_{20}$ alkyl, —$C_2$-$C_{20}$ alkenyl, —$C_2$-$C_{20}$ alkynyl, or -carbocycle and s is 2, 3, 4, 5 or 6, $R^6$ is —H, —$C_1$-$C_{20}$ alkyl, —$C_2$-$C_{20}$ alkenyl, or —$C_2$-$C_{20}$ alkynyl;

$R^7$ is —H, —$C_1$-$C_{20}$ alkyl, —$C_2$-$C_{20}$ alkenyl, —$C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene(carbocycle), -aryl, —$C_1$-$C_{20}$ alkylene(aryl), —$C_2$-$C_{20}$ alkenylene (aryl), —$C_2$-$C_{20}$ alkynylene(aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle);

each $R^8$ is independently —H, —OH, —$C_1$-$C_{20}$ alkyl, —$C_2$-$C_{20}$ alkenyl, —$C_2$-$C_{20}$ alkynyl, —O—($C_1$-$C_{20}$ alkyl), —O—($C_2$-$C_{20}$ alkenyl), —O—($C_1$-$C_{20}$ alkynyl), or -carbocycle;

$R^9$ is —H, —$C_1$-$C_{20}$ alkyl, —$C_2$-$C_{20}$ alkenyl, or —$C_2$-$C_{20}$ alkynyl;

$R^{24}$ is -aryl, -heterocycle, or -carbocycle;

$R^{25}$ is —H, $C_1$-$C_{20}$ alkyl, —$C_2$-$C_{20}$ alkenyl, —$C_2$-$C_{20}$ alkynyl, -carbocycle, —O—($C_1$-$C_{20}$ alkyl), —O—($C_2$-$C_{20}$ alkenyl), —O—($C_2$-$C_{20}$ alkynyl), or $OR^{18}$ wherein $R^{18}$ is —H, a hydroxyl protecting group, or a direct bond where $OR^{18}$ represents =O;

$R^{26}$ is —H, —$C_1$-$C_{20}$ alkyl, —$C_2$-$C_{20}$ alkenyl, or —$C_2$-$C_{20}$ alkynyl, -aryl, -heterocycle, or -carbocycle;

$R^{10}$ is -aryl or -heterocycle;

Z is —O, —S, —NH, or —$NR^{12}$, wherein $R^{12}$ is —$C_1$-$C_{20}$ alkyl, —$C_2$-$C_{20}$ alkenyl, or —$C_2$-$C_{20}$ alkynyl;

$R^{11}$ is —H, —$C_1$-$C_{20}$ alkyl, —$C_2$-$C_{20}$ alkenyl, —$C_2$-$C_{20}$ alkynyl, -aryl, -heterocycle, —$(R^{13}O)_m$—$R^{14}$, or —$(R^{13}O)_m$—$CH(R^{15})_2$;

m is an integer ranging from 1-1000 or m=0-1000;

$R^{11}$ is —$C_2$-$C_{20}$ alkylene, —$C_2$-$C_{20}$ alkenylene, or —$C_2$-$C_{20}$ alkynylene;

$R^{14}$ is —H, —$C_1$-$C_{20}$ alkyl, —$C_2$-$C_{20}$ alkenyl, or —$C_2$-$C_{20}$ alkynyl;

each occurrence of $R^{15}$ is independently —H, —COOH, —$(CH_2)_n$-$N(R^{16})_2$, —$(CH_2)_n$—$SO_3H$, —$(CH_2)_n$—$SO_3$—$C_1$-$C_{20}$ alkyl, —$(CH_2)_n$—$SO_3$—$C_2$-$C_{20}$ alkenyl, or —$(CH_2)_n$—$SO_3$—$C_2$-$C_{20}$ alkynyl;

each occurrence of $R^{16}$ is independently —H, —$C_1$-$C_{20}$ alkyl, —$C_2$-$C_{20}$ alkenyl, —$C_2$-$C_{20}$ alkynyl or —$(CH_2)_n$—COOH; and n is an integer ranging from 0 to 6;

wherein said alkyl, alkenyl, alkynyl, alkylene, alkenylene, alkynyklene, aryl, carbocyle, and heterocycle radicals, whether alone or as part of another group, are optionally substituted.

Auristatins of the formula $D_E$ include those wherein said alkyl, alkenyl, alkynyl, alkylene, alkenylene, alkynyklene, aryl, carbocyle, and heterocycle radicals are unsubstituted.

Auristatins of the formula $D_E$ include those wherein the groups of $R^2$, $R^3$, $R^4$, $R^5$, $R^6$, $R^7$, $R^8$, and $R^9$ are unsubstituted and the groups of $R^{19}$, $R^{20}$ and $R^{21}$ are optionally substituted as described herein.

Auristatins of the formula DE include those wherein $R^2$ is $C_1$-$C_8$ alkyl;

$R^3$, $R^4$ and $R^7$ are independently selected from —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene(monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), $C_6$-$C_{10}$ aryl, —$C_1$-$C_{20}$ alkylene($C_6$-$C_{10}$ aryl), —$C_2$-

$C_{20}$ alkenylene($C_6$-$C_{10}$ aryl), —$C_2$-$C_{20}$ alkynylene($C_6$-$C_{10}$ aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle); wherein said alkyl, alkenyl, alkynyl, alkylene, alkenylene, alkynylene, carbocycle, aryl and heterocycle radicals are optionally substituted;

$R^5$ is —H;

$R^6$ is —$C_1$-$C_8$ alkyl;

each $R^8$ is independently selected from —OH, —O—($C_1$-$C_{20}$ alkyl), —O—($C_2$-$C_{20}$ alkenyl), or —O—($C_2$-$C_{20}$ alkynyl) wherein said alkyl, alkenyl, and alkynyl radicals are optionally substituted;

$R^9$ is —H or —$C_1$-$C_8$ alkyl;

$R^{24}$ is optionally substituted -phenyl;

$R^{25}$ is —$OR^{18}$; wherein $R^{18}$ is H, a hydroxyl protecting group, or a direct bond where $OR^{18}$ represents =O;

$R^{26}$ is selected from —H, —$C_1$-$C_{20}$ alkyl, —$C_2$-$C_{20}$ alkenyl, —$C_2$-$C_{20}$ alkynyl, or -carbocycle; wherein said alkyl, alkenyl, alkynyl and carbocycle radicals are optionally substituted; or a pharmaceutically acceptable salt or solvate form thereof.

Auristatins of the formula DE include those wherein $R^2$ is methyl;

$R^3$ is —H, —$C_1$-$C_8$ alkyl, —$C_2$-$C_8$ alkenyl, or $C_2$-$C_8$ alkynyl, wherein said alkyl, alkenyl and alkynyl radicals are optionally substituted;

$R^4$ is —H, —$C_1$-$C_8$ alkyl, —$C_2$-$C_8$ alkenyl, —$C_2$-$C_8$ alkynyl, monocyclic $C_3$-$C_6$ carbocycle, —$C_6$-$C_{10}$ aryl, —$C_1$-$C_8$ alkylene($C_6$-$C_{10}$ aryl), —$C_2$-$C_8$ alkenylene($C_6$-$C_{10}$ aryl), —$C_2$-$C_8$ alkynylene($C_6$-$C_{10}$ aryl), —$C_1$-$C_8$ alkylene (monocyclic $C_3$-$C_6$ carbocycle), —$C_2$-$C_8$ alkenylene (monocyclic $C_3$-$C_6$ carbocycle), —$C_2$-$C_8$ alkynylene(monocyclic $C_3$-$C_6$ carbocycle); wherein said alkyl, alkenyl, alkynyl, alkylene, alkenylene, alkynylene, aryl and carbocycle radicals whether alone or as part of another group are optionally substituted;

$R^5$ is —H;

$R^6$ is methyl;

$R^7$ is —$C_1$-$C_8$ alkyl, —$C_2$-$C_8$ alkenyl or —$C_2$-$C_8$ alkynyl;

each $R^8$ is methoxy;

$R^9$ is —H or —$C_1$-$C_8$ alkyl;

$R^{24}$ is -phenyl;

$R^{25}$ is —$OR^{18}$; wherein $R^{18}$ is H, a hydroxyl protecting group, or a direct bond where $OR^{18}$ represents =O;

$R^{26}$ is methyl;

or a pharmaceutically acceptable salt form thereof.

Auristatins of the formula DE include those wherein:

$R^2$ is methyl; $R^3$ is —H or —$C_1$-$C_3$ alkyl; $R^4$ is —$C_1$-$C_5$ alkyl; $R^5$ is —H; $R^6$ is methyl; $R^7$ is isopropyl or sec-butyl; $R^8$ is methoxy; $R^9$ is —H or —$C_1$-$C_8$ alkyl; $R^{24}$ is phenyl; $R^{25}$ is —$OR^{18}$; wherein $R^{18}$ is —H, a hydroxyl protecting group, or a direct bond where $OR^{18}$ represents =O; and $R^{26}$ is methyl; or a pharmaceutically acceptable salt or solvate form thereof.

Auristatins of the formula DE include those wherein:

$R^2$ is methyl or $C_1$-$C_3$ alkyl, $R^3$ is —H or —$C_1$-$C_3$ alkyl;

$R^4$ is —$C_1$-$C_5$ alkyl;

$R^5$ is H;

$R^6$ is $C_1$-$C_3$ alkyl;

$R^7$ is —$C_1$-$C_5$ alkyl;

$R^8$ is —$C_1$-$C_3$ alkoxy;

$R^9$ is —H or —$C_1$-$C_8$ alkyl;

$R^{24}$ is phenyl;

$R^{25}$ is —$OR^{18}$; wherein $R^{18}$ is —H, a hydroxyl protecting group, or a direct bond where $OR^{18}$ represents =O; and $R^{26}$ is —$C_1$-$C_3$ alkyl;

or a pharmaceutically acceptable salt form thereof.

Auristatins of the formula $D_F$ include those wherein $R^2$ is methyl;

$R^3$, $R^4$, and $R^7$ are independently selected from —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene(monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), —$C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene ($C_6$-$C_{10}$ aryl), heterocycle, —$C_1$-$C_{20}$ alkylene(heterocycle), —$C_2$-$C_{20}$ alkenylene(heterocycle), or —$C_2$-$C_{20}$ alkynylene (heterocycle); wherein said alkyl, alkenyl, alkynyl, alkylene, alkenylene, alkynylene, carbocycle, aryl and heterocycle radicals whether alone or as part of another group are optionally substituted;

$R^5$ is —H;

$R^6$ is methyl;

each $R^8$ is methoxy;

$R^9$ is —H, —$C_1$-$C_{20}$ alkyl, —$C_2$-$C_{20}$ alkenyl, or —$C_2$-$C_{20}$ alkynyl; wherein said alkyl, alkenyl and alkynyl radical are optionally substituted;

$R^{10}$ is optionally substituted aryl or optionally substituted heterocycle;

Z is —O—, —S—, —NH—, or —$NR^{12}$, wherein $R^{12}$ is —$C_1$-$C_{20}$ alkyl, —$C_2$-$C_{20}$ alkenyl, or —$C_2$-$C_{20}$ alkynyl, each of which is optionally substituted;

$R^{11}$ is —H, —$C_1$-$C_{20}$ alkyl, —$C_2$-$C_{20}$ alkenyl, —$C_2$-$C_{20}$ alkynyl, -aryl, -heterocycle, —$(R^{13}O)_m$—$R^{14}$, or —$(R^{13}O)_m$—CH$(R^{15})_2$, wherein said alkyl, alkenyl, alkynyl, aryl and heterocycle radicals are optionally substituted;

m is an integer ranging from 1-1000 or m=0;

$R^{13}$ is —$C_2$-$C_{20}$ alkylene, —$C_2$-$C_{20}$ alkenylene, or —$C_2$-$C_{20}$ alkynylene, each of which is optionally substituted;

$R^{14}$ is —H, —$C_1$-$C_{20}$ alkyl, —$C_2$-$C_{20}$ alkenyl, or —$C_2$-$C_{20}$ alkynyl wherein said alkyl, alkenyl and alkynyl radicals are optionally substituted;

each occurrence of $R^{15}$ is independently —H, —COOH, —$(CH_2)_n$—$N(R^{16})_2$, —$(CH_2)_n$—$SO_3H$, —$(CH_2)_n$—$SO_3$—$C_1$-$C_{20}$ alkyl, —$(CH_2)_n$—$SO_3$—$C_2$-$C_{20}$ alkenyl, or —$(CH_2)_n$—$SO_3$—$C_2$-$C_{20}$ alkynyl wherein said alkyl, alkenyl and alkynyl radicals are optionally substituted;

each occurrence of $R^{16}$ is independently —H, —$C_1$-$C_{20}$ alkyl, —$C_2$-$C_{20}$ alkenyl, —$C_2$-$C_{20}$ alkynyl or —$(CH_2)_n$—COOH wherein said alkyl, alkenyl and alkynyl radicals are optionally substituted;

n is an integer ranging from 0 to 6;

or a pharmaceutically acceptable salt thereof.

In certain of these embodiments, $R^{10}$ is optionally substituted phenyl.

Auristatins of the formula DF include those wherein the groups of $R^2$, $R^3$, $R^4$, $R^5$, $R^6$, $R^7$, $R^8$, and $R^9$ are unsubstituted and the groups of $R^{10}$ and $R^{11}$ are as described herein.

Auristatins of the formula $D_F$ include those wherein said alkyl, alkenyl, alkynyl, alkylene, alkenylene, alkynyklene, aryl, carbocyle, and heterocycle radicals are unsubstituted Auristatins of the formula $D_F$ include those wherein $R^2$ is —$C_1$-$C_3$ alkyl; $R^3$ is —H or —$C_1$-$C_3$ alkyl; $R^4$ is —$C_1$-$C_5$ alkyl; $R^5$ is —H; $R^6$ is —$C_1$-$C_3$ alkyl; $R^7$ is —$C_1$-$C_5$ alkyl; $R^8$ is —$C_1$-$C_3$ alkoxy; $R^9$ is —H or —$C_1$-$C_8$ alkyl; $R^{10}$ is optionally substituted phenyl; Z is —O—, —S—, or —NH—; $R^{11}$ is as defined herein; or a pharmaceutically acceptable salt thereof.

Auristatins of the formula $D_F$ include those wherein $R^2$ is methyl; $R^3$ is —H or —$C_1$-$C_3$ alkyl; $R^4$ is —$C_1$-$C_5$ alkyl; $R^5$ is —H; $R^6$ is methyl; $R^7$ is isopropyl or sec-butyl; $R^8$ is methoxy; $R^9$ is —H or —$C_1$-$C_8$ alkyl; $R^{10}$ is optionally substituted phenyl; Z is —O—, —S—, or —NH—; and $R^{11}$ is as defined herein; or a pharmaceutically acceptable salt thereof.

Auristatins of the formula $D_F$ include those wherein $R^2$ is methyl; $R^3$ is —H or —$C_1$-$C_3$ alkyl; $R^4$ is —$C_1$-$C_5$ alkyl; $R^5$ is —H; $R^6$ is methyl; $R^7$ is isopropyl or sec-butyl; $R^8$ is methoxy; $R^9$ is —H or $C_1$-$C_8$ alkyl; $R^{10}$ is phenyl; and Z is —O— or —NH— and $R^{11}$ is as defined herein, preferably hydrogen; or a pharmaceutically acceptable salt form thereof.

Auristatins of the formula $D_F$ include those wherein $R^2$ is —$C_1$-$C_3$ alkyl; $R^3$ is —H or —$C_1$-$C_3$ alkyl; $R^4$ is —$C_1$-$C_5$ alkyl; $R^5$ is —H; $R^6$ is —$C_1$-$C_3$ alkyl; $R^7$ is —$C_1$-$C_5$ alkyl; $R^8$ is —$C_1$-$C_3$ alkoxy; $R^9$ is —H or —$C_1$-$C_8$ alkyl; $R^{10}$ is phenyl; and Z is —O— or —NH— and $R^{11}$ is as defined herein, preferably hydrogen; or a pharmaceutically acceptable salt form thereof.

Auristatins of the formula $D_E$ or $D_F$ include those wherein $R^3$, $R^4$ and $R^7$ are independently isopropyl or sec-butyl and $R^5$ is —H. In an exemplary embodiment, $R^3$ and $R^4$ are each isopropyl, $R^5$ is H, and $R^7$ is sec-butyl. The remainder of the substituents are as defined herein.

Auristatins of the formula $D_E$ or $D_F$ include those wherein $R^2$ and $R^6$ are each methyl, and $R^9$ is H. The remainder of the substituents are as defined herein.

Auristatins of the formula $D_E$ or $D_F$ include those wherein each occurrence of $R^8$ is —$OCH_3$. The remainder of the substituents are as defined herein.

Auristatins of the formula $D_E$ or $D_F$ include those wherein $R^3$ and $R^4$ are each isopropyl, $R^2$ and $R^6$ are each methyl, $R^5$ is H, $R^7$ is sec-butyl, each occurrence of $R^8$ is —$OCH_3$, and $R^9$ is H. The remainder of the substituents are as defined herein.

Auristatins of the formula $D_F$ include those wherein Z is —O— or —NH—. The remainder of the substituents are as defined herein.

Auristatins of the formula $D_F$ include those wherein $R^{10}$ is aryl. The remainder of the substituents are as defined herein.

Auristatins of the formula $D_F$ include those wherein $R^{10}$ is -phenyl. The remainder of the substituents are as defined herein.

Auristatins of the formula $D_F$ include those wherein Z is —O—, and $R^{11}$ is H, methyl or t-butyl. The remainder of the substituents are as defined herein.

Auristatins of the formula $D_F$ include those wherein, when Z is —NH—, $R^{11}$ is —$(R^{13}O)_m$—$CH(R^{15})_2$, wherein $R^{15}$ is —$(CH_2)_n$—$N(R^{16})_2$, and $R^{16}$ is —$C_1$-$C_8$ alkyl or —$(CH_2)_n$—COOH. The remainder of the substituents are as defined herein.

Auristatins of the formula $D_F$ include those wherein when Z is —NH—, $R^{11}$ is —$(R^{13}O)_m$—$CH(R^{15})_2$, wherein $R^{15}$ is —$(CH_2)_n$—$SO_3H$. The remainder of the substituents are as defined herein.

In preferred embodiments, when D is an auristatin of formula $D_E$, w is an integer ranging from 1 to 12, preferably 2 to 12, y is 1 or 2, and a is preferably 1.

In some embodiments, wherein D is an auristatin of formula $D_F$, a is 1 and w and y are 0.

Illustrative Drug units (-D) include the drug units having the following structures:

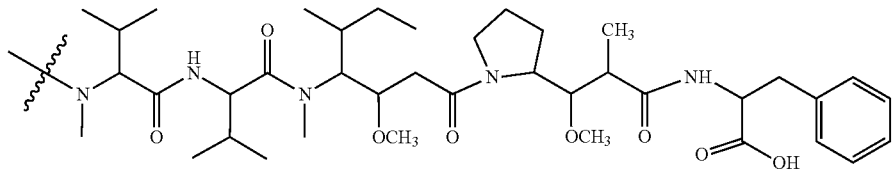

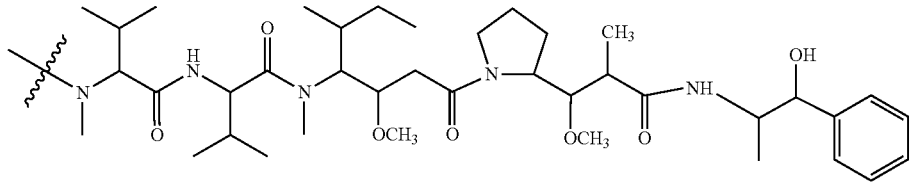

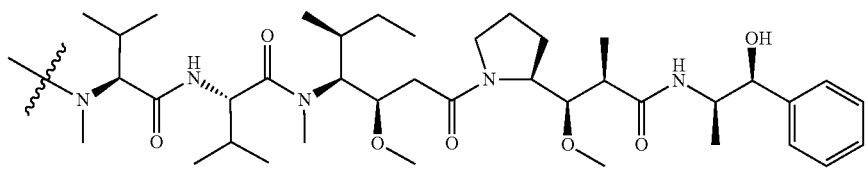

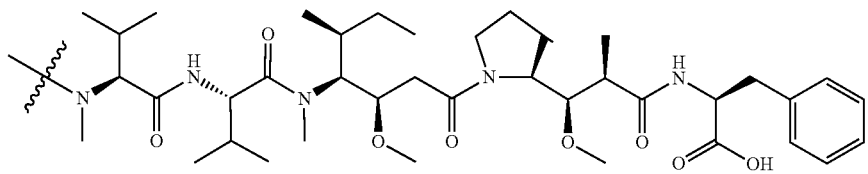

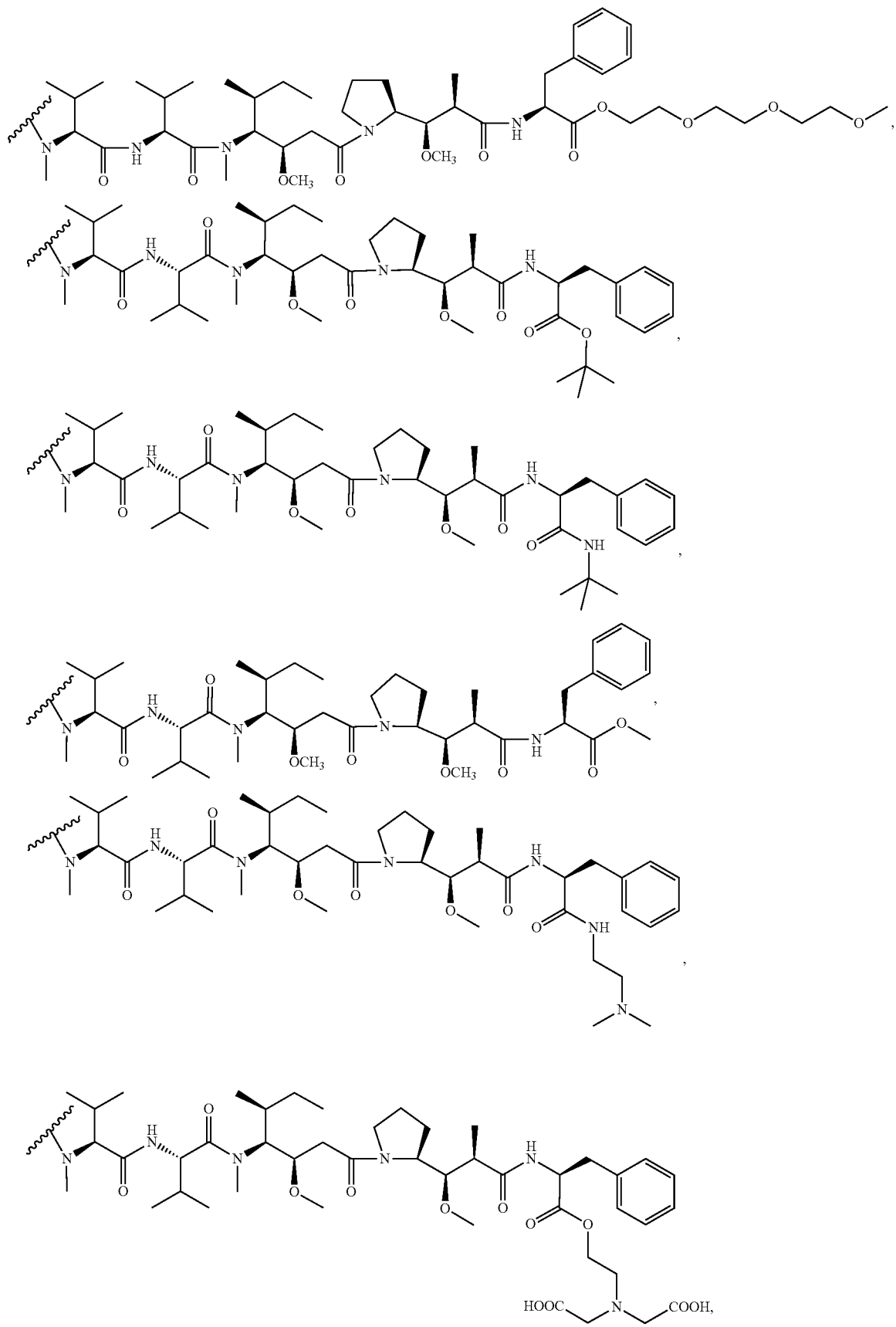

-continued

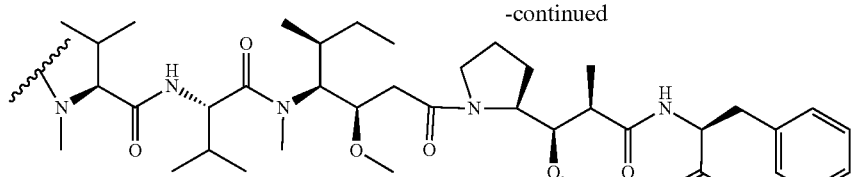

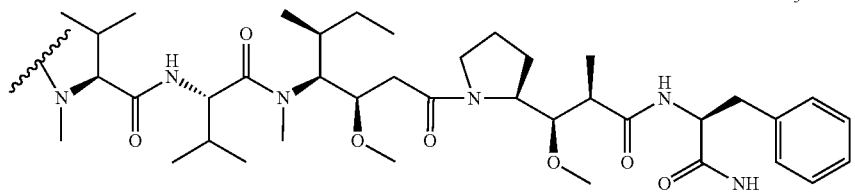

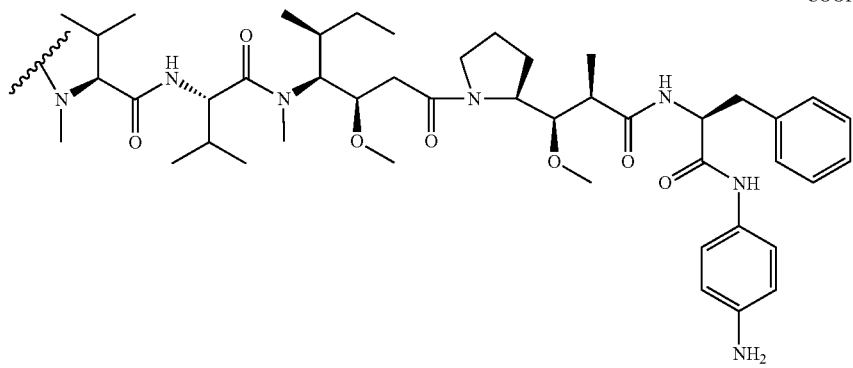

or pharmaceutically acceptable salts or solvates thereof.

In one aspect, hydrophilic groups, such as but not limited to triethylene glycol esters (TEG) can be attached to the Drug Unit at $R^{11}$. Without being bound by theory, the hydrophilic groups assist in the internalization and non-agglomeration of the Drug Unit.

In some embodiments, the Drug unit is not TZT-1027. In some embodiments, the Drug unit is not auristatin E, dolastatin 10, or auristatin PE.

Exemplary antibody-drug conjugate compounds have the following structures wherein "L" or "mAb-s-" represents an 191P4D12 MAb designated Ha22-2(2,4)6.1 set forth herein:

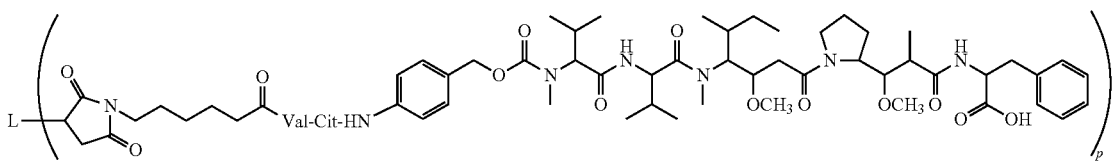

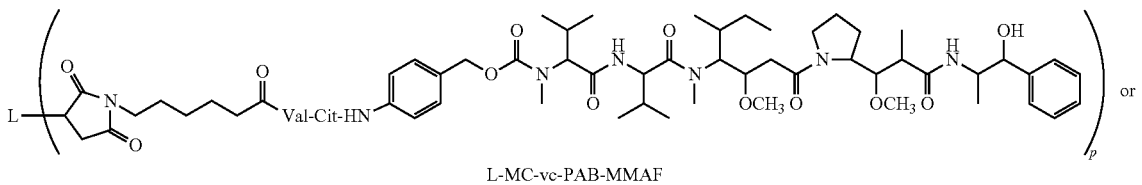

L-MC-vc-PAB-MMAF

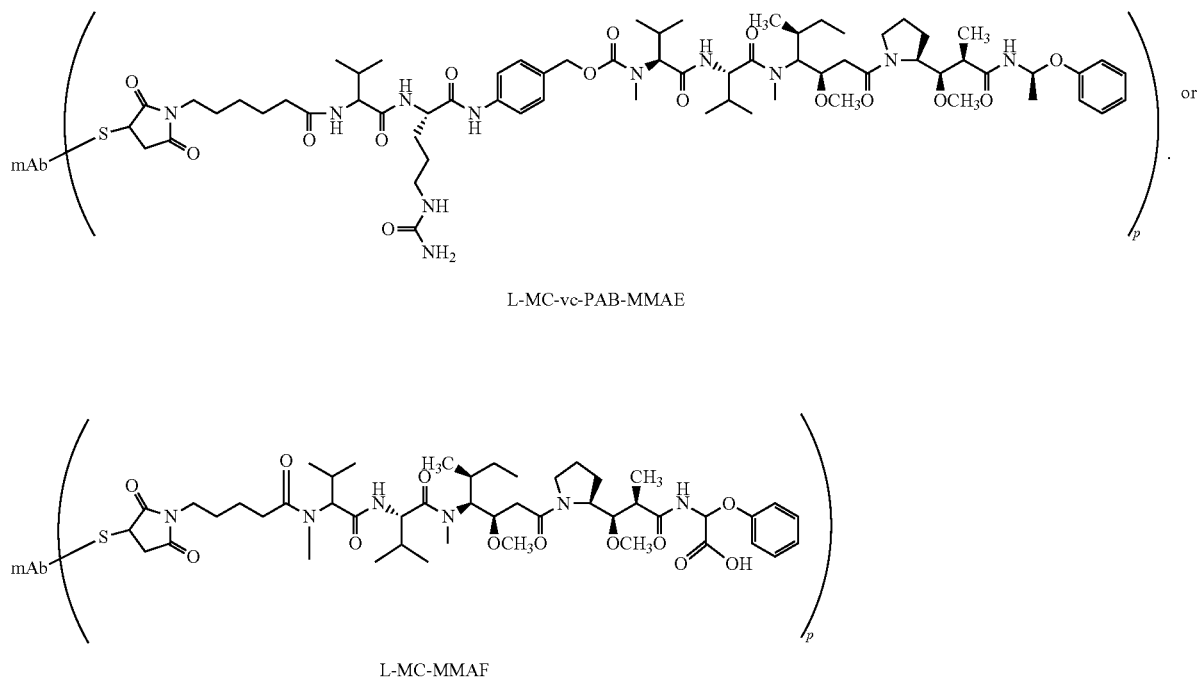

L-MC-vc-PAB-MMAE

L-MC-MMAF or pharmaceutically acceptable salt thereof.

In some embodiments, the Drug Unit is a calicheamicin, camptothecin, a maytansinoid, or an anthracycline. In some embodiments the drug is a taxane, a topoisomerase inhibitor, a vinca alkaloid, or the like.

In some typical embodiments, suitable cytotoxic agents include, for example, DNA minor groove binders (e.g., enediynes and lexitropsins, a CBI compound; see also U.S. Pat. No. 6,130,237), duocarmycins, taxanes (e.g., paclitaxel and docetaxel), puromycins, and vinca alkaloids. Other cytotoxic agents include, for example, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In some embodiments, the Drug is an anti-tubulin agent. Examples of anti-tubulin agents include, auristatins, taxanes (e.g., Taxol® (paclitaxel), Taxotere® (docetaxel)), T67 (Tularik) and vinca alkyloids (e.g., vincristine, vinblastine, vindesine, and vinorelbine). Other antitubulin agents include, for example, baccatin derivatives, taxane analogs (e.g., epothilone A and B), nocodazole, colchicine and colcimid, estramustine, cryptophycins, cemadotin, maytansinoids, combretastatins, discodermolide, and eleutherobin.

In certain embodiments, the cytotoxic agent is a maytansinoid, another group of anti-tubulin agents. For example, in specific embodiments, the maytansinoid is maytansine or DM-1 (ImmunoGen, Inc.; see also Chari et al., 1992, Cancer Res. 52:127-131).

In certain embodiments, the cytotoxic or cytostatic agent is a dolastatin. In certain embodiments, the cytotoxic or cytostatic agent is of the auristatin class. Thus, in a specific embodiment, the cytotoxic or cytostatic agent is MMAE (Formula XI). In another specific embodiment, the cytotoxic or cytostatic agent is AFP (Formula XVI).

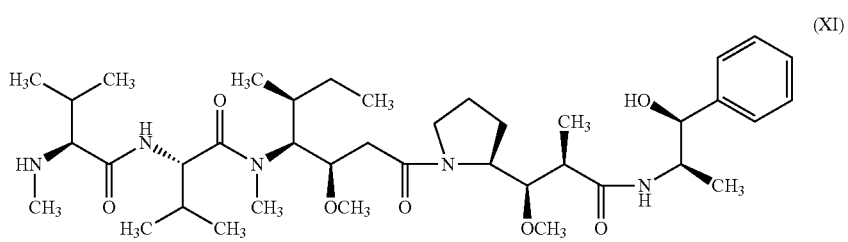 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

(XI)

In certain embodiments, the cytotoxic or cytostatic agent is a compound of formulas XII-XXI or pharmaceutically acceptable salt thereof:
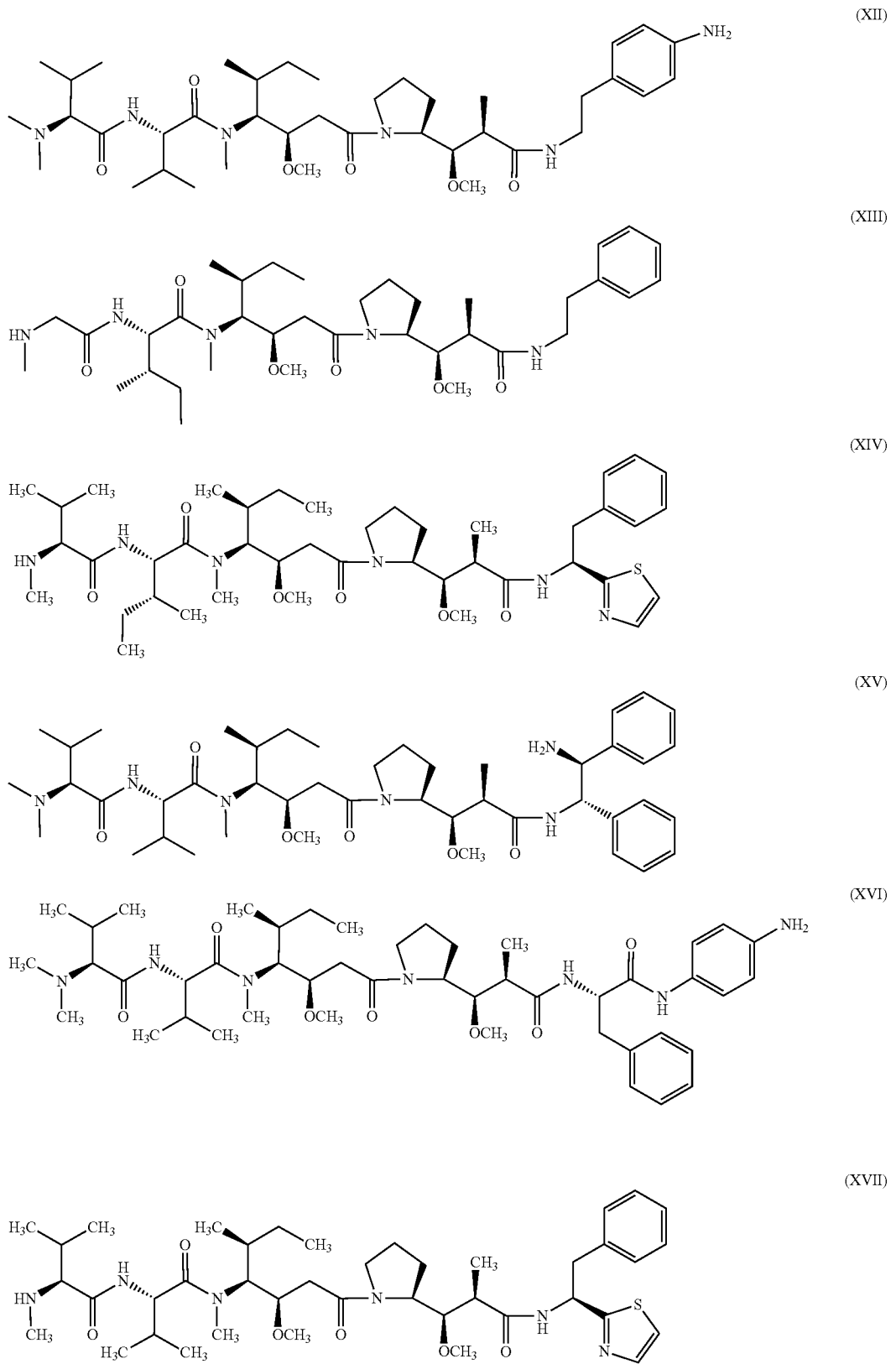
(XII)
(XIII)
(XIV)
(XV)
(XVI)
(XVII)

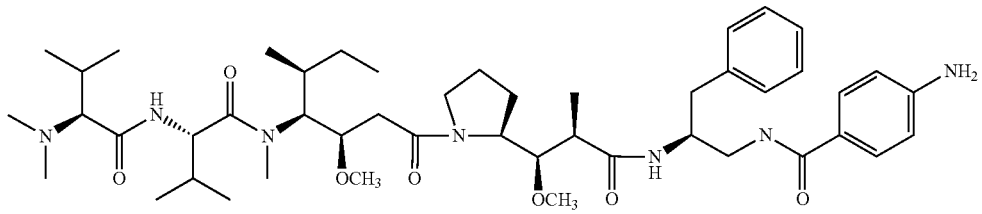
(XVIII)

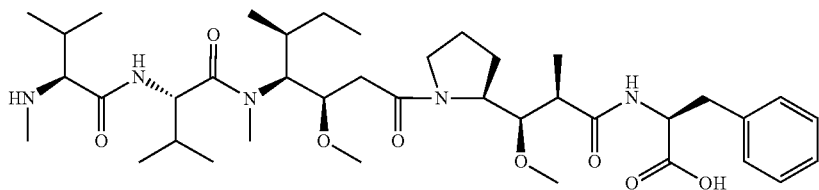
(XVIV)

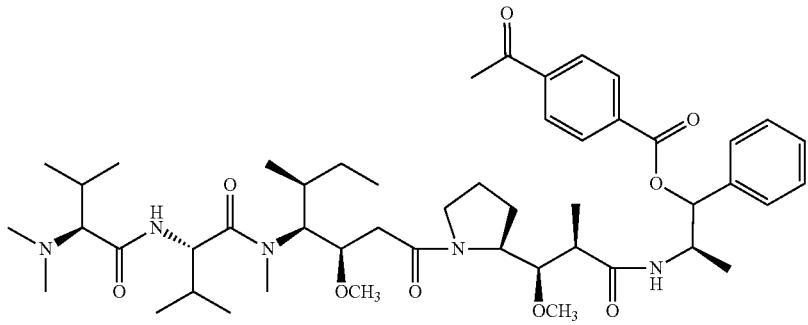
(XX)

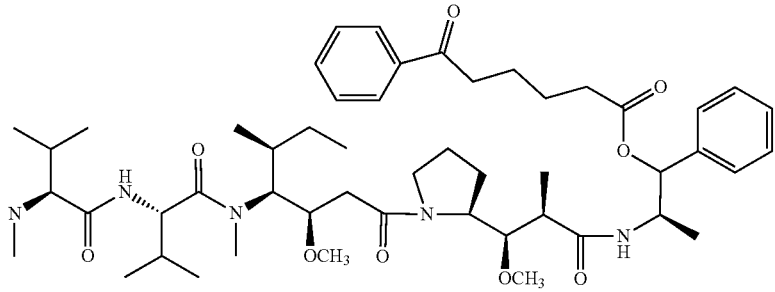
(XXI)

X.) Drug Loading

Drug loading is represented by p and is the average number of Drug moieties per antibody in a molecule. Drug loading may range from 1 to 20 drug moieties (D) per antibody. ADCs of the invention include collections of antibodies conjugated with a range of drug moieties, from 1 to 20. The average number of drug moieties per antibody in preparations of ADC from conjugation reactions may be characterized by conventional means such as mass spectroscopy and, ELISA assay. The quantitative distribution of ADC in terms of p may also be determined. In some instances, separation, purification, and characterization of homogeneous ADC where p is a certain value from ADC with other drug loadings may be achieved by means such as electrophoresis.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the drug loading for an ADC of the invention ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. Indeed, it has been shown that for certain ADCs, the optimal ratio of drug moieties per antibody may be less than 8, and may be about 2 to about 5. See U.S. Pat. No. 7,498,298 (herein incorporated by reference in its entirety).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments (such as thioMab or thioFab prepared as disclosed herein and in WO2006/034488 (herein incorporated by reference in its entirety)).

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

XI.) Methods of Determining Cytotoxic Effect of ADCs

Methods of determining whether a Drug or Antibody-Drug conjugate exerts a cytostatic and/or cytotoxic effect on a cell are known. Generally, the cytotoxic or cytostatic activity of an Antibody Drug conjugate can be measured by: exposing mammalian cells expressing a target protein of the Antibody Drug conjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the Antibody Drug conjugate.

For determining whether an Antibody Drug conjugate exerts a cytostatic effect, a thymidine incorporation assay may be used. For example, cancer cells expressing a target antigen at a density of 5,000 cells/well of a 96-well plated can be cultured for a 72-hour period and exposed to 0.5 µCi of $^3$H-thymidine during the final 8 hours of the 72-hour period. The incorporation of $^3$H-thymidine into cells of the culture is measured in the presence and absence of the Antibody Drug conjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that an Antibody Drug conjugate is useful in the treatment of cancers.

Cell viability can be measured by determining in a cell the uptake of a dye such as neutral red, trypan blue, or ALAMAR™ blue (see, e.g., Page et al., 1993, *Intl. I Oncology* 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytotoxicity (Skehan et al., 1990, *J. Natl. Cancer Inst.* 82:1107-12).

Alternatively, a tetrazolium salt, such as MTT, is used in a quantitative colorimetric assay for mammalian cell survival and proliferation by detecting living, but not dead, cells (see, e.g., Mosmann, 1983, *J. Immunol. Methods* 65:55-63).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in *Biochemica*, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al. eds., 1992, pp. 3.17.1-3.17.16). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza et al., 1995, *Cancer Research* 55:3110-16).

In vivo, the effect of a 191P4D12 therapeutic composition can be evaluated in a suitable animal model. For example, xenogenic cancer models can be used, wherein cancer explants or passaged xenograft tissues are introduced into immune compromised animals, such as nude or SCID mice (Klein et al., 1997, Nature Medicine 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16th Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XII.) Treatment of Cancer(s) Expressing 191P4D12

The identification of 191P4D12 as a protein that is normally expressed in a restricted set of tissues, but which is also expressed in cancers such as those listed in Table I, opens a number of therapeutic approaches to the treatment of such cancers.

Of note, targeted antitumor therapies have been useful even when the targeted protein is expressed on normal tissues, even vital normal organ tissues. A vital organ is one that is necessary to sustain life, such as the heart or colon. A non-vital organ is one that can be removed whereupon the individual is still able to survive. Examples of non-vital organs are ovary, breast, and prostate.

Expression of a target protein in normal tissue, even vital normal tissue, does not defeat the utility of a targeting agent for the protein as a therapeutic for certain tumors in which the protein is also overexpressed. For example, expression in vital organs is not in and of itself detrimental. In addition, organs regarded as dispensable, such as the prostate and ovary, can be removed without affecting mortality. Finally, some vital organs are not affected by normal organ expression because of an immunoprivilege. Immunoprivileged organs are organs that are protected from blood by a blood-organ barrier and thus are not accessible to immunotherapy. Examples of immunoprivileged organs are the brain and testis.

Accordingly, therapeutic approaches that inhibit the activity of a 191P4D12 protein are useful for patients suffering from a cancer that expresses 191P4D12. These therapeutic approaches generally fall into three classes. The first class modulates 191P4D12 function as it relates to tumor cell growth leading to inhibition or retardation of tumor cell growth or inducing its killing. The second class comprises various methods for inhibiting the binding or association of a 191P4D12 protein with its binding partner or with other proteins. The third class comprises a variety of methods for inhibiting the transcription of a 191P4D12 gene or translation of 191P4D12 mRNA.

Accordingly, cancer patients can be evaluated for the presence and level of 191P4D12 expression, preferably using immunohistochemical assessments of tumor tissue, quantitative 191P4D12 imaging, or other techniques that reliably indicate the presence and degree of 191P4D12 expression. Immunohistochemical analysis of tumor biopsies or surgical specimens is preferred for this purpose. Methods for immunohistochemical analysis of tumor tissues are well known in the art.

XIII.) 191P4D12 as a Target for Antibody-Based Therapy

191P4D12 is an attractive target for antibody-based therapeutic strategies. A number of antibody strategies are known in the art for targeting both extracellular and intracellular molecules (see, e.g., complement and ADCC mediated killing as well as the use of intrabodies). Because 191P4D12 is expressed by cancer cells of various lineages relative to corresponding normal cells, systemic administration of 191P4D12-immunoreactive compositions are prepared that exhibit excellent sensitivity without toxic, non-specific and/or non-target effects caused by binding of the immunoreactive composition to non-target organs and tissues. Antibodies specifically reactive with domains of 191P4D12 are useful to treat 191P4D12-expressing cancers systemically, preferably as antibody drug conjugates (i.e. ADCs) wherein the conjugate is with a toxin or therapeutic agent.

Those skilled in the art understand that antibodies can be used to specifically target and bind immunogenic molecules such as an immunogenic region of a 191P4D12 sequence shown in FIG. 1. In addition, skilled artisans understand that it is routine to conjugate antibodies to cytotoxic agents (see, e.g., Slevers et al. Blood 93:11 3678-3684 (Jun. 1, 1999)). When cytotoxic and/or therapeutic agents are delivered directly to cells, such as by conjugating them to antibodies specific for a molecule expressed by that cell (e.g. 191P4D12), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an mammal having a tumor a biologically effective amount of a conjugate comprising a selected cytotoxic and/or therapeutic agent linked to a targeting agent (e.g. a 191P4D12 MAb, preferably Ha22-2(2,4)6.1) that binds to an antigen (e.g. 191P4D12) expressed, accessible to binding or localized on the cell surfaces. A typical embodiment is a method of delivering a cytotoxic and/or therapeutic agent to a cell expressing 191P4D12, comprising conjugating the cytotoxic agent to an antibody that immunospecifically binds to a 191P4D12 epitope, and, exposing the cell to the antibody drug conjugate (ADC). Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using 191P4D12 antibodies can be done in accordance with various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11:117-127). Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp. or Bexxar™, Coulter Pharmaceuticals) respectively, while others involve co-administration of antibodies and other therapeutic agents, such as Herceptin™ (trastuzu MAb) with paclitaxel (Genentech, Inc.). In a preferred embodiment, the antibodies will be conjugated a cytotoxic agent, supra, preferably an aurastatin derivative designated MMAE (Seattle Genetics, Inc).

Although 191P4D12 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan et al. (Cancer Res. 53:4637-4642, 1993), Prewett et al. (International J. of Onco. 9:217-224, 1996), and Hancock et al. (Cancer Res. 51:4575-4580, 1991) describe the use of various antibodies together with chemotherapeutic agents.

191P4D12 monoclonal antibodies that treat the cancers set forth in Table I include those that initiate a potent immune response against the tumor or those that are directly cytotoxic. In this regard, 191P4D12 monoclonal antibodies (MAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, 191P4D12 MAbs that exert a direct biological effect on tumor growth are useful to treat cancers that express 191P4D12. Mechanisms by which directly cytotoxic MAbs act include: inhibition of cell growth, modulation of cellular differentiation, modulation of tumor angiogenesis factor profiles, and the induction of apoptosis. The mechanism(s) by which a particular 191P4D12 MAb exerts an anti-tumor effect is evaluated using any number of in vitro assays that evaluate cell death such as ADCC, complement-mediated cell lysis, and so forth, as is generally known in the art.

Accordingly, preferred monoclonal antibodies used in the therapeutic methods of the invention are those that are either fully human and that bind specifically to the target 191P4D12 antigen with high affinity.

XIV.) 191P4D12 ADC Cocktails

Therapeutic methods of the invention contemplate the administration of single 191P4D12 ADCs as well as combinations, or cocktails, of different MAbs (i.e. 191P4D12 MAbs or Mabs that bind another protein). Such MAb cocktails can have certain advantages inasmuch as they contain MAbs that target different epitopes, exploit different effector mechanisms or combine directly cytotoxic MAbs with MAbs that rely on immune effector functionality. Such MAbs in combination can exhibit synergistic therapeutic effects. In addition, 191P4D12 MAbs can be administered concomitantly with other therapeutic modalities, including but not limited to various chemotherapeutic and biologic agents, androgen-blockers, immune modulators (e.g., IL-2, GM-CSF), surgery or radiation. In a preferred embodiment, the 191P4D12 MAbs are administered in conjugated form.

191P4D12 ADC formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the 191P4D12 ADC preparation, via an acceptable route of administration such as intravenous injection (IV), typically at a dose in the range, including but not limited to, 0.1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10-1000 mg MAb per week are effective and well tolerated.

Based on clinical experience with the Herceptin® (Trastuzumab) in the treatment of metastatic breast cancer, an initial loading dose of approximately 4 mg/kg patient body weight IV, followed by weekly doses of about 2 mg/kg IV of the MAb preparation represents an acceptable dosing regimen. Preferably, the initial loading dose is administered as a 90-minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the MAbs used, the degree of 191P4D12 expression in the patient, the extent of circulating shed 191P4D12 antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 191P4D12 in a given sample (e.g. the levels of circulating 191P4D12 antigen and/or 191P4D12 expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

An object of the present invention is to provide 191P4D12 ADCs, which inhibit or retard the growth of tumor cells expressing 191P4D12. A further object of this invention is to provide methods to inhibit angiogenesis and other biological functions and thereby reduce tumor growth in mammals, preferably humans, using such 191P4D12 ADCs, and in particular using such 191P4D12 ADCs combined with other drugs or immunologically active treatments.

XV.) Combination Therapy

In one embodiment, there is synergy when tumors, including human tumors, are treated with 191P4D12 ADCs in conjunction with chemotherapeutic agents or radiation or combinations thereof. In other words, the inhibition of tumor growth by a 191P4D12 ADC is enhanced more than expected when combined with chemotherapeutic agents or radiation or combinations thereof. Synergy may be shown, for example, by greater inhibition of tumor growth with combined treatment than would be expected from a treatment of only 191P4D12 ADC or the additive effect of treatment with a 191P4D12 ADC and a chemotherapeutic agent or radiation. Preferably, synergy is demonstrated by remission of the cancer where remission is not expected from treatment either from a 191P4D12 ADC or with treatment using an additive combination of a 191P4D12 ADC and a chemotherapeutic agent or radiation.

The method for inhibiting growth of tumor cells using a 191P4D12 ADC and a combination of chemotherapy or radiation or both comprises administering the 191P4D12 ADC before, during, or after commencing chemotherapy or radiation therapy, as well as any combination thereof (i.e. before and during, before and after, during and after, or before, during, and after commencing the chemotherapy and/or radiation therapy). For example, the 191P4D12 ADC is typically administered between 1 and 60 days, preferably between 3 and 40 days, more preferably between 5 and 12 days before commencing radiation therapy and/or chemotherapy. However, depending on the treatment protocol and the specific patient needs, the method is performed in a manner that will provide the most efficacious treatment and ultimately prolong the life of the patient.

The administration of chemotherapeutic agents can be accomplished in a variety of ways including systemically by the parenteral and enteral routes. In one embodiment, the 191P4D12 ADCs and the chemotherapeutic agent are administered as separate molecules. Particular examples of chemotherapeutic agents or chemotherapy include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, gemcitabine, chlorambucil, taxol and combinations thereof.

The source of radiation, used in combination with a 191P4D12 ADC, can be either external or internal to the patient being treated. When the source is external to the patient, the therapy is known as external beam radiation therapy (EBRT). When the source of radiation is internal to the patient, the treatment is called brachytherapy (BT).

The above described therapeutic regimens may be further combined with additional cancer treating agents and/or regimes, for example additional chemotherapy, cancer vaccines, signal transduction inhibitors, agents useful in treating abnormal cell growth or cancer, antibodies (e.g. Anti-CTLA-4 antibodies as described in WO/2005/092380 (Pfizer)) or other ligands that inhibit tumor growth by binding to IGF-1R, and cytokines.

When the mammal is subjected to additional chemotherapy, chemotherapeutic agents described above may be used. Additionally, growth factor inhibitors, biological response modifiers, anti-hormonal therapy, selective estrogen receptor modulators (SERMs), angiogenesis inhibitors, and anti-androgens may be used. For example, anti-hormones, for example anti-estrogens such as Nolvadex (tamoxifen) or, anti-androgens such as Casodex (4'-cyano-3-(4-fluorophenylsulphonyl)-2-hydroxy-2-methyl-3-'-(trifluoromethyl)propionanilide) may be used.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

XVI.) Kits/Articles of Manufacture

For use in the laboratory, prognostic, prophylactic, diagnostic and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise an antibody that is or can be detectably labeled. Kits can comprise a container comprising a Drug Unit. The kit can include all or part of the amino acid sequences in FIG. 2, or FIG. 3 or analogs thereof, or a nucleic acid molecule that encodes such amino acid sequences.

The kit of the invention will typically comprise the container described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label a can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a cancer of a tissue set forth in Table I.

The terms "kit" and "article of manufacture" can be used as synonyms.

In another embodiment of the invention, an article(s) of manufacture containing compositions, such as antibody(s), or antibody drug conjugates (ADCs) e.g., materials useful for the diagnosis, prognosis, prophylaxis and/or treatment of cancers of tissues such as those set forth in Table I is provided. The article of manufacture typically comprises at least one container and at least one label. Suitable containers include, for example, bottles, vials, syringes, and test tubes. The containers can be formed from a variety of materials such as glass, metal or plastic. The container can hold amino acid sequence(s), small molecule(s), nucleic acid sequence(s), cell population(s) and/or antibody(s). In another embodiment a container comprises an antibody, binding fragment thereof or specific binding protein for use in evaluating protein expression of 191P4D12 in cells and tissues, or for relevant laboratory, prognostic, diagnostic, prophylactic and therapeutic purposes; indications and/or directions for such uses can be included on or with such container, as can reagents and other compositions or tools used for these purposes.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be an antibody capable of specifically binding 191P4D12 or an antibody drug conjugate specifically binding to 191P4D12.

The article of manufacture can further comprise a second container comprising a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

EXAMPLES

Various aspects of the invention are further described and illustrated by way of the several examples that follow, none of which is intended to limit the scope of the invention.

Example 1

The 191P4D12 Antigen

The 191P4D12 gene sequence was discovered using Suppression Subtractive Hybridization (SSH) methods known in the art. The 191P4D12 SSH sequence of 223 bp was identified from a bladder tumor minus cDNAs derived from a pool of nine (9) normal tissues using standard methods. A full length cDNA clone for 191P4D12 was isolated from a bladder cancer cDNA library. The cDNA is 3464 bp in length and encodes a 510 amino acid ORF (See, FIG. 1). The 191P4D12 gene shows homology to Nectin-4 gene. For further reference see, US2004/0083497 (Agensys, Inc., Santa Monica, Calif.) and PCT Publication WO2004/016799 (Agensys, Inc., Santa Monica, Calif.). For exemplary embodiments of the 191P4D12 antigen, see FIG. 1.

Example 2

Generation of 191P4D12 Monoclonal Antibodies (MAbs)

In one embodiment, therapeutic Monoclonal Antibodies ("MAbs") to 191P4D12 and 191P4D12 variants comprise those that react with epitopes specific for each protein or specific to sequences in common between the variants that would bind, internalize, disrupt or modulate the biological function of 191P4D12 or 191P4D12 variants, for example, those that would disrupt the interaction with ligands, substrates, and binding partners. Immunogens for generation of such MAbs include those designed to encode or contain the extracellular domains or the entire 191P4D12 protein sequence, regions predicted to contain functional motifs, and regions of the 191P4D12 protein variants predicted to be antigenic from computer analysis of the amino acid sequence. Immunogens include peptides and recombinant proteins such as tag5-191P4D12, a purified mammalian cell derived His tagged protein. In addition, cells engineered to express high levels of 191P4D12, such as RAT1-191P4D12 or 300.19-191P4D12, are used to immunize mice.

MAbs to 191P4D12 were generated using XenoMouse Technology® (Amgem Fremont) wherein the murine heavy and kappa light chain loci have been inactivated and a majority of the human heavy and kappa light chain immunoglobulin loci have been inserted. The MAb designated Ha22-2(2,4)6.1 was generated from immunization of human γ1 producing XenoMice with pTag5/mychis-191P4D12 (amino acids 23-351).

The 191P4D12 MAb Ha22-2(2,4)6.1 specifically binds to pTag5/mychis-191P4D12 protein by ELISA as well as recombinant 191P4D12 expressing cells and multiple cancer cell lines expressing 191P4D12.

The hybridoma producing an antibody designated Ha22-2(2,4)6.1 was sent (via Federal Express) to the American Type Culture Collection (ATCC), P.O. Box 1549, Manassas, Va. 20108 on 18 Aug. 2010 and assigned Accession number PTA-11267.

DNA coding sequences for 191P4D12 MAb Ha22-2(2,4) 6.1 was determined after isolating mRNA from the respective hybridoma cells with Trizol reagent (Life Technologies, Gibco BRL).

Anti-191P4D12 Ha22-2(2,4)6.1 heavy and light chain variable nucleic acid sequences were sequenced from the hybridoma cells using the following protocol. Ha22-2(2,4) 6.1 secreting hybridoma cells were lysed with Trizol reagent (Life Technologies, Gibco BRL). Total RNA was purified and quantified. First strand cDNAs was generated from total RNA with oligo (dT)12-18 priming using the Gibco-BRL Superscript Preamplification system. First strand cDNA was amplified using human immunoglobulin variable heavy chain primers, and human immunoglobulin variable light chain primers. PCR products were sequenced and the variable heavy and light chain regions determined.

The nucleic acid and amino acid sequences of the variable heavy and light chain regions are listed in FIG. 2 and FIG. 3. Alignment of Ha22-2(2,4)6.1 MAb to human Ig germline is set forth in FIG. 4A-4B.

Example 3

Expression of Ha22-2(2,4)6.1 Using Recombinant DNA Methods

To express Ha22-2(2,4)6.1 MAb recombinantly in transfected cells, Ha22-2(2,4)6.1 MAb variable heavy and light chain sequences were cloned upstream of the human heavy chain IgG1 and human light chain Igκ constant regions respectively. The complete Ha22-2(2,4)6.1 MAb human heavy chain and light chain cassettes were cloned downstream of the CMV promoter/enhancer in a cloning vector. A polyadenylation site was included downstream of the MAb coding sequence. The recombinant Ha22-2(2,4)6.1 MAb expressing constructs were transfected into CHO cells. The Ha22-2(2,4)6.1 MAb secreted from recombinant cells was evaluated for binding to cell surface 191P4D12 by flow cytometry (FIG. 5A). RAT-control and RAT-191P4D12 cells were stained with Ha22-2(2,4)6.1 MAb from either hybridoma or from CHO cells transfected with Ha22-2(2, 4)6.1 heavy and light chain vector constructs. Binding was detected by flow cytometry.

Results show that the recombinantly expressed Ha22-2 (2,4)6.1 expressed in CHO cells binds 191P4D12 similarly to the Ha22-2(2,4)6.1 purified from hybridoma. The Ha22-2(2,4)6.1 MAb secreted from recombinant cells was also evaluated for binding to 191P4D12 recombinant protein by ELISA. As shown in FIG. 5B, binding of Ha22-2(2,4)6.1 to 191P4D12 protein was identical between MAb material derived from CHO and from hybridoma cells.

Example 4

Antibody Drug Conjugation of Ha22-2(2,4)6.1 MAb

The Ha22-2(2,4)6.1 Mab (FIG. 2) was conjugated to an auristatin derivative designated MMAE (Formula XI) using a vc (Val-Cit) linker described herein to create the antibody drug conjugate (ADC) of the invention designated Ha22-2(2,4)6.1vcMMAE using the following protocols. The conjugation of the vc (Val-Cit) linker to the MMAE (Seattle Genetics, Inc., Seattle, Wash.) was completed using the general method set forth in Table IV to create the cytotoxic vcMMAE (see, U.S. Pat. No. 7,659,241).

Next, the antibody drug conjugate (ADC) of the invention designated Ha22-2(2,4)6.1vcMMAE was made using the following protocols.

Briefly, a 15 mg/mL solution of the Ha22-2(2,4)6.1MAb in 10 mM acetate at pH 5.0, 1% sorbitol, 3% L-agrinine is added with a 20% volume of 0.1 M TrisCl at pH 8.4, 25 mM EDTA and 750 mM NaCl to adjust the pH of the solution to 7.5, 5 mM EDTA and 150 mM sodium chloride. The MAb is then partially reduced by adding 2.3 molar equivalents of TCEP (relative to moles of MAb) and then stirred at 37° C. for 2 hours. The partially reduced MAb solution is then cooled to 5° C. and 4.4 molar equivalents of vcMMAE (relative to moles of antibody) are added as a 6% (v/v) solution of DMSO. The mixture is stirred for 60 minutes at 5° C., then for 15 additional minutes following the addition of 1 molar equivalents of N-acetylcysteine relative to vcMMAE. Excess quenched vcMMAE and other reaction components are removed by ultrafiltration/diafiltration of the antibody drug conjugate (ADC) with 10 volumes of 20 mM histidine, pH 6.0.

The resulting antibody drug conjugate (ADC) is designated Ha22-2(2,4)6.1vcMMAE and has the following formula:

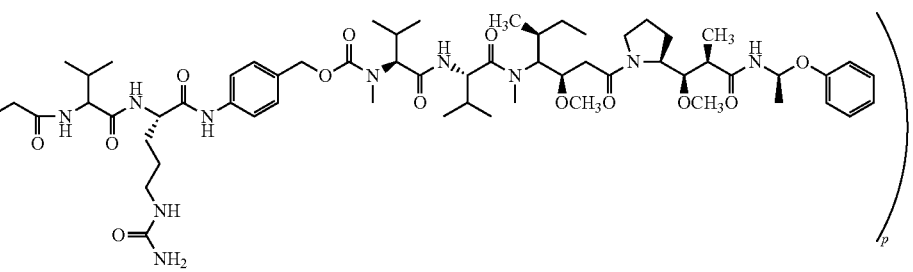

wherein MAb is Ha22-2(2,4)6.1 (FIG. 2 and FIG. 3) and p is from 1 to 8. The p value of the antibody drug conjugate set forth in this Example was about 3.8.

Example 5

Characterization of Ha22-2(2,4)6.1vcMMAE

Antibody Drug Conjugates that bind 191P4D12 were generated using the procedures set forth in the example entitled "Antibody Drug Conjugation of Ha22-2(2,4)6.1 MAb" and were screened, identified, and characterized using a combination of assays known in the art.

A. Affinity Determination by FACS

Ha22-2(2,4)6.1vcMMAE was tested for its binding affinity to 191P4D12 expressed on the surface of PC3-human-191P4D12, PC3-Cynomolgus-191P4D12, and PC3-rat-191P4D12 cells respectively. Briefly, eleven (11) dilutions of Ha22-2(2,4)6.1vcMMAE were incubated with each of the cell types (50,000 cells per well) overnight at 4° C. at a final concentration of 160 nM to 0.011 nM. At the end of the incubation, cells are washed and incubated with anti-hIgG-PE detection antibody for 45 min at 4° C. After washing the unbound detection antibodies, the cells are analyzed by FACS. Mean Florescence Intensity (MFI) values were obtained as listed in FIGS. 6-8. MFI values were entered into Graphpad Prisim software and analyzed using the one site binding (hyperbola) equation of Y=Bmax*X/(Kd+X) to generate Ha22-2(2,4)6.1vcMMAE saturation curves shown also in FIGS. 6-8 respectively. Bmax is the MFI value at maximal binding of Ha22-2(2,4)6.1vcMMAE to 191P4D12; Kd is the Ha22-2(2,4)6.1vcMMAE binding affinity which is the concentration of Ha22-2(2,4)6.1vcMMAE required to reach half-maximal binding.

The calculated affinity (Kd) of Ha22-2(2,4)6.1vcMMAE to 191P4D12 expressed on the surface of PC3-human-191P4D12, PC3-Cynomolgus-191P4D12, and PC3-rat-191P4D12 cells respectively is 0.69 nM (FIG. 6), 0.34 nM (FIG. 7), and 1.6 nM (FIG. 8).

B. Affinity Determination by SPR

The affinity of Ha22-2(2,4)6.1 MAb and Ha22-2(2,4)6.1vcMMAE to purified recombinant 191P4D12 (ECD amino acids 1-348) was performed by Surface Plasmon Resonance (SPR) (BIAcore). Briefly, goat-anti-human Fcγ polyclonal Abs (Jackson Immuno Research Labs, Inc.) were covalently immobilized on the surface of a CM5 sensor chip (Biacore). Purified Ha22-2(2,4)6.1 MAb or Ha22-2(2,4)6.1vcMMAE were then captured on the surface of said chip. On average, approximately 300 RUs of test Ha22-2(2,4)6.1 MAb or Ha22-2(2,4)6.1vcMMAE was captured in every cycle. Subsequently, a series of five (5) to six (6) dilutions of recombinant 191P4D12 (ECD amino acids 1-348) ranging from 1 nM to 100 nM was injected over such surface to generate binding curves (sensograms) that were processed and globally fit to a 1:1 interaction model using BIAevaluation 3.2 and CLAMP software (Myszka and Morton, 1998) (FIG. 22). Table V summarizes association and dissociation rate constants as well as affinities of Ha22-2(2,4)6.1 MAb and Ha22-2(2,4)6.1vcMMAE to recombinant 191P4D12 (ECD amino acids 1-348).

C. Domain Mapping of Ha22-2(2,4)6.1 MAb

To map the binding site of Ha22-2(2,4)6.1 MAb to a specific domain of 191P4D12 protein, several Rat1(E) recombinant cell lines expressing such domains (or a combination thereof) were generated (Table VI). Binding of Ha22-2(2,4)6.1 to cell surface was assessed by FACS using standard protocols. As shown in FIG. 10, Ha22-2(2,4)6.1 MAb binds to VC1 domain expressing cells as well as wild-type 191P4D12, but not to C1C2 domain expressing cells. Additionally, another 191P4D12 MAb entitled Ha22-8e6.1 recognizes C1C2 domain of 191P4D12 on cell surface, but not the VC1 domain. This suggests that the binding site for Ha22-2(2,4)6.1 MAb is located in the 1-147 aa domain of 191P4D12, but that not every MAb which binds to 191P4D12 recognizes this domain.

To further corroborate the results set forth in FIG. 10, a Western Blot analysis was performed. Briefly, the entire extracellular portion of 191P4D12 (full length), as well as specific domains set forth in Table VI were expressed in 293T cells as murine Fc fusion proteins and purified. Goat anti-mouse-HRP were used as a control. As shown in FIG. 11, when resolved on SDS-PAGE (non-reduced) and probed with Ha22-2(2,4)6.1-biotin followed by streptavidin-HRP, bands corresponding to full-length 191P4D12 (lane 1), V (lane 2) and VC1 (lane 3) fusion constructs, but not C1C2 fusion construct (lane 4) are recognized. This further suggests that the binding epitope for Ha22-2(2,4)6.1 MAb is located within 1-147 aa domain of 191P4D12.

Example 6

Cell Cytotoxicity Mediated by Ha22-2(2,4)6.1vcMMAE

The ability of Ha22-2(2,4)6.1vcMMAE to mediate 191P4D12-dependent cytotoxicity was evaluated in PC3 cells engineered to express human 191P4D12, Cynomolgus 191P4D12 and rat 191P4D12. Briefly, PC3-Neo, PC3-human-191P4D12 cells, PC3-Cynomolgus-191P4D12 or PC3-rat-191P4D12 cells (1500 cells/well) were seeded into a 96 well plate on day 1. The following day an equal volume of medium containing the indicated concentration of Ha22-2 (2,4)6.1vcMMAE or a Control MAb conjugated with vcMMAE (i.e. Control-vcMMAE) was added to each well. The cells were allowed to incubate for 4 days at 37 degrees C. At the end of the incubation period, Alamar Blue was added to each well and incubation continued for an additional 4 hours. The resulting fluorescence was detected using a Biotek plate reader with an excitation wavelength of 620 nM and an emission wavelength of 540 nM.

Figure 9D:
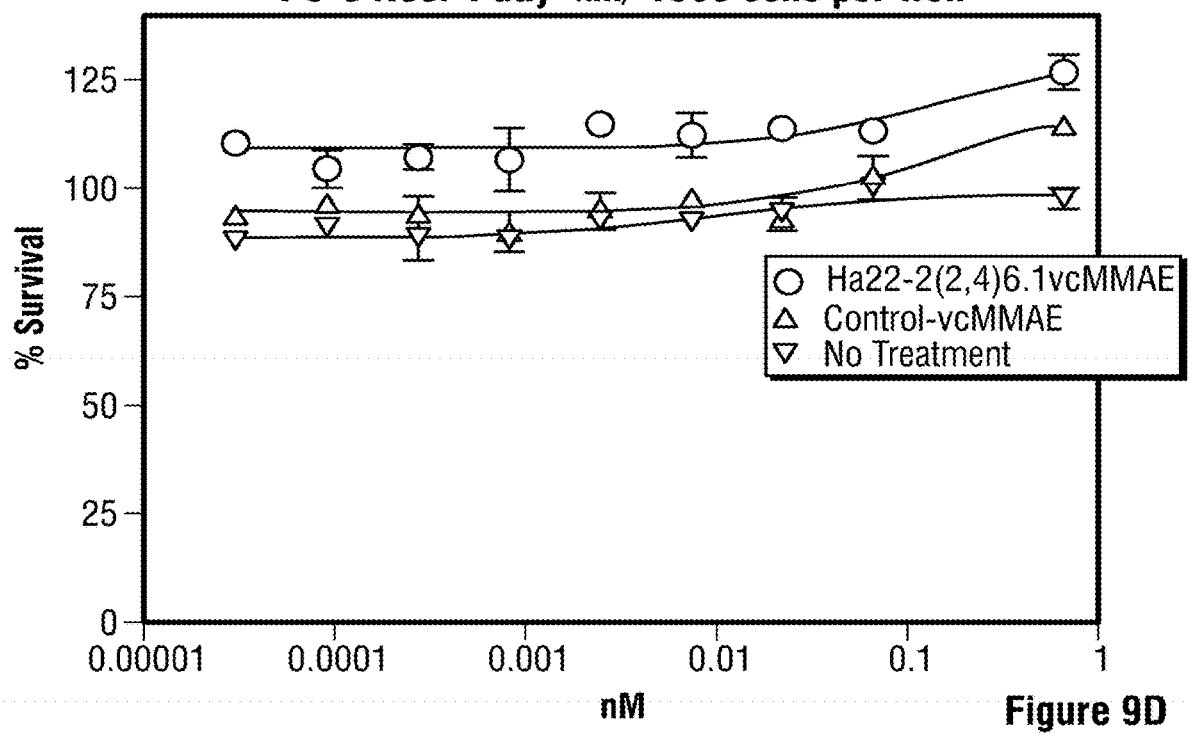
FIG. 9D: Cell cytotoxicity assay using PC3-Neo cells.
Figure 21A:
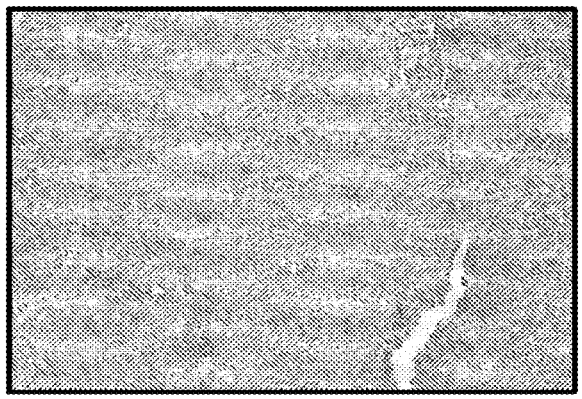
FIGS. 21A-B show bladder cancer specimens.
Figure 21B:
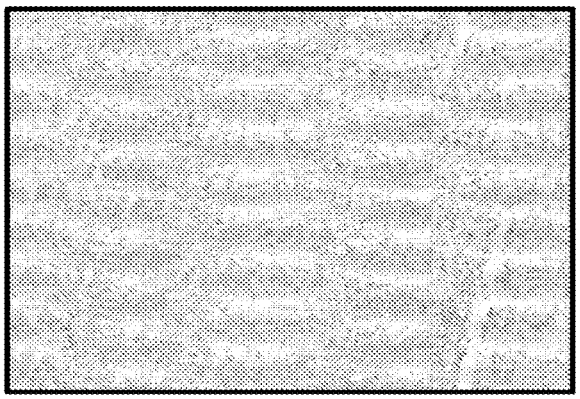
Figure 21C:
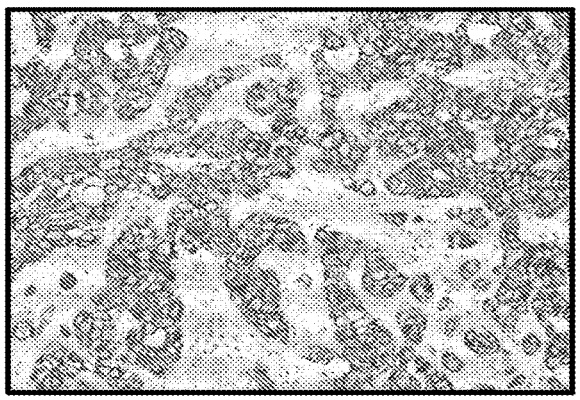
FIGS. 21C-D show breast cancer specimens.
Figure 21D:
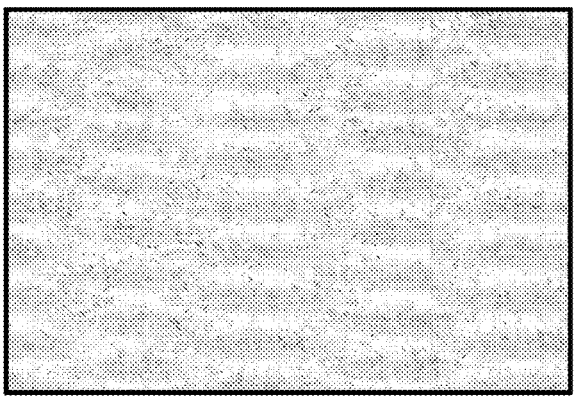
Figure 21E:
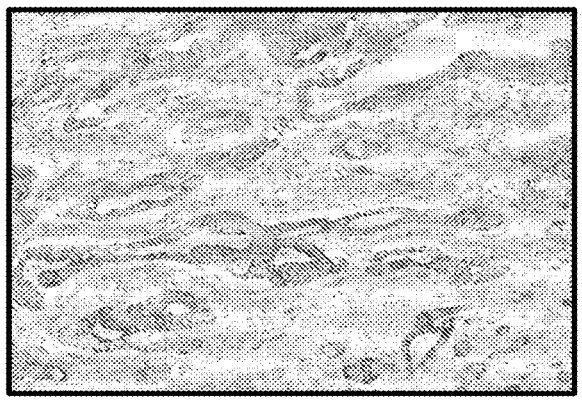
FIGS. 21E-F show pancreatic cancer specimens.
Figure 21F:
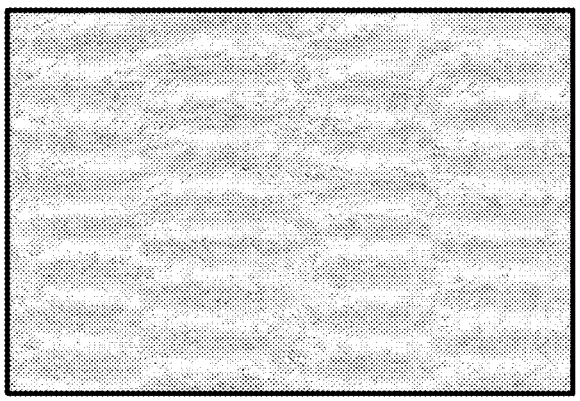
Figure 21G:
FIGS. 21G-H show lung cancer specimens.
Figure 21H:
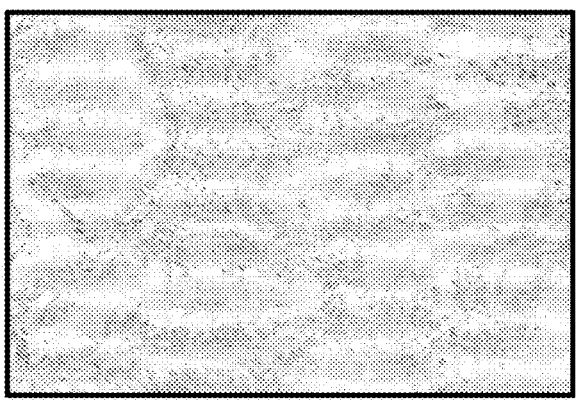
Figure 21I:
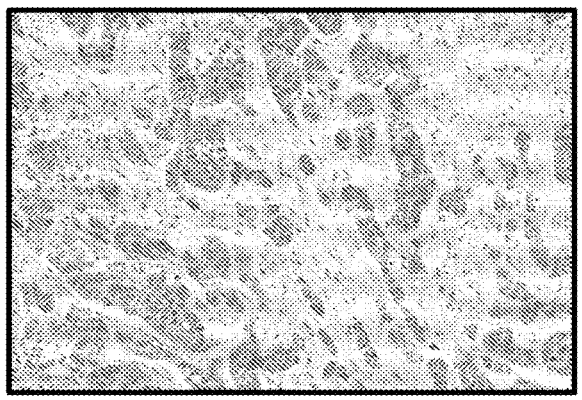
FIGS. 21I-J show ovarian cancer specimens.
Figure 21J:
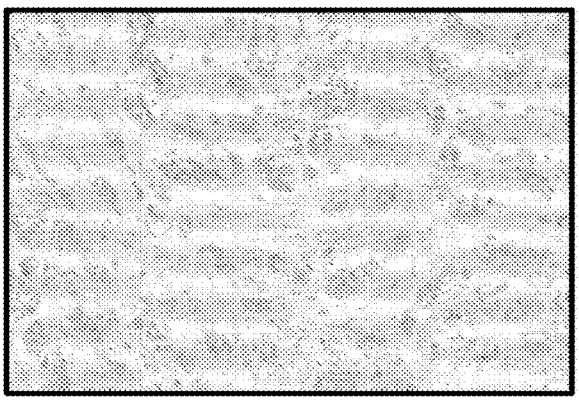
Figure 21K:
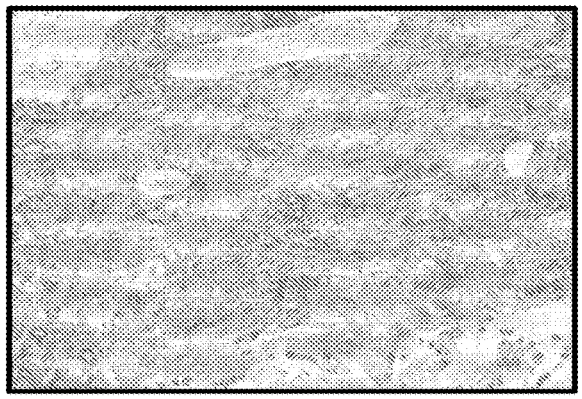
FIGS. 21K-L show esophageal cancer specimens.
Figure 21L:
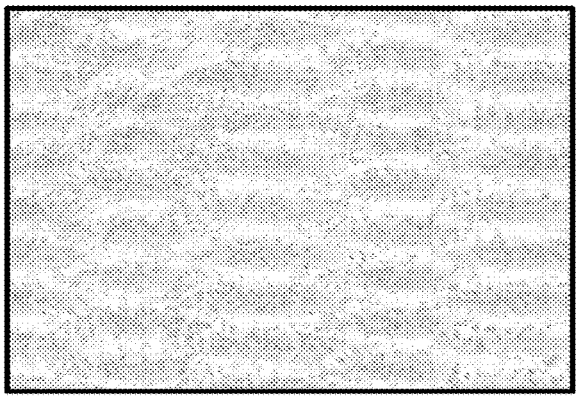
Figure 21M:
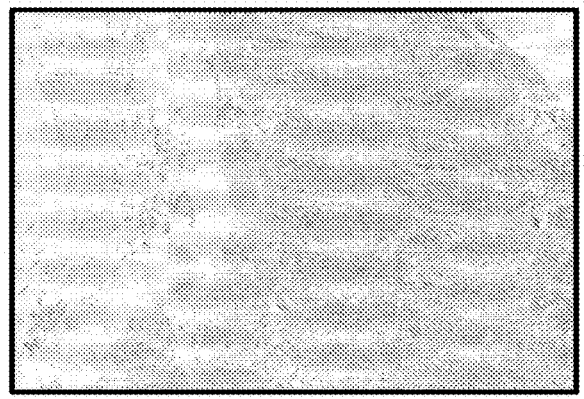
FIG. 21M-N show esophageal cancer specimens.
Figure 21N:
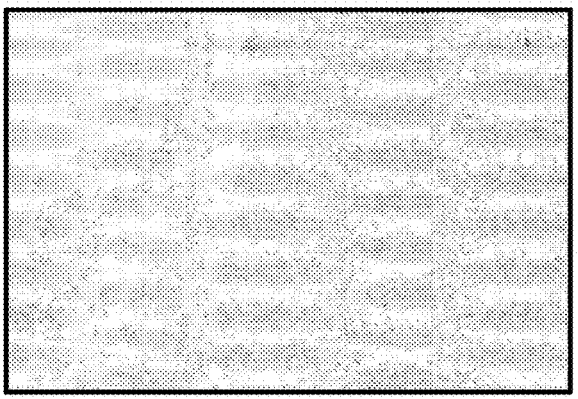

The results in FIG. 9A-9D show that Ha22-2(2,4)6.1vcMMAE mediated cytotoxicity in PC3-human-191P4D12 (FIG. 9A), PC3-Cynomolgus-191P4D12 (FIG. 9B), and PC3-rat-191P4D12 cells (FIG. 9C) while a control human IgG conjugated with vcMMAE had no effect. The specificity of Ha22-2(2,4)6.1vcMMAE was further demonstrated by the lack of toxicity for PC3-Neo cells that do not express 191P4D12 (FIG. 9D). Thus, these results indicate that Ha22-2(2,4)6.1vcMMAE can selectively deliver a cytotoxic drug to 191P4D12 expressing cells leading to their killing.

Example 7

Ha22-2(2,4)6.1vcMMAE Inhibit Growth of Tumors In Vivo

The significant expression of 191P4D12 on the cell surface of tumor tissues, together with its restrictive expression in normal tissues makes 191P4D12 a good target for antibody therapy and similarly, therapy via ADC. Thus, the therapeutic efficacy of Ha22-2(2,4)6.1vcMMAE in human bladder, lung, breast, and pancreatic cancer xenograft mouse models is evaluated.

Antibody drug conjugate efficacy on tumor growth and metastasis formation is studied in mouse cancer xenograft models (e.g. subcutaneous and orthotopically).

Subcutaneous (s.c.) tumors are generated by injection of $5 \times 10^4$-$10^6$ cancer cells mixed at a 1:1 dilution with Matrigel (Collaborative Research) in the right flank of male SCID mice. To test ADC efficacy on tumor formation, ADC injections are started on the same day as tumor-cell injections. As a control, mice are injected with either purified human IgG or PBS; or a purified MAb that recognizes an irrelevant antigen not expressed in human cells. In preliminary studies, no difference is found between control IgG or PBS on tumor growth. Tumor sizes are determined by caliper measurements, and the tumor volume is calculated as $width^2 \times Length/2$, wherein width is the smallest dimension and length is the largest dimension. Mice with subcutaneous tumors greater than 1.5 cm in diameter are sacrificed.

Ovarian tumors often metastasize and grow within the peritoneal cavity. Accordingly, intraperitoneal growth of ovarian tumors in mice are performed by injection of 2 million cells directly into the peritoneum of female mice. Mice are monitored for general health, physical activity, and appearance until they become moribund. At the time of sacrifice, the peritoneal cavity can be examined to determine tumor burden and lungs harvested to evaluate metastasis to distant sites. Alternatively, death can be used as an endpoint. The mice are then segregated into groups for the appropriate treatments, with 191P4D12 or control MAbs being injected i.p.

An advantage of xenograft cancer models is the ability to study neovascularization and angiogenesis. Tumor growth is partly dependent on new blood vessel development. Although the capillary system and developing blood network is of host origin, the initiation and architecture of the neovasculature is regulated by the xenograft tumor (Davidoff et al., Clin Cancer Res. (2001) 7:2870; Solesvik et al., Eur J Cancer Clin Oncol. (1984) 20:1295). The effect of antibody and small molecule on neovascularization is studied in accordance with procedures known in the art, such as by IHC analysis of tumor tissues and their surrounding microenvironment.

Ha22-2(2,4)6.1ADC inhibits formation lung, bladder, breast, and pancreatic cancer xenografts. These results indicate the utility of Ha22-2(2,4)6.1ADC in the treatment of local and advanced stages of cancer and preferably those cancers set forth in Table I.

191P4D12 ADCs:

Monoclonal antibodies were raised against 191P4D12 as described in the Example entitled "Generation of 191P4D12 Monoclonal Antibodies (MAbs)." Further the MAbs are conjugated to a toxin as described in the Example entitled "Antibody Drug Conjugation of Ha22-2(2,4)6.1 MAb" to form Ha22-2(2,4)6.1vcMMAE. The Ha22-2(2,4)6.1vcMMAE is characterized by FACS, and other methods known in the art to determine its capacity to bind 191P4D12.

Cell Lines and Xenografts:

The BT-483 and HPAC cells are maintained in DMEM, supplemented with L-glutamine and 10% FBS, as known in the art. AG-B8, AG-Panc4, AG-Panc2, AG-B1, AG-L4, and AG-Panc3 xenografts are maintained by serial propagation in SCID mice.

Evaluation of Ha22-2(2,4)6.1vcMMAE MAb in the Subcutaneous Tumor Formation Model of Human Lung Cancer Xenograft AG-L4 in SCID Mice In this experiment, patient-derived lung cancer xenograft AG-L4 was maintained by serial passages in SCID mice. Stock tumors were harvested sterilely and enzymatically digested into single cell suspensions. Two (2) million cells were implanted into the flank of individual SCID mice. Animals were then randomly assigned to seven groups: six (6) 191P4D12 antibody treated groups and a control antibody H3-1.10.1.2 group (n=10). All antibodies were dosed intraperitoneally at 750 µg/animal twice a week until the end of the study. Tumor growth was monitored using caliper measurements every 3 to 4 days. Tumor volume was calculated as $Width^2 \times Length/2$, where width is the smallest dimension and length is the largest dimension.

The results show that the 191P4D12 MAb did not significantly inhibit tumor growth in human lung cancer xenograft AG-L4 in SCID mice. Additionally, other 191P4D12 MAbs were utilized in this study. The results are not shown. (FIG. 12).

Evaluation of Ha22-2(2,4)6.1 MAb in the Subcutaneous Tumor Formation Model of Human Pancreatic Cancer Xenograft HPAC in SCID Mice In another experiment, human pancreatic cancer HPAC cells (2.0 millions/mouse) were injected into the flank of individual SCID mice. Animals were then randomly assigned to eight groups: seven (7) 191P4D12 antibody treated groups and a control antibody H3-1.4.1.2 group (n=10). All antibodies were dosed intraperitoneally at 500 µg/animal twice a week until the end of the study. Tumor growth was monitored using caliper measurements every 3 to 4 days. Tumor volume was calculated as $Width^2 \times Length/2$, where width is the smallest dimension and length is the largest dimension.

The results show that the 191P4D12 MAb did not inhibit tumor growth in a human pancreatic xenograft in SCID mice when compared to the control antibody. Additionally, other 191P4D12 MAbs were utilized in this study. The results are not shown. (FIG. 13).

Evaluation of Ha22-2(2,4)6.1 MAb in the subcutaneous tumor formation model of human pancreatic cancer xenograft AG-Panc3 in SCID mice.

In another experiment, patient-derived pancreatic cancer xenograft AG-Panc3 was maintained by serial passages in SCID mice. Stock tumors were harvested sterilely and minced into 1 mm³ pieces. Six pieces were implanted into the flank of individual SCID mice. Animals were then randomly assigned to the following cohorts (n=10): two (2) 191P4D12 MAb treated groups and a control antibody H3-1.4.1.2 group. All antibodies were dosed intraperitoneally at 500 µg/animal twice a week until the end of the study. Tumor growth was monitored using caliper measurements every 3 to 4 days. Tumor volume was calculated as $Width^2 \times Length/2$, where width is the smallest dimension and length is the largest dimension.

The results show that the 191P4D12 MAb did not inhibit tumor growth in a human pancreatic xenograft in SCID mice when compared to the control antibody. Additionally, other 191P4D12 MAbs were utilized in this study. The results are not shown. (FIG. 14).

Efficacy of Ha22-2(2,4)6.1-vcMMAE in Subcutaneous Established Human Lung Cancer Xenograft AG-L4 in SCID Mice In another experiment, patient-derived lung cancer xenograft AG-L13 was maintained by serial passages in SCID mice. Stock tumors were harvested sterilely and minced into 1 mm³ pieces. Six (6) pieces were implanted into the flank of individual SCID mice. Tumors were allowed to grow untreated until they reached an approximate volume of 200 mm³. The Ha22-2(2,4)6.1vcMMAE and the control ADC were dosed at 10 mg/kg every seven (7) days for two doses by intravenous bolus injection. The amount of ADC administered was based on the individual body weight of each animal obtained immediately prior to dosing. Tumor growth was monitored using caliper measurements every 3 to 4 days. Tumor volume was calculated as $Width^2 \times Length/2$, where width is the smallest dimension and length is the largest dimension.

The results show that treatment with Ha22-2(2,4)6.1-vcMMAE significantly inhibited the growth of AG-L4 lung cancer xenografts implanted subcutaneously in nude mice compared to the control ADC. Additionally, other 191P4D12 MAbs were utilized in this study. The results are not shown. (FIG. 15).

Efficacy of Ha22-2(2,4)6.1-vcMMAE in Subcutaneous Established Human Breast Cancer Xenograft BT-483 in SCID Mice In this experiment, human breast cancer BT-483 cells were used to generate stock xenografts, which were maintained by serial passages in SCID mice. Stock tumors were harvested sterilely and minced into 1 mm³ pieces. Six (6) pieces were implanted into the flank of individual SCID mice. Tumors were allowed to grow untreated until they reached an approximate volume of 100 mm³. The Ha22-2(2,4)6.1vcMMAE and the control ADC were dosed at 5 mg/kg every four (4) days for four (4) doses by intravenous bolus injection. The amount of ADC administered was based on the individual body weight of each animal obtained immediately prior to dosing. Tumor growth was monitored using caliper measurements every 3 to 4 days. Tumor volume was calculated as $Width^2 \times Length/2$, where width is the smallest dimension and length is the largest dimension.

The results show that treatment with Ha22-2(2,4)6.1-vcMMAE significantly inhibited the growth of BT-483 breast tumor xenografts implanted subcutaneously in SCID mice compared to the control ADC. Additionally, other 191P4D12 MAbs were utilized in this study. The results are not shown. (FIG. 16).

Efficacy of Ha22-2(2,4)6.1-vcMMAE in Subcutaneous Established Human Bladder Cancer Xenograft AG-B1 in SCID Mice In another experiment, patient-derived bladder cancer xenograft AG-B1 was maintained by serial passages in SCID mice. Stock tumors were harvested sterilely and minced into 1 mm$^3$ pieces. Six (6) pieces were implanted into the flank of individual SCID mice. Tumors were allowed to grow untreated until they reached an approximate volume of 230 mm$^3$. The Ha22-2(2,4)6.1vcMMAE and the control ADC were dosed at 4 mg/kg once by intravenous bolus injection. The amount of ADC administered was based on the individual body weight of each animal obtained immediately prior to dosing. Tumor growth was monitored using caliper measurements every 3 to 4 days. Tumor volume was calculated as Width$^2$×Length/2, where width is the smallest dimension and length is the largest dimension.

The results show that treatment with Ha22-2(2,4)6.1-vcMMAE significantly inhibited the growth of AG-B1 bladder cancer xenografts as compared to the control ADC. Additionally, other 191P4D12 MAbs were utilized in this study. The results are not shown. (FIG. 17).

Efficacy of Ha22-2(2,4)6.1-vcMMAE in Subcutaneous Established Human Pancreatic Cancer Xenograft AG-Panc2 in SCID Mice In another experiment, patient-derived pancreatic cancer xenograft AG-Panc2 was maintained by serial passages in SCID mice. Stock tumors were harvested sterilely and minced into 1 mm$^3$ pieces. Five (5) pieces were implanted into the flank of individual SCID mice. Tumors were allowed to grow untreated until they reached an approximate volume of 100 mm$^3$. The Ha22-2(2,4)6.1vcMMAE and control ADC were dosed at 5 mg/kg every four (4) days for four (4) doses by intravenous bolus injection. The amount of ADC administered was based on the individual body weight of each animal obtained immediately prior to dosing. Tumor growth was monitored using caliper measurements every 3 to 4 days. Tumor volume was calculated as Width$^2$×Length/2, where width is the smallest dimension and length is the largest dimension.

The results show that treatment with Ha22-2(2,4)6.1-vcMMAE significantly inhibited the growth of AG-Panc2 pancreatic cancer xenografts as compared to the control ADC. Additionally, other 191P4D12 MAbs were utilized in this study. The results are not shown. (FIG. 18).

Efficacy of Ha22-2(2,4)6.1-vcMMAE in Subcutaneous Established Human Pancreatic Cancer Xenograft AG-Panc4 in SCID Mice In another experiment, patient-derived pancreatic cancer xenograft AG-Panc4 was maintained by serial passages in SCID mice. Stock tumors were harvested sterilely and minced into 1 mm$^3$ pieces. Six (6) pieces were implanted into the flank of individual SCID mice. The Ha22-2(2,4)6.1vcMMAE and control ADC were dosed at 5 mg/kg every seven (7) days for three doses by intravenous bolus injection. The amount of ADC administered was based on the individual body weight of each animal obtained immediately prior to dosing. Tumor growth was monitored using caliper measurements every 3 to 4 days. Tumor volume was calculated as Width$^2$×Length/2, where width is the smallest dimension and length is the largest dimension.

The results show that treatment with Ha22-2(2,4)6.1-vcMMAE significantly inhibited the growth of AG-Panc4 pancreatic cancer xenografts as compared to the control ADC. Additionally, other 191P4D12 MAbs were utilized in this study. The results are not shown. (FIG. 19).

Efficacy of Ha22-2(2,4)6.1-vcMMAE at Comparative Dosage in Subcutaneous Established Human Bladder Cancer Xenograft AG-B8 in SCID Mice In this experiment, patient-derived bladder cancer xenograft AG-B8 was maintained by serial passages in SCID mice. Stock tumors were harvested sterilely and minced into 1 mm$^3$ pieces. Six (6) pieces were implanted into the flank of individual SCID mice. Tumors were allowed to grow untreated until they reached an approximate volume of 200 mm$^3$. Animals were then randomly assigned to the following three cohorts (n=6): two (2) Ha22-2(2,4)6.1-vcMMAE treated groups and a control ADC VCD37-5ce5p-vcMMAE group. Ha22-2(2,4)6.1-vcMMAE was dosed at 5 mg/kg or 10 mg/kg and the control ADC was given at 5 mg/kg. All ADCs were dosed once by intravenous bolus injection. The amount of ADC administered was based on the individual body weight of each animal obtained immediately prior to dosing. Tumor growth was monitored using caliper measurements every 3 to 4 days. Tumor volume was calculated as Width$^2$×Length/2, where width is the smallest dimension and length is the largest dimension.

The results show that treatment with Ha22-2(2,4)6.1vcMMAE at 10 mg/kg inhibited the growth of AG-B8 bladder cancer xenografts as compared to the Ha22-2(2,4)6.1vcMMAE at 5 mg/kg. (FIG. 20).

Conclusion

In summary, FIGS. 12-20, show that the 191P4D12 ADC entitled Ha22-2(2,4)6.1vcMMAE significantly inhibited the growth of tumors cells that express 191P4D12 when compared to control ADCs. Thus, the Ha22-2(2,4)6.1vcMMAE can be used for therapeutic purposes to treat and manage cancers set forth in Table I.

Example 8

Human Clinical Trials for the Treatment and Diagnosis of Human Carcinomas Through Use of 191P4D12 ADCs 191P4D12 ADCs are used in accordance with the present invention which specifically bind to 191P4D12, and are used in the treatment of certain tumors, preferably those listed in Table I. In connection with each of these indications, two clinical approaches are successfully pursued.

I.) Adjunctive therapy: In adjunctive therapy, patients are treated with 191P4D12 ADCs in combination with a chemotherapeutic or anti-neoplastic agent and/or radiation therapy or a combination thereof. Primary cancer targets, such as those listed in Table I, are treated under standard protocols by the addition of 191P4D12 ADCs to standard first and second line therapy. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents. These dosage reductions allow additional and/or prolonged therapy by reducing dose-related toxicity of the chemotherapeutic or biologic agent. 191P4D12 ADCs are utilized in several adjunctive clinical trials in combination with the chemotherapeutic or anti-neoplastic agents.

II.) Monotherapy: In connection with the use of the 191P4D12 ADCs in monotherapy of tumors, the 191P4D12 ADCs are administered to patients without a chemotherapeutic or anti-neoplastic agent. In one embodiment, monotherapy is conducted clinically in end-stage cancer patients with extensive metastatic disease. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents.

Dosage

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the antibody and/or ADC and the particular therapeutic or prophylactic effect to be achieved, and (b) the limitations inherent in the art of compounding such an active compound for the treatment of sensitivity in individuals.

An exemplary, non limiting range for a therapeutically effective amount of an 191P4D12 ADC administered in combination according to the invention is about 0.5 to about 10 mg/kg, about 1 to about 5 mg/kg, at least 1 mg/kg, at least 2 mg/kg, at least 3 mg/kg, or at least 4 mg/kg. Other exemplary non-limiting ranges are for example about 0.5 to about 5 mg/kg, or for example about 0.8 to about 5 mg/kg, or for example about 1 to about 7.5 mg/kg. The high dose embodiment of the invention relates to a dosage of more than 10 mg/kg. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Clinical Development Plan (CDP)

The CDP follows and develops treatments of 191P4D12 ADCs in connection with adjunctive therapy or monotherapy. Trials initially demonstrate safety and thereafter confirm efficacy in repeat doses. Trials are open label comparing standard chemotherapy with standard therapy plus 191P4D12 ADCs. As will be appreciated, one non-limiting criteria that can be utilized in connection with enrollment of patients is 191P4D12 expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAMA response); and, (iii) toxicity to normal cells that express 191P4D12. Standard tests and follow-up are utilized to monitor each of these safety concerns. 191P4D12 ADCs are found to be safe upon human administration.

Example 9

Detection of 191P4D12 Protein in Cancer Patient Specimens by IHC

Expression of 191P4D12 protein by immunohistochemistry was tested in patient tumor specimens from (i) bladder, (ii) breast, (iii) pancreatic, (iv) lung, (v) ovarian cancer, (vi) esophageal, and (vii) head and neck patients. Briefly, formalin fixed, paraffin wax-embedded tissues were cut into four (4) micron sections and mounted on glass slides. The sections were de-waxed, rehydrated and treated with EDTA antigen retrieval solution (Biogenex, San Ramon, Calif.) in the EZ-Retriever microwave (Biogenex, San Ramon, Calif.) for 30 minutes at 95° C. Sections were then treated with 3% hydrogen peroxide solution to inactivate endogenous peroxidase activity. Serum-free protein block (Dako, Carpenteria, Calif.) was used to inhibit non-specific binding prior to incubation with monoclonal mouse anti-191P4D12 antibody or an isotype control. Subsequently, the sections were treated with the Super Sensitive™ Polymer-horseradish peroxidase (HRP) Detection System which consists of an incubation in Super Enhancer™ reagent followed by an incubation with polymer-HRP secondary antibody conjugate (BioGenex, San Ramon, Calif.). The sections were then developed using the DAB kit (BioGenex, San Ramon, Calif.). Nuclei were stained using hematoxylin, and analyzed by bright field microscopy. Specific staining was detected in patient specimens using the 191P4D12 immunoreactive antibody, as indicated by the brown staining. (See, FIGS. 21(A), 21(C), 21(E), 21(G), 21(I), 21(K), and 21(M)). In contrast, the control antibody did not stain either patient specimen. (See, FIGS. 21(B), 21(D), 21(F), 21(H), 21(J), 21(L), and 21(N)).

The results show expression of 191P4D12 in the tumor cells of patient bladder, breast, pancreatic, lung, ovarian, esophageal, and head and neck cancer tissues. These results indicate that 191P4D12 is expressed in human cancers and that antibodies directed to this antigen and the antibody drug conjugate designated Ha22-2(2,4)6.1vcMMAE) are useful for diagnostic and therapeutic purposes. (FIG. 21).

Example 10

Determining the Binding Epitope of Ha22-2(2,4)6.1 MAb

The 191P4D12 protein of human, cynomolgus, rat and murine origin was overexpressed recombinantly in a PC3 cell line to determine cross-reactivity of Ha22-2(2,4)6.1 to these orthologs. It was shown that Ha22-2(2,4)6.1 strongly cross-reacts with cynomolgus and rat orthologs of 191P4D12 (FIG. 23). EC50 binding values are shown in Table VII. Binding of Ha22-2(2,4)6.1 to murine ortholog shows a significant reduction in binding EC50 value, which shows important amino acid substitutions in the V domain (as compared to human and rat sequences) affected affinity of Ha22-2(2,4)6.1 to 191P4D12.

Table VIII shows aa 1-180 protein sequence alignment of 191P4D12 orthologs containing the V-domain. Only two amino acids in the rat ortholog sequence, Thr-75 and Ser-90, are substituted in the murine ortholog sequence for Ile and Asn respectively (marked in bold text). It should be noted that the corresponding amino acids in the human sequence are Ala-76 and Ser-91. To determine if these amino acids comprise the binding epitope of Ha22-2(2,4)6.1, several mutant constructs of 191P4D12 and its murine ortholog were generated and expressed in PC3 cells (Table IX). "Murine" amino acids were introduced instead of a standard alanine substitution mutagenesis into human sequence and vice versa in the mouse sequence.

Figure 24B:
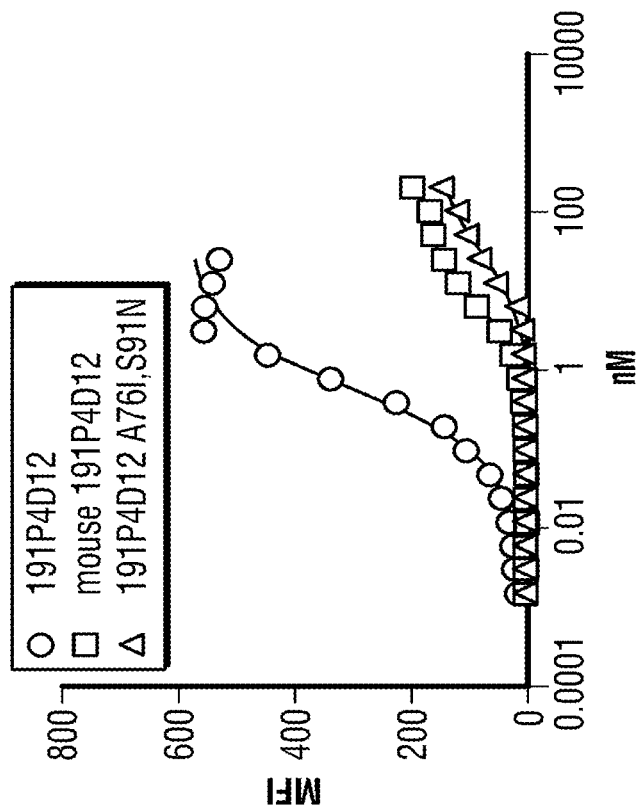
Figure 24A:
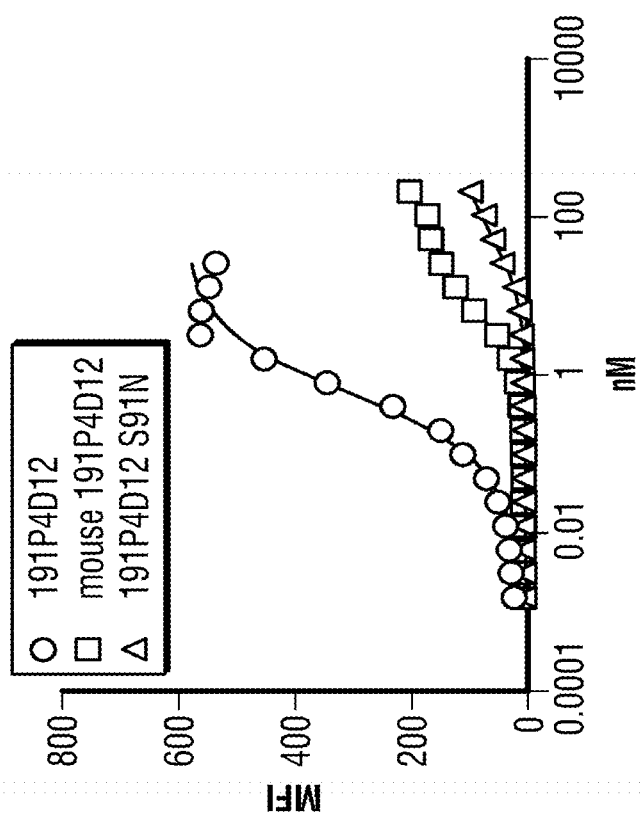

It was shown that mutation of Ser-91 to Asn in the 191P4D12 severely impairs the binding of Ha22-2(2,4)6.1 confirming that this amino acid, Ser-91, is essential for binding and must comprise the epitope recognized by the Ha22-2(2,4)6.1 MAb. Additional mutation of Ala in position 76 (A76I, S91N double mutant) was also introduced into 191P4D12. It was shown that binding of Ha22-2(2,4)6.1 to the double mutant A76I, S91N is very similar to murine ortholog binding (FIG. 24). Conversely, mutation of Asn-90 in the murine sequence to Ser dramatically improves binding of Ha22-2(2,4)6.1 to the murine mutant ortholog further confirming the importance of the amino acid in this position for binding of Ha22-2(2,4)6.1. Binding of Ha22-2(2,4)6.1 to the murine ortholog double mutant A90S, I75A appears very similar to human ortholog of 191P4D12.

Taken together, these data prove that Ser-91 and Ala-76 play a crucial role in binding of Ha22-2(2,4)6.1 to 191P4D12 protein on cell surface and constitute part of the epitope recognized by Ha22-2(2,4)6.1 on the surface of 191P4D12.

Figure 25:
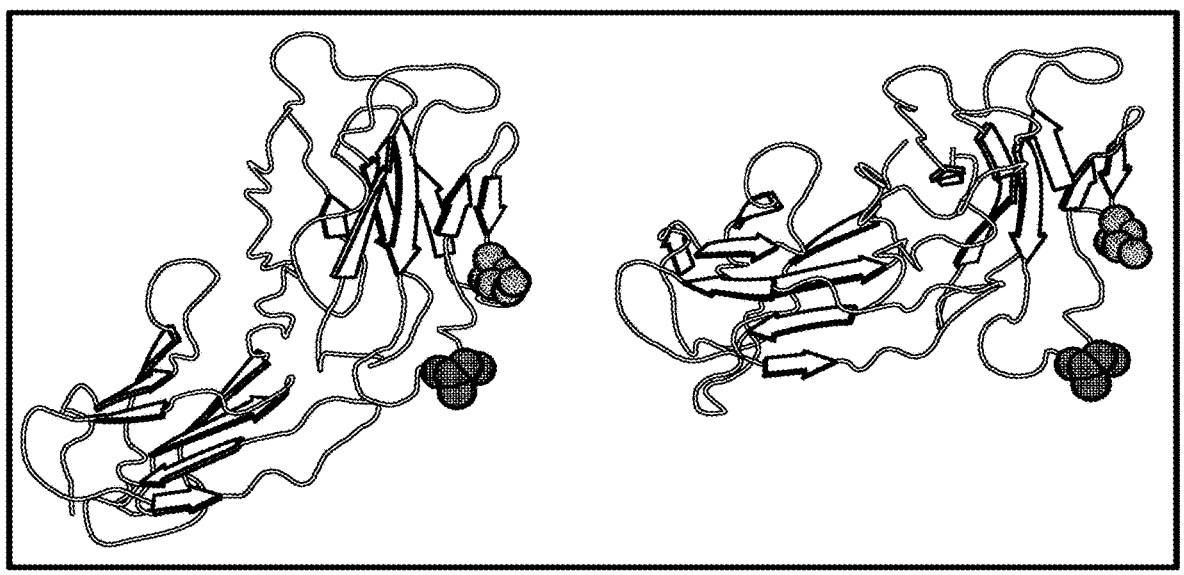
FIG. 25. Shows a model of the V-domain of 191P4D12 based on published crystal structure data for family members of 191P4D12 and Ig-domain containing proteins using PyMOL. The positions of Ala-76 (stippled) and Ser-91 (crosshatched) are shown.

To visualize this concept, we generated a computer model of the V-domain of 191P4D12 based on published crystal structure data for family members of 191P4D12 and Ig-domain containing proteins using PyMOL (FIG. 25). The positions of Ala-76 (stippled) and Ser-91 (crosshatched) are shown.

Additionally, to further refine the binding site of Ha22-2 (2,4)6.1 on 191P4D12 molecule, we designed and expressed a fragment of 191P4D12 corresponding to the V-domain on the surface of Rat(1)E cells. The following construct was generated in retroviral vector:

191P4D12 (aa1-150,347-510)

Figure 26A:
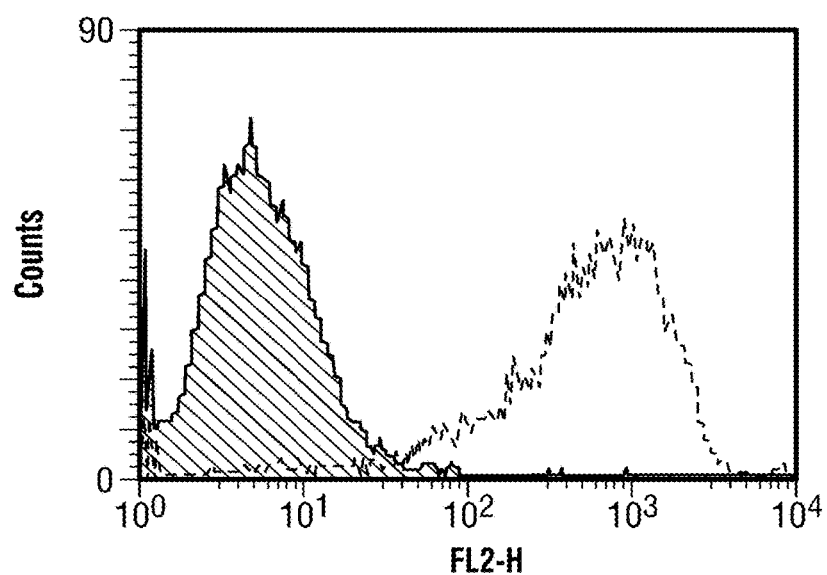
FIG. 26, which includes FIGS. 26A-C. Shows binding of Ha22-2(2,4)6.1 binds to V-domain expressing cells (FIG. 26A) as well as wild-type 191P4D12 (FIG. 26B), but not to C1C2 domain expressing cells generated earlier (FIG. 26C).
Figure 26B:
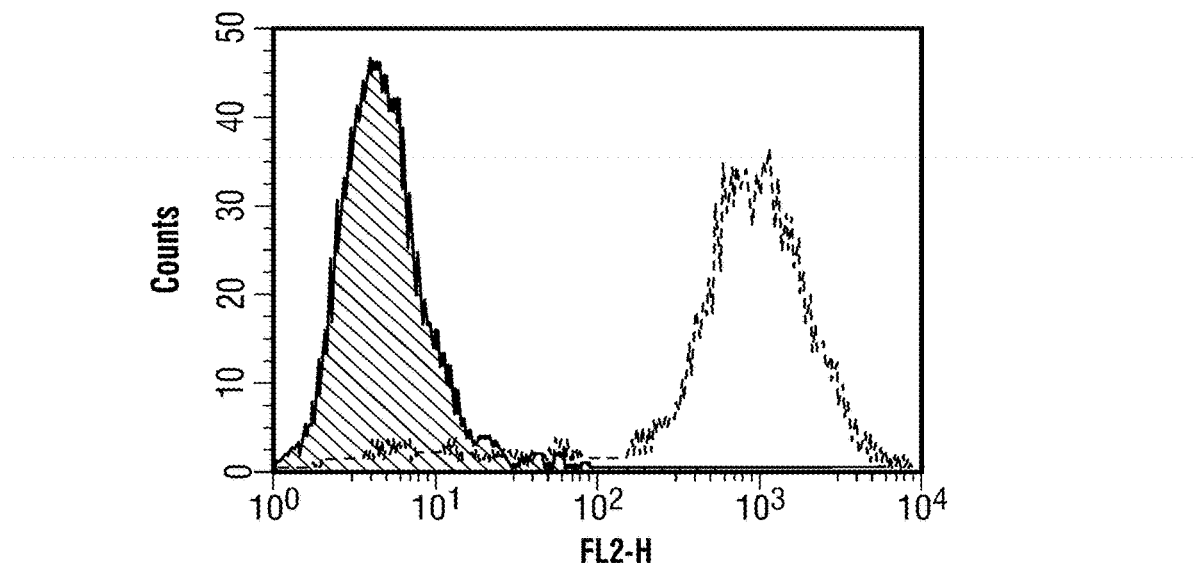
Figure 26C:
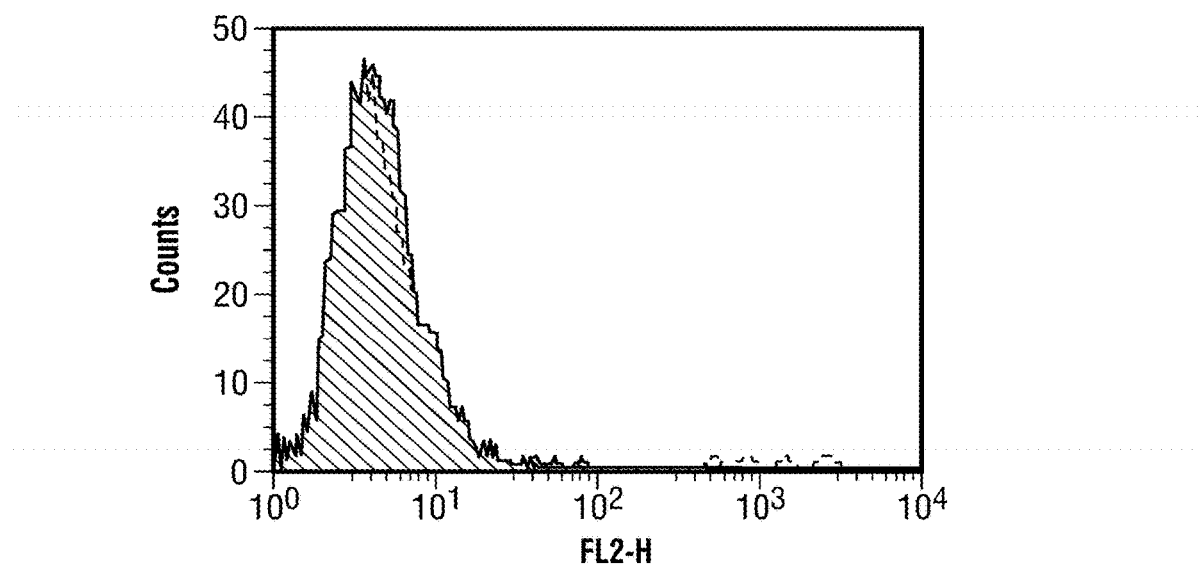

Binding of Ha22-2(2,4)6.1 MAb was assessed by FACS. As shown in FIG. 26, Ha22-2(2,4)6.1 binds to V-domain expressing cells (A) as well as wild-type 191P4D12 (B), but not to C1C2 domain expressing cells generated earlier (C). This proves the binding site for this antibody is located in the V-domain of 191P4D12 within first 150 amino acids.

The results show that the Ha22-2(2,4)6.1 MAb binds to the v-domain of the 191P4D12 protein from position aa 1-150 and additionally shows that the specific epitope comprising aa Ser-91 and aa Ala-76 are critical for binding the Ha22-2(2,4)6.1 MAb.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLES

TABLE I

Tissues that express 191P4D12 when malignant.

Colon
Pancreas
Ovarian
Breast
Lung
Bladder

TABLE II

Amino Acid Abbreviations

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

Amino Acid Substitution Matrix
Adapted from the GCG Software 9.0 BLOSUM62 amino acid substitution matrix (block substitution matrix). The higher the value, the more likely a substitution is found in related, natural proteins.

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | −2 | −1 | −2 | 0 | −2 | −1 | −1 | −1 | −1 | −2 | −1 | −1 | −1 | 1 | 0 | 0 | −3 | −2 | A |
|   | 9 | −3 | −4 | −2 | −3 | −3 | −1 | −3 | −1 | −1 | −3 | −3 | −3 | −3 | −1 | −1 | −1 | −2 | −2 | C |
|   |   | 6 | 2 | −3 | −1 | −1 | −3 | −1 | −4 | −3 | 1 | −1 | 0 | −2 | 0 | −1 | −3 | −4 | −3 | D |
|   |   |   | 5 | −3 | −2 | 0 | −3 | 1 | −3 | −2 | 0 | −1 | 2 | 0 | 0 | −1 | −2 | −3 | −2 | E |

TABLE III-continued

Amino Acid Substitution Matrix

Adapted from the GCG Software 9.0 BLOSUM62 amino acid substitution matrix (block substitution matrix). The higher the value, the more likely a substitution is found in related, natural proteins.

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
|   |   |   |   | 6 | -3 | -1 | 0 | -3 | 0 | 0 | -3 | -4 | -3 | -3 | -2 | -2 | -1 | 1 | 3 | F |
|   |   |   |   |   | 6 | -2 | -4 | -2 | -4 | -3 | 0 | -2 | -2 | -2 | 0 | -2 | -3 | -2 | -3 | G |
|   |   |   |   |   |   | 8 | -3 | -1 | -3 | -2 | 1 | -2 | 0 | 0 | -1 | -2 | -3 | -2 | 2 | H |
|   |   |   |   |   |   |   | 4 | -3 | 2 | 1 | -3 | -3 | -3 | -3 | -2 | -1 | 3 | -3 | -1 | I |
|   |   |   |   |   |   |   |   | 5 | -2 | -1 | 0 | -1 | 1 | 2 | 0 | -1 | -2 | -3 | -2 | K |
|   |   |   |   |   |   |   |   |   | 4 | 2 | -3 | -3 | -2 | -2 | -2 | -1 | 1 | -2 | -1 | L |
|   |   |   |   |   |   |   |   |   |   | 5 | -2 | -2 | 0 | -1 | -1 | -1 | 1 | -1 | -1 | M |
|   |   |   |   |   |   |   |   |   |   |   | 6 | -2 | 0 | 0 | 1 | 0 | -3 | -4 | -2 | N |
|   |   |   |   |   |   |   |   |   |   |   |   | 7 | -1 | -2 | -1 | -1 | -2 | -4 | -3 | P |
|   |   |   |   |   |   |   |   |   |   |   |   |   | 5 | 1 | 0 | -1 | -2 | -2 | -1 | Q |
|   |   |   |   |   |   |   |   |   |   |   |   |   |   | 5 | -1 | -1 | -3 | -3 | -2 | R |
|   |   |   |   |   |   |   |   |   |   |   |   |   |   |   | 4 | 1 | -2 | -3 | -2 | S |
|   |   |   |   |   |   |   |   |   |   |   |   |   |   |   |   | 5 | 0 | -2 | -2 | T |
|   |   |   |   |   |   |   |   |   |   |   |   |   |   |   |   |   | 4 | -3 | -1 | V |
|   |   |   |   |   |   |   |   |   |   |   |   |   |   |   |   |   |   | 11 | 2 | W |
|   |   |   |   |   |   |   |   |   |   |   |   |   |   |   |   |   |   |   | 7 | Y |

TABLE IV

General Method for Synthesis of vcMMAE

$$AA_2 + \text{[Dil intermediate: NH(Dil), OCH}_3\text{, OtBu]} \longrightarrow AA_1 + AA_2\text{-Dil}$$

$$\text{[Boc-N-pyrrolidine-OCH}_3\text{-COOH, Dap]} + AA_5$$

$$\downarrow$$

$$AA_1\text{-}AA_2\text{-Dil-Dap-}AA_5$$

$$\downarrow$$

$$\text{Linker-}AA_1\text{-}AA_2\text{-Dil-Dap-}AA_5$$

Where: AA1 = Amino Acid 1
AA2 = Amino Acid 2
AA5 = Amino Acid 5
DIL = Dolaisoleuine
DAP = Dolaproine
Linker = Val-Cit (vc)

TABLE V

Biacore association and dissociation rates and resulting affinity calculation

|  | $k_{on}$, M-1s-1 | $k_{off}$, s-1 | $K_D$, M |
|---|---|---|---|
| Ha22-2(2,4)6.1 | 3.8E+05 | 5.8E-03 | 1.6E-08 |
| Ha22-2(2,4)6.1vcMMAE | 4.5E+05 | 5.2E-03 | 1.1E-08 |

TABLE VI

191P4D12 constructs used in domain mapping assay

| Constructs | Name |
|---|---|
| 191P4D12 (aa 1-242, 347-510) expressing line | VC1, Rat1(E) expressing line |
| 191P4D12 (aa 1-31, 147-510) expressing line | C1C2, Rat1(E) |
| 191P4D12 (aa 1-242) | mFc-VC1, fusion protein |
| 191P4D12 (aa 1-31, 147-346) | mFc-C1C2, fusion protein |
| 191P4D12 (aa 1-141) | mFc-V, fusion protein |

TABLE VII

|  | PC3-191P4D12 | Cyno ortholog | Rat ortholog | Murine ortholog |
|---|---|---|---|---|
| Bmax (MFI) | 816 | 1146 | 679 | 325 |
| EC$_{50}$ (nM) | 0.28 | 0.30 | 0.44 | 70.3 |

TABLE VIII (SEQ ID NOS: 11-13, in order of appearance)

```
mouse    MPLSLGAEMWGPEAWLR-LLFLASFTGQYSAGELETSDVVTVVLGQDAKLPCFYRGDPDE
59
rat      MPLSLGAEMWGPEAWLL-LLFLASFTGRYSAGELETSDLVTVVLGQDAKLPCFYRGDPDE
59
human    MPLSLGAEMWGPEAWLLLLLLLASFTGRCPAGELETSDVVTVVLGQDAKLPCFYRGDSGE
60
         **************  :**** :***:***************..* mouse    QVGQVAWARVDPNEGIRELALLHSKYGLHVNPAYEDRVEQPPPPRDPLDGSVLLRNAVQA
119
rat      QVGQVAWARVDPNEGTRELALLHSKYGLHVSPAYEDRVEQPPPPRDPLDGSILLRNAVQA
119
human    QVGQVAWARVDAGEGAQELALLHSKYGLHVSPAYEGRVEQPPPPRNPLDGSVLLRNAVQA
120
         *********...:**********..****:*:****** mouse    DEGEYECRVSTFPAGSFQARMRLRVLVPPLPSLNPGPPLEEGQGLTLAASCTAEGSPAPS
179
rat      DEGEYECRVSTFPAGSFQARMRLRVLVPPLPSLNPGPPLEEGQGLTLAASCTAEGSPAPS
179
human    DEGEYECRVSTFPAGSFQARLRLRVLVPPLPSLNPGPALEEGQGLTLAASCTAEGSPAPS
180
         ********************:***************.***********************
```

TABLE IX

| Wild type constructs | Mutant constructs | Double-mutant constructs |
|---|---|---|
| 191P4D12, wild type | S91N | S91N, A76I |
| Murine ortholog of 191P4D12, wild type | N90S | N90S, I75A |

The invention claimed is:

1. An antibody drug conjugate comprising an anti-191P4D12 antibody or antigen binding fragment thereof conjugated to monomethyl auristatin E (MMAE), wherein the antibody or antigen binding fragment thereof comprises a heavy chain variable region comprising an amino acid sequence at least 80% homologous to the heavy chain variable region amino acid sequence set forth in SEQ ID NO:7 and a light chain variable region comprising an amino acid sequence at least 80% homologous to the light chain variable region amino acid sequence set forth in SEQ ID NO:8,
wherein the antibody or antigen binding fragment thereof comprises a heavy chain variable region comprising complementarity determining regions (CDRs) comprising the amino acid sequences of the CDRs in the heavy chain variable region sequence set forth in SEQ ID NO: 7 and a light chain variable region comprising CDRs comprising the amino acid sequences of the CDRs in the light chain variable region sequence set forth in SEQ ID NO: 8.

2. The antibody drug conjugate of claim 1, wherein the antibody or antigen binding fragment thereof comprises a heavy chain variable region comprising an amino acid sequence at least 85%, 86%, 87%, 88%, 89%, 90%, 91%, 92%, 93%, 94%, 95%, 96%, 97%, 98%, or 99% homologous to the heavy chain variable region amino acid sequence set forth in SEQ ID NO:7 and a light chain variable region comprising an amino acid sequence at least 85%, 86%, 87%, 88%, 89%, 90%, 91%, 92%, 93%, 94%, 95%, 96%, 97%, 98%, or 99% homologous to the light chain variable region amino acid sequence set forth in SEQ ID NO:8.

3. The antibody drug conjugate of claim 1, wherein the antigen binding fragment thereof is a Fab, F(ab')2, Fv or scFv.

4. The antibody drug conjugate of claim 1, wherein the antibody is a fully human antibody.

5. The antibody drug conjugate of claim 1, wherein the antibody or antigen binding fragment thereof is recombinantly produced.

6. The antibody drug conjugate of claim 1, wherein the antibody or antigen binding fragment thereof is conjugated to MMAE via a linker.

7. The antibody drug conjugate of claim 6, wherein the linker comprises valine-citrulline.

8. The antibody drug conjugate of claim 6, wherein the linker is an enzyme-cleavable linker, and wherein the linker forms a bond with a sulfur atom of the antibody or antigen binding fragment thereof.

9. The antibody drug conjugate of claim 6, wherein the linker has a formula of: $-A_a-W_w-Y_y-$; wherein -A- is a stretcher unit, a is 0 or 1; —W— is an amino acid unit, w is an integer ranging from 0 to 12; and —Y— is a spacer unit, y is 0, 1, or 2; wherein the stretcher unit has the structure of Formula (1) below; the amino acid unit is valine-citrulline; and the spacer unit is a PAB group having the structure of Formula (2) below;

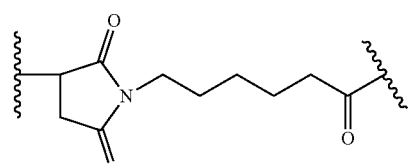

Formula (1)

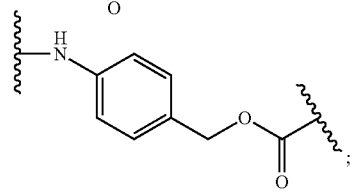

Formula (2)

and
wherein the stretcher unit forms a bond with a sulfur atom of the antibody or antigen binding fragment thereof; and wherein the spacer unit is linked to MMAE via a carbamate group.

10. The antibody drug conjugate of claim 1, comprising from 1 to 10 units of MMAE per antibody or antigen binding fragment thereof.

11. The antibody drug conjugate of claim 1, comprising from 2 to 5 units of MMAE per antibody or antigen binding fragment thereof.

12. The antibody drug conjugate of claim 1, wherein the antibody drug conjugate has the following structure:

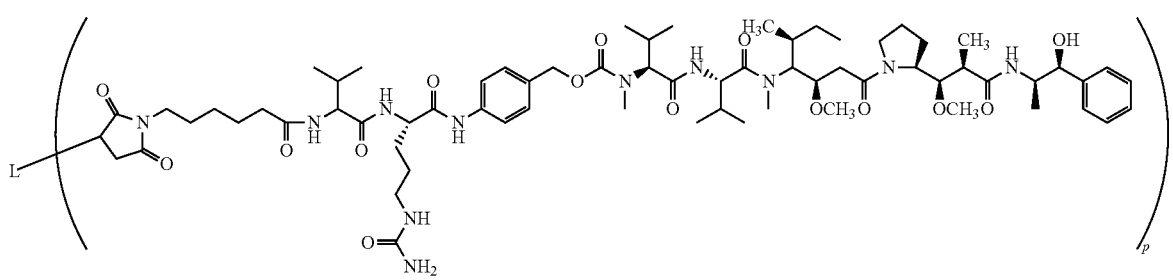

wherein L- represents the anti-191P4D12 antibody or antigen binding fragment thereof and p ranges from 1 to 10.

13. The antibody drug conjugate of claim 12, wherein the antibody comprises a heavy chain comprising the amino acid sequence ranging from 20th amino acid residue to 466th amino acid residue of SEQ ID NO:7 and a light chain comprising the amino acid sequence ranging from 23rd amino acid residue to 236th amino acid residue of SEQ ID NO:8, and wherein p ranges from 2 to 7.

14. A composition comprising a plurality of the antibody drug conjugates of claim 12, wherein the average p value for the antibody drug conjugates in the composition is about 3.8.

15. A pharmaceutical composition comprising the antibody drug conjugate of claim 12 and a pharmaceutically acceptable excipient, wherein the average p value for the antibody drug conjugates in the pharmaceutical composition is about 3.8.

16. A method of treating cancer in a subject, comprising administering to the subject a therapeutically effective amount of the pharmaceutical composition of claim 15.

17. The antibody drug conjugate of claim 12, wherein P ranges from 2 to 5.

18. The antibody drug conjugate of claim 12, wherein the antibody or antigen binding fragment thereof comprises the heavy chain variable region comprising the amino acid sequence ranging from 20th amino acid residue to 136th amino acid residue of SEQ ID NO:7 and the light chain variable region comprising the amino acid sequence ranging from 23rd amino acid residue to 130th amino acid residue of SEQ ID NO:8, and wherein p ranges from 2 to 7.

19. The antibody drug conjugate of claim 18, wherein the antibody is a fully human monoclonal antibody, wherein the antibody is an IgG1, and wherein the light chain is a kappa light chain.

20. A pharmaceutical composition comprising the antibody drug conjugate of claim 1 and a pharmaceutically acceptable excipient.

21. A method of treating cancer in a subject, comprising administering to the subject a therapeutically effective amount of the pharmaceutical composition of claim 20.

22. A method of treating cancer in a subject, comprising administering to the subject a therapeutically effective amount of the antibody drug conjugate of claim 1.

23. The method of claim 22, wherein the subject is a human subject.

24. The method of claim 23, wherein the cancer is head and neck cancer, pancreatic cancer, lung cancer, bladder cancer, or breast cancer.

25. The method of claim 24, wherein the cancer is pancreatic cancer.

26. The method of claim 24, wherein the cancer is lung cancer.

27. The method of claim 24, wherein the cancer is bladder cancer.

28. The method of claim 27, wherein the bladder cancer is advanced bladder cancer.

29. The method of claim 27, wherein the bladder cancer is metastatic bladder cancer.

30. The method of claim 24, wherein the cancer is breast cancer.

31. The method of claim 24, wherein the cancer is head and neck cancer.

32. The method of claim 22, wherein the method further comprises administering radiation or chemotherapeutic agent.

* * * * *

SEQUENCE LISTING

<160> NUMBER OF SEQ ID NOS: 13

<210> SEQ ID NO 1
<211> LENGTH: 3464
<212> TYPE: DNA
<213> ORGANISM: Homo sapiens
<220> FEATURE:
<221> NAME/KEY: CDS
<222> LOCATION: (264)...(1796)
<220> FEATURE:
<221> NAME/KEY: misc_feature
<222> LOCATION: (1)...(3464)
<223> OTHER INFORMATION: 191P4D12

<400> SEQUENCE: 1

```
ggccgtcgtt gttggccaca gcgtgggaag cagctctggg ggagctcgga gctcccgatc      60
acggcttctt gggggtagct acggctgggt gtgtagaacg gggccggggc tggggctggg     120 tccccctagtg gagacccaag tgcgagaggc aagaactctg cagcttcctg ccttctgggt    180
cagttcctta ttcaagtctg cagccggctc ccagggagat ctcggtggaa cttcagaaac    240
gctgggcagt ctgccttca acc atg ccc ctg tcc ctg gga gcc gag atg tgg    293
                        Met Pro Leu Ser Leu Gly Ala Glu Met Trp
                         1               5                  10
```

```
ggg cct gag gcc tgg ctg ctg ctg cta ctg ctg gca tca ttt aca      341
Gly Pro Glu Ala Trp Leu Leu Leu Leu Leu Leu Ala Ser Phe Thr
            15                  20                  25 ggc cgg tgc ccc gcg ggt gag ctg gag acc tca gac gtg gta act gtg  389
Gly Arg Cys Pro Ala Gly Glu Leu Glu Thr Ser Asp Val Val Thr Val
                30                  35                  40 gtg ctg ggc cag gac gca aaa ctg ccc tgc ttc tac cga ggg gac tcc  437
Val Leu Gly Gln Asp Ala Lys Leu Pro Cys Phe Tyr Arg Gly Asp Ser
            45                  50                  55 ggc gag caa gtg ggg caa gtg gca tgg gct cgg gtg gac gcg ggc gaa  485
Gly Glu Gln Val Gly Gln Val Ala Trp Ala Arg Val Asp Ala Gly Glu
        60                  65                      70 ggc gcc cag gaa cta gcg cta ctg cac tcc aaa tac ggg ctt cat gtg  533
Gly Ala Gln Glu Leu Ala Leu Leu His Ser Lys Tyr Gly Leu His Val
75                  80                  85                  90 agc ccg gct tac gag ggc cgc gtg gag cag ccg ccg ccc cca cgc aac  581
Ser Pro Ala Tyr Glu Gly Arg Val Glu Gln Pro Pro Pro Pro Arg Asn
                95                  100                 105 ccc ctg gac ggc tca gtg ctc ctg cgc aac gca gtg cag gcg gat gag  629
Pro Leu Asp Gly Ser Val Leu Leu Arg Asn Ala Val Gln Ala Asp Glu
            110                 115                 120 ggc gag tac gag tgc cgg gtc agc acc ttc ccc gcc ggc agc ttc cag  677
Gly Glu Tyr Glu Cys Arg Val Ser Thr Phe Pro Ala Gly Ser Phe Gln
        125                 130                 135 gcg cgg ctg cgg ctc cga gtg ctg gtg cct ccc ctg ccc tca ctg aat  725
Ala Arg Leu Arg Leu Arg Val Leu Val Pro Pro Leu Pro Ser Leu Asn
    140                 145                 150 cct ggt cca gca cta gaa gag ggc cag ggc ctg acc ctg gca gcc tcc  773
Pro Gly Pro Ala Leu Glu Glu Gly Gln Gly Leu Thr Leu Ala Ala Ser
155                 160                 165                 170 tgc aca gct gag ggc agc cca gcc ccc agc gtg acc tgg gac acg gag  821
Cys Thr Ala Glu Gly Ser Pro Ala Pro Ser Val Thr Trp Asp Thr Glu
                175                 180                 185 gtc aaa ggc aca acg tcc agc cgt tcc ttc aag cac tcc cgc tct gct  869
Val Lys Gly Thr Thr Ser Ser Arg Ser Phe Lys His Ser Arg Ser Ala
            190                 195                 200 gcc gtc acc tca gag ttc cac ttg gtg cct agc cgc agc atg aat ggg  917
Ala Val Thr Ser Glu Phe His Leu Val Pro Ser Arg Ser Met Asn Gly
        205                 210                 215 cag cca ctg act tgt gtg gtg tcc cat cct ggc ctg ctc cag gac caa  965
Gln Pro Leu Thr Cys Val Val Ser His Pro Gly Leu Leu Gln Asp Gln
    220                 225                 230 agg atc acc cac atc ctc cac gtg tcc ttc ctt gct gag gcc tct gtg  1013
Arg Ile Thr His Ile Leu His Val Ser Phe Leu Ala Glu Ala Ser Val
235                 240                 245                 250 agg ggc ctt gaa gac caa aat ctg tgg cac att ggc aga gaa gga gct  1061
Arg Gly Leu Glu Asp Gln Asn Leu Trp His Ile Gly Arg Glu Gly Ala
                255                 260                 265 atg ctc aag tgc ctg agt gaa ggg cag ccc ctc cca tac aac tgg      1109
Met Leu Lys Cys Leu Ser Glu Gly Gln Pro Pro Pro Ser Tyr Asn Trp
            270                 275                 280 aca cgg ctg gat ggg cct ctg ccc agt ggg gta cga gtg gat ggg gac  1157
Thr Arg Leu Asp Gly Pro Leu Pro Ser Gly Val Arg Val Asp Gly Asp
        285                 290                 295 act ttg ggc ttt ccc cca ctg acc act gag cac agc ggc atc tac gtc  1205
Thr Leu Gly Phe Pro Pro Leu Thr Thr Glu His Ser Gly Ile Tyr Val
    300                 305                 310 tgc cat gtc agc aat gag ttc tcc tca agg gat tct cag gtc act gtg  1253
Cys His Val Ser Asn Glu Phe Ser Ser Arg Asp Ser Gln Val Thr Val
```

|  |  |  |  |  |  |  |  |  |  |  |  |  |  |  |  |
|---|---|---|---|---|---|---|---|---|---|---|---|---|---|---|---|
| gat | gtt | ctt | gac | ccc | cag | gaa | gac | tct | ggg | aag | cag | gtg | gac | cta | gtg |
| Asp | Val | Leu | Asp | Pro | Gln | Glu | Asp | Ser | Gly | Lys | Gln | Val | Asp | Leu | Val |
|     |     |     |     | 335 |     |     |     |     | 340 |     |     |     |     | 345 |     |

```
315                 320                 325                 330 gat gtt ctt gac ccc cag gaa gac tct ggg aag cag gtg gac cta gtg      1301
Asp Val Leu Asp Pro Gln Glu Asp Ser Gly Lys Gln Val Asp Leu Val
                335                 340                 345 tca gcc tcg gtg gtg gtg gtg ggt gtg atc gcc gca ctc ttg ttc tgc      1349
Ser Ala Ser Val Val Val Val Gly Val Ile Ala Ala Leu Leu Phe Cys
                350                 355                 360 ctt ctg gtg gtg gtg gtg gtg ctc atg tcc cga tac cat cgg cgc aag      1397
Leu Leu Val Val Val Val Val Leu Met Ser Arg Tyr His Arg Arg Lys
                365                 370                 375 gcc cag cag atg acc cag aaa tat gag gag gag ctg acc ctg acc agg      1445
Ala Gln Gln Met Thr Gln Lys Tyr Glu Glu Glu Leu Thr Leu Thr Arg
            380                 385                 390 gag aac tcc atc cgg agg ctg cat tcc cat cac acg gac ccc agg agc      1493
Glu Asn Ser Ile Arg Arg Leu His Ser His His Thr Asp Pro Arg Ser
395                 400                 405                 410 cag ccg gag gag agt gta ggg ctg aga gcc gag ggc cac cct gat agt      1541
Gln Pro Glu Glu Ser Val Gly Leu Arg Ala Glu Gly His Pro Asp Ser
                415                 420                 425 ctc aag gac aac agt agc tgc tct gtg atg agt gaa gag ccc gag ggc      1589
Leu Lys Asp Asn Ser Ser Cys Ser Val Met Ser Glu Glu Pro Glu Gly
                430                 435                 440 cgc agt tac tcc acg ctg acc acg gtg agg gag ata gaa aca cag act      1637
Arg Ser Tyr Ser Thr Leu Thr Thr Val Arg Glu Ile Glu Thr Gln Thr
                445                 450                 455 gaa ctg ctg tct cca ggc tct ggg cgg gcc gag gag gag gaa gat cag      1685
Glu Leu Leu Ser Pro Gly Ser Gly Arg Ala Glu Glu Glu Glu Asp Gln
        460                 465                 470 gat gaa ggc atc aaa cag gcc atg aac cat ttt gtt cag gag aat ggg      1733
Asp Glu Gly Ile Lys Gln Ala Met Asn His Phe Val Gln Glu Asn Gly
475                 480                 485                 490 acc cta cgg gcc aag ccc acg ggc aat ggc atc tac atc aat ggg cgg      1781
Thr Leu Arg Ala Lys Pro Thr Gly Asn Gly Ile Tyr Ile Asn Gly Arg
                495                 500                 505 gga cac ctg gtc tga cccaggcctg cctcccttcc ctaggcctgg ctccttctgt      1836
Gly His Leu Val
            510 tgacatggga gattttagct catcttgggg gcctccttaa acaccccat ttcttgcgga    1896 agatgctccc catcccactg actgcttgac ctttacctcc aacccttctg ttcatcggga    1956 gggctccacc aattgagtct ctcccaccat gcatgcaggt cactgtgtgt gtgcatgtgt    2016 gcctgtgtga gtgttgactg actgtgtgtg tgtggagggg tgactgtccg tggaggggtg    2076 actgtgtccg tggtgtgtat tatgctgtca tatcagagtc aagtgaactg tggtgtatgt    2136 gccacgggat ttgagtggtt gcgtgggcaa cactgtcagg gtttggcgtg tgtgtcatgt    2196 ggctgtgtgt gacctctgcc tgaaaaagca ggtattttct cagaccccag agcagtatta    2256 atgatgcaga ggttggagga gagaggtgga gactgtggct cagacccagg tgtgcgggca    2316 tagctggagc tggaatctgc ctccggtgtg agggaacctg tctcctacca cttcggagcc    2376 atggggcaa gtgtgaagca gccagtccct gggtcagcca gaggcttgaa ctgttacaga     2436 agccctctgc cctctggtgg cctctgggcc tgctgcatgt acatattttc tgtaaatata    2496 catgcgccgg gagcttcttg caggaatact gctccgaatc acttttaatt tttttctttt    2556 tttttcttg cccttttccat tagttgtatt tttatttat ttttattttt attttttttt    2616 agagatggag tctcactatg ttgctcaggc tggccttgaa ctcctgggct caagcaatcc    2676 tcctgcctca gcctccctag tagctgggac tttaagtgta caccactgtg cctgctttga    2736
```

-continued

```
atcctttacg aagagaaaaa aaaaattaaa gaaagccttt agatttatcc aatgtttact    2796
actgggattg cttaaagtga ggcccctcca acaccagggg gttaattcct gtgattgtga    2856
aaggggctac ttccaaggca tcttcatgca ggcagcccct tgggagggca cctgagagct    2916
ggtagagtct gaaattaggg atgtgagcct cgtggttact gagtaaggta aaattgcatc    2976
caccattgtt tgtgatacct tagggaattg cttggacctg gtgacaaggg ctcctgttca    3036
atagtggtgt tggggagaga gagagcagtg attatagacc gagagagtag gagttgaggt    3096
gaggtgaagg aggtgctggg ggtgagaatg tcgcctttcc ccctgggttt tggatcacta    3156
attcaaggct cttctggatg tttctctggg ttggggctgg agttcaatga ggtttatttt    3216
tagctggccc acccagatac actcagccag aatacctaga tttagtaccc aaactcttct    3276
tagtctgaaa tctgctggat ttctggccta agggagaggc tcccatcctt cgttccccag    3336
ccagcctagg acttcgaatg tggagcctga agatctaaga tcctaacatg tacattttat    3396
gtaaatatgt gcatatttgt acataaaatg atattctgtt tttaaataaa cagacaaaac    3456
ttgaaaaa                                                              3464
```

<210> SEQ ID NO 2
<211> LENGTH: 510
<212> TYPE: PRT
<213> ORGANISM: Homo sapiens
<220> FEATURE:
<221> NAME/KEY: misc_feature
<222> LOCATION: (1)...(510)
<223> OTHER INFORMATION: 191P4D12

<400> SEQUENCE: 2

```
Met Pro Leu Ser Leu Gly Ala Glu Met Trp Gly Pro Glu Ala Trp Leu
1               5                   10                  15

Leu Leu Leu Leu Leu Leu Ala Ser Phe Thr Gly Arg Cys Pro Ala Gly
                20                  25                  30

Glu Leu Glu Thr Ser Asp Val Val Thr Val Val Leu Gly Gln Asp Ala
            35                  40                  45

Lys Leu Pro Cys Phe Tyr Arg Gly Asp Ser Gly Glu Gln Val Gly Gln
        50                  55                  60

Val Ala Trp Ala Arg Val Asp Ala Gly Glu Gly Ala Gln Glu Leu Ala
65                  70                  75                  80

Leu Leu His Ser Lys Tyr Gly Leu His Val Ser Pro Ala Tyr Glu Gly
                85                  90                  95

Arg Val Glu Gln Pro Pro Pro Arg Asn Pro Leu Asp Gly Ser Val
            100                 105                 110

Leu Leu Arg Asn Ala Val Gln Ala Asp Glu Gly Glu Tyr Glu Cys Arg
        115                 120                 125

Val Ser Thr Phe Pro Ala Gly Ser Phe Gln Ala Arg Leu Arg Leu Arg
    130                 135                 140

Val Leu Val Pro Pro Leu Pro Ser Leu Asn Pro Gly Pro Ala Leu Glu
145                 150                 155                 160

Glu Gly Gln Gly Leu Thr Leu Ala Ala Ser Cys Thr Ala Glu Gly Ser
                165                 170                 175

Pro Ala Pro Ser Val Thr Trp Asp Thr Glu Val Lys Gly Thr Thr Ser
            180                 185                 190

Ser Arg Ser Phe Lys His Ser Arg Ser Ala Ala Val Thr Ser Glu Phe
        195                 200                 205

His Leu Val Pro Ser Arg Ser Met Asn Gly Gln Pro Leu Thr Cys Val
```

```
                210                 215                 220
Val Ser His Pro Gly Leu Leu Gln Asp Gln Arg Ile Thr His Ile Leu
225                 230                 235                 240

His Val Ser Phe Leu Ala Glu Ala Ser Val Arg Gly Leu Glu Asp Gln
                245                 250                 255

Asn Leu Trp His Ile Gly Arg Glu Gly Ala Met Leu Lys Cys Leu Ser
            260                 265                 270

Glu Gly Gln Pro Pro Pro Ser Tyr Asn Trp Thr Arg Leu Asp Gly Pro
        275                 280                 285

Leu Pro Ser Gly Val Arg Val Asp Gly Asp Thr Leu Gly Phe Pro Pro
290                 295                 300

Leu Thr Thr Glu His Ser Gly Ile Tyr Val Cys His Val Ser Asn Glu
305                 310                 315                 320

Phe Ser Ser Arg Asp Ser Gln Val Thr Val Asp Val Leu Asp Pro Gln
                325                 330                 335

Glu Asp Ser Gly Lys Gln Val Asp Leu Val Ser Ala Ser Val Val Val
            340                 345                 350

Val Gly Val Ile Ala Ala Leu Leu Phe Cys Leu Leu Val Val Val Val
        355                 360                 365

Val Leu Met Ser Arg Tyr His Arg Arg Lys Ala Gln Gln Met Thr Gln
370                 375                 380

Lys Tyr Glu Glu Glu Leu Thr Leu Thr Arg Glu Asn Ser Ile Arg Arg
385                 390                 395                 400

Leu His Ser His His Thr Asp Pro Arg Ser Gln Pro Glu Glu Ser Val
                405                 410                 415

Gly Leu Arg Ala Glu Gly His Pro Asp Ser Leu Lys Asp Asn Ser Ser
            420                 425                 430

Cys Ser Val Met Ser Glu Glu Pro Glu Gly Arg Ser Tyr Ser Thr Leu
        435                 440                 445

Thr Thr Val Arg Glu Ile Glu Thr Gln Thr Glu Leu Leu Ser Pro Gly
450                 455                 460

Ser Gly Arg Ala Glu Glu Glu Asp Gln Asp Glu Gly Ile Lys Gln
465                 470                 475                 480

Ala Met Asn His Phe Val Gln Glu Asn Gly Thr Leu Arg Ala Lys Pro
                485                 490                 495

Thr Gly Asn Gly Ile Tyr Ile Asn Gly Arg Gly His Leu Val
            500                 505                 510

<210> SEQ ID NO 3
<211> LENGTH: 1432
<212> TYPE: DNA
<213> ORGANISM: Homo sapiens
<220> FEATURE:
<221> NAME/KEY: CDS
<222> LOCATION: (32)...(1432)
<220> FEATURE:
<221> NAME/KEY: misc_feature
<222> LOCATION: (1)...(1432)
<223> OTHER INFORMATION: Ha22-2(2,4)6.1 heavy chain

<400> SEQUENCE: 3
ggtgatcagc actgaacaca gaggactcac c atg gag ttg ggg ctg tgc tgg       52
                                   Met Glu Leu Gly Leu Cys Trp
                                   1               5 gtt ttc ctt gtt gct att tta gaa ggt gtc cag tgt gag gtg cag ctg    100
Val Phe Leu Val Ala Ile Leu Glu Gly Val Gln Cys Glu Val Gln Leu
        10                  15                  20
```

-continued

| | |
|---|---|
| gtg gag tct ggg gga ggc ttg gta cag cct ggg ggg tcc ctg aga ctc<br>Val Glu Ser Gly Gly Gly Leu Val Gln Pro Gly Gly Ser Leu Arg Leu<br>25                              30                          35 | 148 |
| tcc tgt gca gcc tct gga ttc acc ttc agt agc tat aac atg aac tgg<br>Ser Cys Ala Ala Ser Gly Phe Thr Phe Ser Ser Tyr Asn Met Asn Trp<br>40                            45                        50                       55 | 196 |
| gtc cgc cag gct cca ggg aag ggg ctg gag tgg gtt tca tac att agt<br>Val Arg Gln Ala Pro Gly Lys Gly Leu Glu Trp Val Ser Tyr Ile Ser<br>                    60                        65                          70 | 244 |
| agt agt agt agt acc ata tac tac gca gac tct gtg aag ggc cga ttc<br>Ser Ser Ser Ser Thr Ile Tyr Tyr Ala Asp Ser Val Lys Gly Arg Phe<br>75                            80                        85 | 292 |
| acc atc tcc aga gac aat gcc aag aac tca ctg tct ctg caa atg aac<br>Thr Ile Ser Arg Asp Asn Ala Lys Asn Ser Leu Ser Leu Gln Met Asn<br>                    90                        95                       100 | 340 |
| agc ctg aga gac gag gac acg gct gtg tat tac tgt gcg aga gca tac<br>Ser Leu Arg Asp Glu Asp Thr Ala Val Tyr Tyr Cys Ala Arg Ala Tyr<br>105                          110                        115 | 388 |
| tac tac ggt atg gac gtc tgg ggc caa ggg acc acg gtc acc gtc tcc<br>Tyr Tyr Gly Met Asp Val Trp Gly Gln Gly Thr Thr Val Thr Val Ser<br>120                          125                        130                       135 | 436 |
| tca gcc tcc acc aag ggc cca tcg gtc ttc ccc ctg gca ccc tcc tcc<br>Ser Ala Ser Thr Lys Gly Pro Ser Val Phe Pro Leu Ala Pro Ser Ser<br>                    140                        145                       150 | 484 |
| aag agc acc tct ggg ggc aca gcg gcc ctg ggc tgc ctg gtc aag gac<br>Lys Ser Thr Ser Gly Gly Thr Ala Ala Leu Gly Cys Leu Val Lys Asp<br>155                          160                        165 | 532 |
| tac ttc ccc gaa ccg gtg acg gtg tcg tgg aac tca ggc gcc ctg acc<br>Tyr Phe Pro Glu Pro Val Thr Val Ser Trp Asn Ser Gly Ala Leu Thr<br>170                          175                        180 | 580 |
| agc ggc gtg cac acc ttc ccg gct gtc cta cag tcc tca gga ctc tac<br>Ser Gly Val His Thr Phe Pro Ala Val Leu Gln Ser Ser Gly Leu Tyr<br>                    185                        190                       195 | 628 |
| tcc ctc agc agc gtg gtg acc gtg ccc tcc agc agc ttg ggc acc cag<br>Ser Leu Ser Ser Val Val Thr Val Pro Ser Ser Ser Leu Gly Thr Gln<br>200                          205                        210                       215 | 676 |
| acc tac atc tgc aac gtg aat cac aag ccc agc aac acc aag gtg gac<br>Thr Tyr Ile Cys Asn Val Asn His Lys Pro Ser Asn Thr Lys Val Asp<br>                    220                        225                       230 | 724 |
| aag aga gtt gag ccc aaa tct tgt gac aaa act cac aca tgc cca ccg<br>Lys Arg Val Glu Pro Lys Ser Cys Asp Lys Thr His Thr Cys Pro Pro<br>235                          240                        245 | 772 |
| tgc cca gca cct gaa ctc ctg ggg gga ccg tca gtc ttc ctc ttc ccc<br>Cys Pro Ala Pro Glu Leu Leu Gly Gly Pro Ser Val Phe Leu Phe Pro<br>250                          255                        260 | 820 |
| cca aaa ccc aag gac acc ctc atg atc tcc cgg acc cct gag gtc aca<br>Pro Lys Pro Lys Asp Thr Leu Met Ile Ser Arg Thr Pro Glu Val Thr<br>265                          270                        275 | 868 |
| tgc gtg gtg gtg gac gtg agc cac gaa gac cct gag gtc aag ttc aac<br>Cys Val Val Val Asp Val Ser His Glu Asp Pro Glu Val Lys Phe Asn<br>280                          285                        290                       295 | 916 |
| tgg tac gtg gac ggc gtg gag gtg cat aat gcc aag aca aag ccg cgg<br>Trp Tyr Val Asp Gly Val Glu Val His Asn Ala Lys Thr Lys Pro Arg<br>                    300                        305                       310 | 964 |
| gag gag cag tac aac agc acg tac cgt gtg gtc agc gtc ctc acc gtc<br>Glu Glu Gln Tyr Asn Ser Thr Tyr Arg Val Val Ser Val Leu Thr Val<br>315                          320                        325 | 1012 |
| ctg cac cag gac tgg ctg aat ggc aag gag tac aag tgc aag gtc tcc<br>Leu His Gln Asp Trp Leu Asn Gly Lys Glu Tyr Lys Cys Lys Val Ser<br>330                          335                        340 | 1060 |

```
aac aaa gcc ctc cca gcc ccc atc gag aaa acc atc tcc aaa gcc aaa    1108
Asn Lys Ala Leu Pro Ala Pro Ile Glu Lys Thr Ile Ser Lys Ala Lys
345             350                 355 ggg cag ccc cga gaa cca cag gtg tac acc ctg ccc cca tcc cgg gag    1156
Gly Gln Pro Arg Glu Pro Gln Val Tyr Thr Leu Pro Pro Ser Arg Glu
360             365                 370                 375 gag atg acc aag aac cag gtc agc ctg acc tgc ctg gtc aaa ggc ttc    1204
Glu Met Thr Lys Asn Gln Val Ser Leu Thr Cys Leu Val Lys Gly Phe
            380                 385                 390 tat ccc agc gac atc gcc gtg gag tgg gag agc aat ggg cag ccg gag    1252
Tyr Pro Ser Asp Ile Ala Val Glu Trp Glu Ser Asn Gly Gln Pro Glu
        395                 400                 405 aac aac tac aag acc acg cct ccc gtg ctg gac tcc gac ggc tcc ttc    1300
Asn Asn Tyr Lys Thr Thr Pro Pro Val Leu Asp Ser Asp Gly Ser Phe
    410                 415                 420 ttc ctc tat agc aag ctc acc gtg gac aag agc agg tgg cag cag ggg    1348
Phe Leu Tyr Ser Lys Leu Thr Val Asp Lys Ser Arg Trp Gln Gln Gly
425                 430                 435 aac gtc ttc tca tgc tcc gtg atg cat gag gct ctg cac aac cac tac    1396
Asn Val Phe Ser Cys Ser Val Met His Glu Ala Leu His Asn His Tyr
440                 445                 450                 455 acg cag aag agc ctc tcc ctg tcc ccg ggt aaa tga                    1432
Thr Gln Lys Ser Leu Ser Leu Ser Pro Gly Lys
                460                 465

<210> SEQ ID NO 4
<211> LENGTH: 466
<212> TYPE: PRT
<213> ORGANISM: Homo sapiens
<220> FEATURE:
<221> NAME/KEY: misc_feature
<222> LOCATION: (1)...(466)
<223> OTHER INFORMATION: Ha22-2(2,4)6.1 heavy chain

<400> SEQUENCE: 4

Met Glu Leu Gly Leu Cys Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Asn Met Asn Trp Val Arg Gln Ala Pro Gly Lys Gly Leu
    50                  55                  60

Glu Trp Val Ser Tyr Ile Ser Ser Ser Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Ser Leu Gln Met Asn Ser Leu Arg Asp Glu Asp Thr Ala Val
            100                 105                 110

Tyr Tyr Cys Ala Arg Ala Tyr Tyr Gly Met Asp Val Trp Gly Gln
        115                 120                 125

Gly Thr Thr Val Thr Val Ser Ser Ala Ser Thr Lys Gly Pro Ser Val
    130                 135                 140

Phe Pro Leu Ala Pro Ser Ser Lys Ser Thr Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
```

```
                  180                 185                 190
Leu Gln Ser Ser Gly Leu Tyr Ser Leu Ser Ser Val Val Thr Val Pro
            195                 200                 205
Ser Ser Ser Leu Gly Thr Gln Thr Tyr Ile Cys Asn Val Asn His Lys
        210                 215                 220
Pro Ser Asn Thr Lys Val Asp Lys Arg Val Glu Pro Lys Ser Cys Asp
225                 230                 235                 240
Lys Thr His Thr Cys Pro Pro Cys Pro Ala Pro Glu Leu Leu Gly Gly
                245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser His Glu
        275                 280                 285
Asp Pro Glu Val Lys Phe Asn Trp Tyr Val Asp Gly Val Glu Val His
    290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Arg Glu Glu Met Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys
465

<210> SEQ ID NO 5
<211> LENGTH: 735
<212> TYPE: DNA
<213> ORGANISM: Homo sapiens
<220> FEATURE:
<221> NAME/KEY: CDS
<222> LOCATION: (25)...(735)
<220> FEATURE:
<221> NAME/KEY: misc_feature
<222> LOCATION: (1)...(735)
<223> OTHER INFORMATION: Ha22-2(2,4)6.1 light chain

<400> SEQUENCE: 5
agtcagaccc agtcaggaca cagc atg gac atg agg gtc ccc gct cag ctc          51
                      Met Asp Met Arg Val Pro Ala Gln Leu
                        1               5 ctg ggg ctc ctg ctg ctc tgg ttc cca ggt tcc aga tgc gac atc cag          99
Leu Gly Leu Leu Leu Leu Trp Phe Pro Gly Ser Arg Cys Asp Ile Gln
    10                  15                  20                  25
```

| | | | | | | | | | | | | | | | | |
|---|---|---|---|---|---|---|---|---|---|---|---|---|---|---|---|---|
| atg | acc | cag | tct | cca | tct | tcc | gtg | tct | gca | tct | gtt | gga | gac | aga | gtc | 147 |
| Met | Thr | Gln | Ser | Pro | Ser | Ser | Val | Ser | Ala | Ser | Val | Gly | Asp | Arg | Val | |
| | | | 30 | | | | | 35 | | | | | 40 | | | |
| acc | atc | act | tgt | cgg | gcg | agt | cag | ggt | att | agc | ggc | tgg | tta | gcc | tgg | 195 |
| Thr | Ile | Thr | Cys | Arg | Ala | Ser | Gln | Gly | Ile | Ser | Gly | Trp | Leu | Ala | Trp | |
| | | | 45 | | | | | 50 | | | | | 55 | | | |
| tat | cag | cag | aaa | cca | ggg | aaa | gcc | cct | aag | ttc | ctg | atc | tat | gct | gca | 243 |
| Tyr | Gln | Gln | Lys | Pro | Gly | Lys | Ala | Pro | Lys | Phe | Leu | Ile | Tyr | Ala | Ala | |
| | | 60 | | | | | 65 | | | | | 70 | | | | |
| tcc | act | ttg | caa | agt | ggg | gtc | cca | tca | agg | ttc | agc | ggc | agt | gga | tct | 291 |
| Ser | Thr | Leu | Gln | Ser | Gly | Val | Pro | Ser | Arg | Phe | Ser | Gly | Ser | Gly | Ser | |
| | 75 | | | | | 80 | | | | | 85 | | | | | |
| ggg | aca | gat | ttc | act | ctc | acc | atc | agc | agc | ctg | cag | cct | gaa | gat | ttt | 339 |
| Gly | Thr | Asp | Phe | Thr | Leu | Thr | Ile | Ser | Ser | Leu | Gln | Pro | Glu | Asp | Phe | |
| 90 | | | | | 95 | | | | | 100 | | | | | 105 | |
| gca | act | tac | tat | tgt | caa | cag | gct | aac | agt | ttc | cct | ccc | act | ttc | ggc | 387 |
| Ala | Thr | Tyr | Tyr | Cys | Gln | Gln | Ala | Asn | Ser | Phe | Pro | Pro | Thr | Phe | Gly | |
| | | | | 110 | | | | | 115 | | | | | 120 | | |
| gga | ggg | acc | aag | gtg | gag | atc | aaa | cga | act | gtg | gct | gca | cca | tct | gtc | 435 |
| Gly | Gly | Thr | Lys | Val | Glu | Ile | Lys | Arg | Thr | Val | Ala | Ala | Pro | Ser | Val | |
| | | | 125 | | | | | 130 | | | | | 135 | | | |
| ttc | atc | ttc | ccg | cca | tct | gat | gag | cag | ttg | aaa | tct | gga | act | gcc | tct | 483 |
| Phe | Ile | Phe | Pro | Pro | Ser | Asp | Glu | Gln | Leu | Lys | Ser | Gly | Thr | Ala | Ser | |
| | | 140 | | | | | 145 | | | | | 150 | | | | |
| gtt | gtg | tgc | ctg | ctg | aat | aac | ttc | tat | ccc | aga | gag | gcc | aaa | gta | cag | 531 |
| Val | Val | Cys | Leu | Leu | Asn | Asn | Phe | Tyr | Pro | Arg | Glu | Ala | Lys | Val | Gln | |
| | 155 | | | | | 160 | | | | | 165 | | | | | |
| tgg | aag | gtg | gat | aac | gcc | ctc | caa | tcg | ggt | aac | tcc | cag | gag | agt | gtc | 579 |
| Trp | Lys | Val | Asp | Asn | Ala | Leu | Gln | Ser | Gly | Asn | Ser | Gln | Glu | Ser | Val | |
| 170 | | | | | 175 | | | | | 180 | | | | | 185 | |
| aca | gag | cag | gac | agc | aag | gac | agc | acc | tac | agc | ctc | agc | agc | acc | ctg | 627 |
| Thr | Glu | Gln | Asp | Ser | Lys | Asp | Ser | Thr | Tyr | Ser | Leu | Ser | Ser | Thr | Leu | |
| | | | | 190 | | | | | 195 | | | | | 200 | | |
| acg | ctg | agc | aaa | gca | gac | tac | gag | aaa | cac | aaa | gtc | tac | gcc | tgc | gaa | 675 |
| Thr | Leu | Ser | Lys | Ala | Asp | Tyr | Glu | Lys | His | Lys | Val | Tyr | Ala | Cys | Glu | |
| | | | 205 | | | | | 210 | | | | | 215 | | | |
| gtc | acc | cat | cag | ggc | ctg | agc | tcg | ccc | gtc | aca | aag | agc | ttc | aac | agg | 723 |
| Val | Thr | His | Gln | Gly | Leu | Ser | Ser | Pro | Val | Thr | Lys | Ser | Phe | Asn | Arg | |
| | | 220 | | | | | 225 | | | | | 230 | | | | |
| gga | gag | tgt | tag | | | | | | | | | | | | | 735 |
| Gly | Glu | Cys | | | | | | | | | | | | | | |
| | | 235 | | | | | | | | | | | | | | |

<210> SEQ ID NO 6
<211> LENGTH: 236
<212> TYPE: PRT
<213> ORGANISM: Homo sapiens
<220> FEATURE:
<221> NAME/KEY: misc_feature
<222> LOCATION: (1)...(236)
<223> OTHER INFORMATION: Ha22-2(2,4)6.1 light chain

<400> SEQUENCE: 6

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Gly Trp Leu Ala Trp Tyr Gln Gln Lys Pro Gly Lys
    50                  55                  60

```
Ala Pro Lys Phe Leu Ile Tyr Ala Ala Ser Thr Leu Gln Ser Gly Val
 65                  70                  75                  80

Pro Ser Arg Phe Ser Gly Ser Gly Ser Gly Thr Asp Phe Thr Leu Thr
             85                  90                  95

Ile Ser Ser Leu Gln Pro Glu Asp Phe Ala Thr Tyr Tyr Cys Gln Gln
            100                 105                 110

Ala Asn Ser Phe Pro Pro Thr Phe Gly Gly Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 7
<211> LENGTH: 466
<212> TYPE: PRT
<213> ORGANISM: Homo sapiens
<220> FEATURE:
<221> NAME/KEY: misc_feature
<222> LOCATION: (1)...(466)
<223> OTHER INFORMATION: Ha22-2(2,4)6.1 heavy chain

<400> SEQUENCE: 7

Met Glu Leu Gly Leu Cys Trp Val Phe Leu Val Ala Ile Leu Glu Gly
1               5                   10                  15

Val Gln Cys Glu Val Gln Leu Val Glu Ser Gly Gly Gly Leu Val Gln
             20                  25                  30

Pro Gly Gly Ser Leu Arg Leu Ser Cys Ala Ala Ser Gly Phe Thr Phe
            35                  40                  45

Ser Ser Tyr Asn Met Asn Trp Val Arg Gln Ala Pro Gly Lys Gly Leu
 50                  55                  60

Glu Trp Val Ser Tyr Ile Ser Ser Ser Ser Thr Ile Tyr Tyr Ala
 65                  70                  75                  80

Asp Ser Val Lys Gly Arg Phe Thr Ile Ser Arg Asp Asn Ala Lys Asn
             85                  90                  95

Ser Leu Ser Leu Gln Met Asn Ser Leu Arg Asp Glu Asp Thr Ala Val
            100                 105                 110

Tyr Tyr Cys Ala Arg Ala Tyr Tyr Gly Met Asp Val Trp Gly Gln
            115                 120                 125

Gly Thr Thr Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175
```

```
Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
        210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
450                 455                 460

Gly Lys
465

<210> SEQ ID NO 8
<211> LENGTH: 236
<212> TYPE: PRT
<213> ORGANISM: Homo sapiens
<220> FEATURE:
<221> NAME/KEY: misc_feature
<222> LOCATION: (1)...(236)
<223> OTHER INFORMATION: Ha22-2(2,4)6.1 light chain

<400> SEQUENCE: 8

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Gly Trp Leu Ala Trp Tyr Gln Gln Lys Pro Gly Lys
```

```
                50                  55                  60
Ala Pro Lys Phe Leu Ile Tyr Ala Ala Ser Thr Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
                100                 105                 110

Ala Asn Ser Phe Pro Pro Thr Phe Gly Gly Gly Thr Lys Val Glu Ile
                115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235
```

<210> SEQ ID NO 9
<211> LENGTH: 98
<212> TYPE: PRT
<213> ORGANISM: Homo sapiens
<220> FEATURE:
<221> NAME/KEY: misc_feature
<222> LOCATION: (1)...(98)
<223> OTHER INFORMATION: Human Ig germline VH3-48

<400> SEQUENCE: 9

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Tyr Ile Ser Ser Ser Ser Ser Thr Ile Tyr Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                85                  90                  95

Ala Arg
```

<210> SEQ ID NO 10
<211> LENGTH: 96
<212> TYPE: PRT
<213> ORGANISM: Homo sapiens
<220> FEATURE:
<221> NAME/KEY: misc_feature
<222> LOCATION: (1)...(96)
<223> OTHER INFORMATION: Human Ig germline L5

<400> SEQUENCE: 10

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95
```

<210> SEQ ID NO 11
<211> LENGTH: 179
<212> TYPE: PRT
<213> ORGANISM: Mus musculus
<220> FEATURE:
<221> NAME/KEY: misc_feature
<222> LOCATION: (1)...(179)
<223> OTHER INFORMATION: 191P4D12 ortholog containing the V-domain

<400> SEQUENCE: 11

```
Met Pro Leu Ser Leu Gly Ala Glu Met Trp Gly Pro Glu Ala Trp Leu
1               5                   10                  15

Arg Leu Leu Phe Leu Ala Ser Phe Thr Gly Gln Tyr Ser Ala Gly Glu
            20                  25                  30

Leu Glu Thr Ser Asp Val Val Thr Val Val Leu Gly Gln Asp Ala Lys
        35                  40                  45

Leu Pro Cys Phe Tyr Arg Gly Asp Pro Asp Glu Gln Val Gly Gln Val
50                  55                  60

Ala Trp Ala Arg Val Asp Pro Asn Glu Gly Ile Arg Glu Leu Ala Leu
65                  70                  75                  80

Leu His Ser Lys Tyr Gly Leu His Val Asn Pro Ala Tyr Glu Asp Arg
                85                  90                  95

Val Glu Gln Pro Pro Pro Arg Asp Pro Leu Asp Gly Ser Val Leu
            100                 105                 110

Leu Arg Asn Ala Val Gln Ala Asp Glu Gly Glu Tyr Glu Cys Arg Val
        115                 120                 125

Ser Thr Phe Pro Ala Gly Ser Phe Gln Ala Arg Met Arg Leu Arg Val
130                 135                 140

Leu Val Pro Pro Leu Pro Ser Leu Asn Pro Gly Pro Pro Leu Glu Glu
145                 150                 155                 160

Gly Gln Gly Leu Thr Leu Ala Ala Ser Cys Thr Ala Glu Gly Ser Pro
                165                 170                 175

Ala Pro Ser
```

<210> SEQ ID NO 12
<211> LENGTH: 179
<212> TYPE: PRT
<213> ORGANISM: Rattus norvegicus
<220> FEATURE:
<221> NAME/KEY: misc_feature
<222> LOCATION: (1)...(179)
<223> OTHER INFORMATION: 191P4D12 ortholog containing the V-domain

<400> SEQUENCE: 12

```
Met Pro Leu Ser Leu Gly Ala Glu Met Trp Gly Pro Glu Ala Trp Leu
1               5                   10                  15
```

```
Leu Leu Leu Phe Leu Ala Ser Phe Thr Gly Arg Tyr Ser Ala Gly Glu
            20                  25                  30

Leu Glu Thr Ser Asp Leu Val Thr Val Val Leu Gly Gln Asp Ala Lys
            35                  40                  45

Leu Pro Cys Phe Tyr Arg Gly Asp Pro Asp Glu Gln Val Gly Gln Val
        50                  55                  60

Ala Trp Ala Arg Val Asp Pro Asn Glu Gly Thr Arg Glu Leu Ala Leu
65                  70                  75                  80

Leu His Ser Lys Tyr Gly Leu His Val Ser Pro Ala Tyr Glu Asp Arg
                85                  90                  95

Val Glu Gln Pro Pro Pro Arg Asp Pro Leu Asp Gly Ser Ile Leu
            100                 105                 110

Leu Arg Asn Ala Val Gln Ala Asp Glu Gly Glu Tyr Glu Cys Arg Val
            115                 120                 125

Ser Thr Phe Pro Ala Gly Ser Phe Gln Ala Arg Met Arg Leu Arg Val
        130                 135                 140

Leu Val Pro Pro Leu Pro Ser Leu Asn Pro Gly Pro Leu Glu Glu
145                 150                 155                 160

Gly Gln Gly Leu Thr Leu Ala Ala Ser Cys Thr Ala Glu Gly Ser Pro
                165                 170                 175

Ala Pro Ser

<210> SEQ ID NO 13
<211> LENGTH: 180
<212> TYPE: PRT
<213> ORGANISM: Homo sapiens
<220> FEATURE:
<221> NAME/KEY: misc_feature
<222> LOCATION: (1)...(180)
<223> OTHER INFORMATION: 191P4D12 ortholog containing the V-domain

<400> SEQUENCE: 13

Met Pro Leu Ser Leu Gly Ala Glu Met Trp Gly Pro Glu Ala Trp Leu
1               5                   10                  15

Leu Leu Leu Leu Leu Leu Ala Ser Phe Thr Gly Arg Cys Pro Ala Gly
            20                  25                  30

Glu Leu Glu Thr Ser Asp Val Val Thr Val Val Leu Gly Gln Asp Ala
            35                  40                  45

Lys Leu Pro Cys Phe Tyr Arg Gly Asp Ser Gly Glu Gln Val Gly Gln
        50                  55                  60

Val Ala Trp Ala Arg Val Asp Ala Gly Glu Gly Ala Gln Glu Leu Ala
65                  70                  75                  80

Leu Leu His Ser Lys Tyr Gly Leu His Val Ser Pro Ala Tyr Glu Gly
                85                  90                  95

Arg Val Glu Gln Pro Pro Pro Arg Asn Pro Leu Asp Gly Ser Val
            100                 105                 110

Leu Leu Arg Asn Ala Val Gln Ala Asp Glu Gly Glu Tyr Glu Cys Arg
            115                 120                 125

Val Ser Thr Phe Pro Ala Gly Ser Phe Gln Ala Arg Leu Arg Leu Arg
        130                 135                 140

Val Leu Val Pro Pro Leu Pro Ser Leu Asn Pro Gly Pro Ala Leu Glu
145                 150                 155                 160
```

```
Glu Gly Gln Gly Leu Thr Leu Ala Ala Ser Cys Thr Ala Glu Gly Ser
            165                 170                 175
Pro Ala Pro Ser
            180
```